United States Patent
Gilon et al.

(12)

(10) Patent No.: US 6,407,059 B1
(45) Date of Patent: *Jun. 18, 2002

(54) CONFORMATIONALLY CONSTRAINED BACKBONE CYCLIZED PEPTIDE ANALOGS

(75) Inventors: Chaim Gilon, Jerusalem; Doron Eren, Rehovot; Irina Zeltser, Jerusalem; Alon Seri-Levy, Jerusalem; Gal Bitan, Jerusalem; Dan Muller, Jerusalem, all of (IL)

(73) Assignee: Peptor Limited, Rehovot (IL)

( * ) Notice: Subject to any disclaimer, the term of this patent is extended or adjusted under 35 U.S.C. 154(b) by 59 days.

This patent is subject to a terminal disclaimer.

(21) Appl. No.: 09/580,905

(22) Filed: May 31, 2000

Related U.S. Application Data

(62) Division of application No. 09/120,237, filed on Jul. 22, 1998, now Pat. No. 6,265,375, which is a continuation of application No. 08/488,159, filed on Jun. 7, 1995, now Pat. No. 5,811,392.

(30) Foreign Application Priority Data

Jun. 8, 1994 (IL) ................................................. 109943

(51) Int. Cl.[7] ............................ A61K 38/12; C07K 7/64
(52) U.S. Cl. ................................ 514/9; 514/10; 514/11; 530/311; 530/317
(58) Field of Search ................................ 530/317, 311; 514/9, 10, 11

(56) References Cited

U.S. PATENT DOCUMENTS 5,874,529 A  *  2/1999  Gilon et al. ................. 530/317

FOREIGN PATENT DOCUMENTS

EP      564739      * 10/1993

OTHER PUBLICATIONS

Byk et al. Building Units for N–Backbone Cyclic Peptdies. 1. Synthesis of Protected N–(ω–Aminoalkylene) Amion Acids and their Incroporation into Dipeptide Units. J. Org. Chem. vol. 57, pp. 5687–5692 (1992).*

Gilon et al. "Backbone Cyclization: A New Method for Conferring Conformational Contraints on Peptides," Biopolyjmers, Vo. 31, pp. 745–750.*

* cited by examiner

Primary Examiner—Christopher S. F. Low
Assistant Examiner—Anish Gupta
(74) Attorney, Agent, or Firm—Winston & Strawn

(57) ABSTRACT

Novel backbone cyclized peptide analogs are formed by means of bridging groups attached via the alpha nitrogens of amino acid derivatives to provide novel non-peptidic linkages. Novel building units disclosed are $N^{\alpha}(\omega$-functionalized) amino acids constructed to include a spacer and a terminal functional group. One or more of these $N^{\alpha}(\omega$-functionalized) amino acids are incorporated into a peptide sequence, preferably during solid phase peptide synthesis. The reactive terminal functional groups are protected by specific protecting groups that can be selectively removed to effect either backbone-to-backbone or backbone-to-side chain cyclizations. The invention is specifically exemplified by backbone cyclized bradykinin antagonists having biological activity. Further embodiments of the invention are somatostatin analogs having one or two ring structures involving backbone cyclization.

6 Claims, 1 Drawing Sheet

CONFORMATIONALLY CONSTRAINED BACKBONE CYCLIZED PEPTIDE ANALOGS

This appln. is a Div. of Ser. No. 09/120,237 filed Jul. 22, 1998, U.S. Pat. No. 6,265,375 which is a continuation of Ser. No. 08/488,159 filed Jun. 7, 1995 U.S. Pat. No. 5,811,392.

FIELD OF THE INVENTION

The present invention relates to conformationally constrained $N^\alpha$ backbone-cyclized peptide analogs cyclized via novel non-peptidic linkages, to novel $N^\alpha,\omega$-functionalized amino acid building units, to processes for the preparation of these backbone cyclized peptides and building units, to methods for using these peptide analogs and to pharmaceutical compositions containing same.

BACKGROUND OF THE INVENTION

Peptidomimetics

As a result of major advances in organic chemistry and in molecular biology, many bioactive peptides can now be prepared in quantities sufficient for pharmacological and clinical utilities. Thus in the last few years new methods have been established for the treatment and therapy of illnesses in which peptides have been implicated. However, the use of peptides as drugs is limited by the following factors: a) their low metabolic stability towards proteolysis in the gastrointestinal tract and in serum; b) their poor absorption after oral ingestion, in particular due to their relatively high molecular mass or the lack of specific transport systems or both; c) their rapid excretion through the liver and kidneys; and d) their undesired side effects in non-target organ systems, since peptide receptors can be widely distributed in an organism.

Moreover, with few exceptions, native peptides of small to medium size (less than 30–50 amino acids) exist unordered in dilute aqueous solution in a multitude of conformations in dynamic equilibrium which may lead to lack of receptor selectivity, metabolic susceptibilities and hamper attempts to determine the biologically active conformation. If a peptide has the biologically active conformation per se, i.e., receptor-bound conformation, then an increased affinity toward the receptor is expected, since the decrease in entropy on binding is less than that on the binding of a flexible peptide. It is therefore important to strive for and develop ordered, uniform and biologically active peptides.

In recent years, intensive efforts have been made to develop peptidomimetics or peptide analogs that display more favorable pharmacological properties than their prototype native peptides. The native peptide itself, the pharmacological properties of which have been optimized, generally serves as a lead for the development of these peptidomimetics. However, a major problem in the development of such agents is the discovery of the active region of a biologically active peptide. For instance, frequently only a small number of amino acids (usually four to eight) are responsible for the recognition of a peptide ligand by a receptor. Once this biologically active site is determined a lead structure for development of peptidomimetic can be optimized, for example by molecular modeling programs.

As used herein, a "peptidomimetic" is a compound that, as a ligand of a receptor, can imitate (agonist) or block (antagonist) the biological effect of a peptide at the receptor level. The following factors should be considered to achieve the best possible agonist peptidomimetic a) metabolic stability, b) good bioavailability, c) high receptor affinity and receptor selectivity, and d) minimal side effects.

From the pharmacological and medical viewpoint it is frequently desirable to not only imitate the effect of the peptide at the receptor level (agonist) but also to block the receptor when required (antagonism). The same pharmacological considerations for designing an agonist peptidomimetic mentioned above hold for designing peptide antagonists, but, in addition, their development in the absence of lead structures is more difficult. Even today it is not unequivocally clear which factors are decisive for the agonistic effect and which are for the antagonistic effect.

A generally applicable and successful method recently has been the development of conformationally restricted peptidomimetics that imitate the receptor-bound conformation of the endogenous peptide ligands as closely as possible (Rizo and Gierasch, *Ann. Rev. Biochem.*, 61:387, 1992). Investigations of these types of analogs show them to have increased resistance toward proteases, that is, an increase in metabolic stability, as well as increased selectivity and thereby fewer side effects (Veber and Friedinger, *Trends Neurosci.*, p. 392, 1985).

Once these peptidomimetic compounds with rigid conformations are produced, the most active structures are selected by studying the conformation-activity relationships. Such conformational constraints can involve short range (local) modifications of structure or long range (global) conformational restraints (for review see Giannis and Kolter, *Angew. Chem. Int. Ed. Enal.* 32:1244, 1993).

Conformationally Constrained Peptides

Bridging between two neighboring amino acids in a peptide leads to a local conformational modification, the flexibility of which is limited in comparison with that of regular dipeptides. Some possibilities for forming such bridges include incorporation of lactams and piperazinones. γ-Lactams and δ-lactams have been designed to some extent as "turn mimetics"; in several cases the incorporation of such structures into peptides leads to biologically active compounds.

Global restrictions in the conformation of a peptide are possible by limiting the flexibility of the peptide strand through cyclization (Hruby et al., *Biochem. J.*, 268:249, 1990). Not only does cyclization of bioactive peptides improve their metabolic stability and receptor selectivity, cyclization also imposes constraints that enhance conformational homogeneity and facilitates conformational analysis. The common modes of cyclization are the same found in naturally occurring cyclic peptides. These include side chain to side chain cyclization or side chain to end-group cyclization. For this purpose, amino acid side chains that are not involved in receptor recognition are connected together or to the peptide backbone. Another common cyclization is the end-to-end cyclization.

Three representative examples are compounds wherein partial structures of each peptide are made into rings by linking two penicillamine residues with a disulfide bridge (Mosberg et al., *P.N.A.S. US*, 80:5871, 1983), by formation of an amide bond between a lysine and an aspartate group (Charpentier et al., *J. Med. Chem.* 32:1184, 1989), or by connecting two lysine groups with a succinate unit (Rodriguez et al., *Int. J. Pept. Protein Res.* 35:441, 1990). These structures have been disclosed in the literature in the case of a cyclic enkephalin analog with selectivity for the δ-opiate receptor (Mosberg et al., ibid.); or as agonists to the cholecystokinin B receptor, found largely in the brain (Charpentier et al., ibid., Rodriguez et al., ibid.).

The main limitations to these classical modes of cyclization are that they require substitution of amino acid side chains in order to achieve cyclization.

Another conceptual approach to the conformational constraint of peptides was introduced by Gilon, et al., (Biopolymers, 31:745, 1991) who proposed backbone to backbone cyclization of peptides. The theoretical advantages of this strategy include the ability to effect cyclization via the carbons or nitrogens of the peptide backbone without interfering with side chains that may be crucial for interaction with the specific receptor of a given peptide. While the concept was envisaged as being applicable to any linear peptide of interest, in point of fact the limiting factor in the proposed scheme was the availability of suitable building units that must be used to replace the amino acids that are to be linked via bridging groups. The actual reduction to practice of this concept of backbone cyclization was prevented by the inability to devise any practical method of preparing building units of amino acids other than glycine (Byk et al., J. Org. Chem., 587:5687, 1992). While analogs of other amino acids were attempted the synthetic method used was unsuccessful or of such low yield as to preclude any general applicability.

In Gilon, EPO Application No. 564,739 A2; and J. Org. Chem., 57:5687, 1992, two basic approaches to the synthesis of building units are described. The first starts with the reaction of a diamine with a general a bromo acid. Selective protection of the w amine and further elaborations of protecting groups provides a building unit, suitable for Boc chemistry peptide synthesis. The second approach starts with selective protection of a diamine and reaction of the product with chloroacetic acid to provide the protected glycine derivative, suitable for Fmoc peptide synthesis.

Both examples deal with the reaction of a molecule of the general type X—CH(R)—CO—OR' (wherein X represents a leaving group which, in the examples given, is either Br or Cl) with an amine which replaces the X. The amine bears an alkylidene chain which is terminated by another functional group, amine in the examples described, which may or may not be blocked by a protecting group.

In all cases the a nitrogen of the end product originates in the molecule which becomes the bridging chain for subsequent cyclization. This approach was chosen in order to take advantage of the higher susceptibility to nucleophilic displacement of a leaving group next to a carboxylic group.

In a molecule where R is different than hydrogen there is a high tendency to eliminate HX under basic conditions. This side reaction reduces the yield of Gilon's method to the point where it is impractical for production of building units based on amino acids other than glycine. The diamine nitrogen is primary while the product contains a secondary nitrogen, which is a better nucleophile. So while the desired reaction may be sluggish, and require the addition of catalysts, the product may be contaminated with double alkylation products. There is no mention of building units with end group chemistries other than nitrogen, so the only cyclization schemes possible are backbone to side chain and backbone to C terminus.

Applications of Conformationally Constrained Peptides

Conformationally constrained peptides find many pharmacological uses. Somatostatin is a cyclic tetradecapeptide found both in the central nervous system and in peripheral tissues. It was originally isolated from mammalian hypothalamus and identified as an important inhibitor of growth hormone secretion from the anterior pituitary. Its multiple biological activities include inhibition of the secretion of glucagon and insulin from the pancreas, regulation of most gut hormones and regulation of the release of other neurotransmitters involved in motor activity and cognitive processes throughout the central nervous system (for review see Lamberts, Endocrine Rev., 9:427, 1988).

Natural somatostatin (also known as Somatotropin Release Inhibiting Factor, SRIF) of the following structure:

H-Ala$^1$-Gly$^2$-Cys$^3$-Lys$^4$-Asn$^5$-Phe$^6$-Phe$^7$-Trp$^8$-Lys$^9$-Thr$^{10}$-Phe$^{11}$-Thr$^{12}$-Ser$^{13}$-Cys$^{14}$-OH was first isolated by Guillemin and colleagues (Brazeau et al. Science, 179:78, 1973). In its natural form, it has limited use as a therapeutic agent since it exhibits two undesirable properties: poor bioavailability and short duration of action. For this reason, great efforts have been made during the last two decades to find somatostatin analogs that will have superiority in either potency, biostability, duration of action or selectivity with regard to inhibition of the release of growth hormone, insulin or glucagon.

Structure-activity relation studies, spectroscopic techniques such as circular dichroism and nuclear magnetic resonance, and molecular modeling approaches reveal the following: the conformation of the cyclic part of natural somatostatin is most likely to be an antiparallel β-sheet; Phe$^6$ and Phe$^{11}$ play an important role in stabilizing the pharmacophore conformation through hydrophobic interactions between the two aromatic rings; the four amino acids Phe$^7$-Trp$^8$-Lys$^9$-Thr$^{10}$ which are spread around the β-turn in the antiparallel β-sheet are essential for the pharmacophore; and (D)Trp$^8$ is almost always preferable to (L)Trp$^8$.

Nevertheless, a hexapeptide somatostatin analog containing these four amino acids anchored by a disulfide bridge:

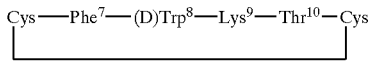

is almost inactive both in vitro and in vivo, although it has the advantage of the covalent disulfide bridge which replaces the Phe$^6$-Phe$^{11}$ hydrophobic interactions in natural somatostatin.

Four main approaches have been attempted in order to increase the activity of this hexapeptide somatostatin analog. (1) Replacing the disulfide bridge by a cyclization which encourages a cis-amide bond, or by performing a second cyclization to the molecule yielding a bicyclic analog. In both cases the resultant analog has a reduced number of conformational degrees of freedom. (2) Replacing the original amino acids in the sequence Phe$^7$-(D)Trp$^8$-Lys$^9$-Thr$^{10}$ with more potent amino acid analogs, such as replacing Phe$^7$ with Tyr$^7$ and Thr$^{10}$ with Val$^{10}$. (3) Incorporating additional structural elements from natural somatostatin with the intention that these new elements will contribute to the interaction with the receptor. (4) Eliminating one of the four amino acids Phe$^7$-(D)Trp$^8$-Lys$^9$-Thr$^{10}$ with the assumption that such analogs would be more selective.

The somatostatin analog, MK-678:
cyclo(N-Me-Ala$^7$-Tyr$^7$-(D)Trp$^8$-Lys$^9$-Val$^{10}$-Phe)
is an example of a highly potent somatostatin analog designed using the first three approaches above (Lymangrover, et al., Life Science, 34:371, 1984). In this hexapeptide analog, a cis-amide bond is located between N-Me-Ala and Phe$^{11}$, Tyr$^7$ and Val$^{10}$ replace Phe$^7$ and Thr$^{10}$ respectively, and Phe$^{11}$ is incorporated from natural somatostatin.

Another group of somatostatin analogs (U.S. Pat. Nos. 4,310,518 and 4,235,886) includes octreotide:

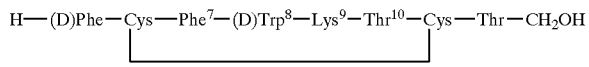

the only somatostatin analog currently available. It was developed using the third approach described above. Here, (D)Phe$^5$ and the reduced C-terminal Thr$^{12}$-CH$_2$OH are assumed to occupy some of the conformational space available to the natural Phe$^6$ and Thr$^{12}$, respectively.

The compound TT2–32:

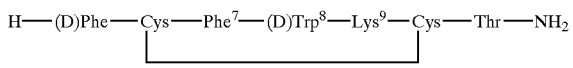

is closely related to octreotide and is an example of implementing the fourth approach described above. The lack of Thr[10] is probably responsible for its high selectivity in terms of antitumor activity.

These examples of highly potent somatostatin analogs indicate that the phenylalanines in positions 6 and 11 not only play an important role in stabilizing the pharmacophore conformation but also have a functional role in the interaction with the receptor. It is still an open question whether one phenylalanine (either Phe[6] or Phe[11]) is sufficient for the interaction with the receptor or whether both are needed.

It is now known that the somatostatin receptors constitute a family of five different receptor subtypes (Bell and Reisine, *Trends Neurosci.*, 16, 34–38, 1993), which may be distinguished on the basis of their tissue specificity and/or biological activity. Somatostatin analogs known in the art may not provide sufficient selectivity or receptor subtype selectivity, particularly as anti-neoplastic agents (Reubi and Laissue, *TIPS*, 16, 110–115, 1995).

Symptoms associated with metastatic carcinoid tumors (flushing and diarrhea) and vasoactive intestinal peptide (VIP) secreting adenomas (watery diarrhea) are treated with somatostatin analogs. Somatostatin has been also approved for the treatment of severe gastrointestinal hemorrhages. Somatostatin may also be useful in the palliative treatment of other hormone-secreting tumors (e.g., pancreatic islet-cell tumors and acromegaly) and hormone dependent tumors (e.g., chondrosarcoma and osteosarcoma) due to its antisecretory activity.

Another important peptide, Bradykinin, is a naturally occurring nonapeptide,
Arg[1]-Pro[2]-Pro[3]-Gly[4]-Phe[5]-Ser[6]-Pro[7]-Phe[8]-Arg[9], formed and released from precursors in the blood in response to inflammatory stimuli. Elevated levels of bradykinin also appear in other body fluids and tissues in pathological states such as asthma, septic shock and common cold. No clinical abnormalities have been associated so far with bradykinin deficiency which indicates that bradykinin may not play a critical role in normal physiology.

However, bradykinin mediates its physiological activities by binding to a specific receptive molecule called the bradykinin receptor. Two such bradykinin receptors have been identified so far (these are called B1 and B2 receptors). Subsequent to binding, the bradykinin signal transduction pathway includes production of prostaglandins and leukotrienes as well as calcium activation. Through these mediators, bradykinin is involved in pain, inflammation, allergic reactions and hypotension. Therefore, a substance that can block the ability of bradykinin to bind to its receptor, namely a bradykinin antagonist, should have a significant therapeutic value for one of the following indications: asthma, inflammation, septic shock, pain, hypotension and allergy.

The analog used herein to exemplify backbone cyclization is:

D-Arg[0]-Arg-R[1]-Hyp[3]-Gly-Phe-R[2]-D-Phe-Phe[7]-Arg (wherein, R[1] is Pro, R[2] is Ser in native bradykinin). The change of proline at position 7 of native bradykinin to D-Phe confers antagonist activity. This compound was described in Steranka, et al., *P.N.A.S. U.S.*, 85:3245–3249, 1988 and is one of a plethora of candidate sequences for modification by the current technology, i.e. backbone cyclization. In this regard, it is worth noting the applications: WO89/01781, EP-A-0370453 and EP-A-0334244 which disclose a widerange of candidate structures. Antagonist peptides on which stability and/or tissue selectivity can be conferred by appropriate cyclization will be selected from the many such known sequences.

According to the present invention a novel synthetic approach is disclosed providing N$^\alpha$(ω(functionalized) alkylene)amino acid building units that can be used to synthesize novel N$^\alpha$-backbone cyclized peptide analogs such as, but not limited to, novel somatostatin and bradykinin analogs. None of the above-mentioned references teaches or suggests N$^\alpha$-(ω(functionalized)alkylene)amino acids or the novel N$^\alpha$-backbone cyclized peptide analogs of the present invention.

SUMMARY OF THE INVENTION

It is an object of the present invention to provide backbone cyclized peptide analogs that comprise peptide sequences which incorporate at least two building units, each of which contains one nitrogen atom of the peptide backbone connected to a bridging group as described below. In the present invention, one or more pairs of the building units is joined together to form a cyclic structure. Thus, according to one aspect of the present invention, backbone cyclized peptide analogs are provided that have the general Formula (I):

Formula (I)

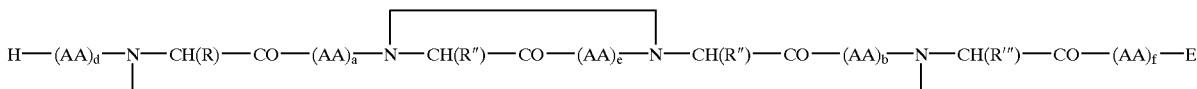

wherein: a and b each independently designates an integer from 1 to 8 or zero; d, e, and f each independently designates an integer from 1 to 10; (AA) designates an amino acid residue wherein the amino acid residues in each chain may be the same or different; E represents a hydroxyl group, a carboxyl protecting group or an amino group, or CO—E can be reduced to $CH_2$—OH; R. R', R", and R'" each designates an amino acid side-chain such as H, $CH_3$, etc., optionally bound with a specific protecting group; and the lines independently designate a bridging group of the Formula: (i) —X—M—Y—W—Z— ; or (ii) —X—M—Z— wherein: one line may be absent; M and W are independently selected from the group consisting of disulfide, amide, thioether, thioesters, imines, ethers and alkenes; and X, Y and Z are each independently selected from the group consisting of alkylene, substituted alkylene, arylene, homo- or heterocycloalkylene and substituted cycloalkylene.

In certain preferred embodiments, the CO—E group of Formula (I) is reduced to a $CH_2OH$ group.

Another embodiment of the present invention involves N-backbone to side chain cyclized peptides of the general formula (II):

Formula (II)

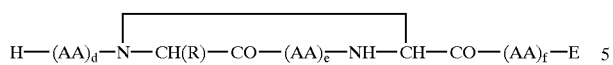

wherein x is an integer of 1 to 10; K is H or an acyl group; ($R^6$) is selected from the group of D-Asp, L-Asp, D-Glu and L-Glu; and z is according to the amino acid specified: 1 in case of D and L-Asp, and 2 in the case of D and L Glu.

Further more preferred backbone cyclized peptide analogs according to the present invention having bradykinin antagonist activity have the Formula (V):

Formula (V)

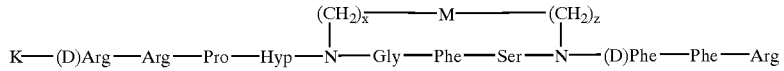

wherein the substituents are as defined above.

A preferred embodiment of the present invention involves the backbone cyclized peptide analog of Formulae I or II wherein the line designates a bridging group of the Formula: —$(CH_2)_x$—M—$(CH_2)_y$—W—$(CH_2)_z$— wherein M and W are independently selected from the group consisting of disulfide, amide, thioether, thioesters, imines, ethers and alkenes; x and z each independently designates an integer from 1 to 10, and y is zero or an integer of from 1 to 8, with the proviso that if y is zero, W is absent.

Further preferred are backbone cyclized peptide analogs of the Formula I or II wherein R and R' are other than H, such as $CH_3$, $(CH_3)_2CH$—, $(CH_3)_2CHCH_2$—, $CH_3CH_2CH(CH_3)$—, $CH_3S(CH_2)_2$—, $HOCH_2$—, $CH_3CH(OH)$—, $HSCH_2$—, $NH_2C(=O)CH_2$—, $NH_2C(=O)(CH_2)_2$—, $NH_2(CH_2)_3$—, $HOC(=O)CH_2$—, $HOC(=O)(CH_2)_2$—, $NH_2(CH_2)_4$—, $C(NH_2)_2 NH(CH_2)_3$—, HO-phenyl-$CH_2$—, benzyl, methylindole, and methylimidazole.

A more preferred embodiment of the present invention is directed to backbone cyclization to stabilize the β-turn conformation of bradykinin analogs of the general Formula (III):

wherein M is an amide bond, x and z are each independently an integer of 1 to 10, and K is H or an acyl group.

Specifically preferred backbone cyclized peptide analogs of the present invention are:
1) Ada-(D)Arg-Arg-cyclo($N^α$(1-(6-aminohexylene)Gly-Hyp-Phe-D-Asp)-D-Phe-Phe-Arg-OH;
2) H-D-Arg-Arg-cyclo($N^α$(1-(4-propanoyl))Gly-Hyp-Phe-$N^α$(3-amido-propylene)Gly)-Ser-D-Phe-Phe-Arg-OH; and
3) H-D-Arg-Arg-cyclo($N^α$(4-propanoyl)Gly-Hyp-Phe-N(3-amido-propyl)-S-Phe)-Ser-D-Phe-Phe-Arg-OH.

Another preferred aspect of the present invention is directed to backbone cyclizatiog to generate novel somatostatin analogs linked between positions 6 and 11, leaving the phenylalanine side chains untouched. This conformational stabilization is much more rigid than the $Phe^6$, $Phe^{11}$ hydrophobic interaction in natural somatostatin and is more stable to reduction/oxidation reactions than the Cys-Cys disulfide bridge. In other words, for the first time a stable covalent bridge can be achieved while either one or both of the original $Phe^6$ and $Phe^{11}$ are retained.

Moreover, backbone cyclizations can also be used to anchor the β-turn, not only in positions 6 and 11 but also Formula III

wherein M is an amide bond, x and z are each independently an integer of 1 to 10, and K is H or an acyl group.

Also more preferred are backbone cyclized peptide analogs of the present invention comprising bradykinin analogs of the general Formula (IVa):

inside the active reaction of $Phe^7$-(D)$Trp^8$-$Lys^9$-$Thr^{10}$, yielding either a monocyclic analog with a preferable conformation or a very rigid bicyclic analog. Here again, the side Formula (IVa)

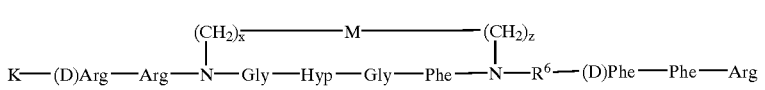

wherein M is an amide bond, x and z are each independently an integer of 1 to 10, K is H or an acyl group, and $R^6$ is Gly or Ser; or the general Formula (IVb):

chains of the pharmacologically active amino acids remain untouched and the only change is in limiting the conformational space.

Formula (IVb)

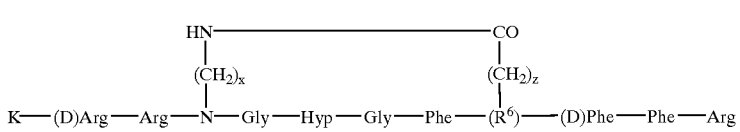

As used herein and in the claims in the following more preferred backbone cyclized peptide analogs, the superscript numbers following the amino acids refer to their position numbers in the native Somatostatin.

A more preferred backbone cyclized peptide novel analog is the Formula (XIVa):

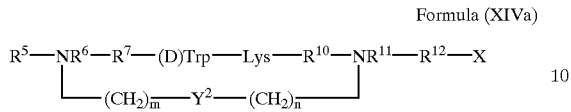

Formula (XIVa)

with a most preferred analog being the Formula (XIVb):

FIG. (XIVb)

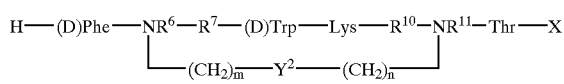

wherein m and n are 1, 2 or 3; X is $CH_2OH$ or $CONH_2$; $R^5$ is absent or is Gly, (D)- or (L)-Ala, Phe, Nal and β-Asp(Ind); $R^6$ and $R^{11}$ are independently Gly or (D)- or (L)-Phe; $R^7$ is Phe or Tyr; $R^{10}$ is absent or is Gly, Abu, Thr or Val; $R^{12}$ is absent or is Thr or Nal, and $Y^2$ is selected from the group consisting of amide, disulfide, thioether, imines, ethers and alkenes. In these monocyclic somatostatin analogs, a backbone cyclization replaces the $Cys^6$-$Cys^{11}$ disulfide bridge, leaving the phenylalanine side chains as in the natural somatostatin. Still more preferred is the analog wherein $Phe^7$ is replaced with $Tyr^7$ and $Thr^{10}$ is replaced with $Val^{10}$.

Other more preferred monocyclic analogs that anchor the molecule in positions inside the active region rather than in positions 6 and 11 are formulae XV (a and b) and XVI (a–c):

Formula (XVa)

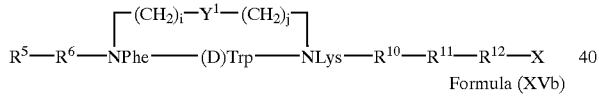

Formula (XVb)

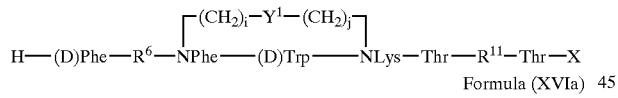

Formula (XVIa)

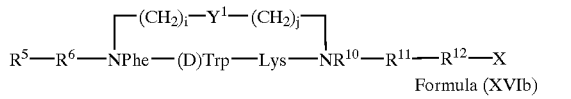

Formula (XVIb)

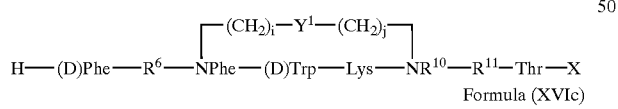

Formula (XVIc)

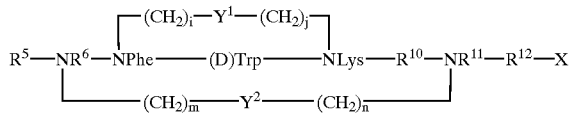

wherein i and j are independently 1, 2 or 3; X is $CH_2OH$ or $CONH_2$; $R^5$ is absent or is (D)- or (L)-Phe, Nal, or β-Asp(Ind); $R^6$ is (D) or (L)-Phe; $R^{10}$ is absent or is Gly, Abu or Thr; and $R^{11}$ is (D)- or (L)-Phe; $R^{12}$ is absent or is Thr or Nal, and $Y^1$ is selected from the group consisting of amide, disulfide, thioether, imines, ethers and alkenes.

Still other more preferred analogs incorporate backbone cyclization in positions 6 and 11 as in Formula XIV, together with the backbone cyclizations as in Formula XV and XVI, yielding rigid bicyclic analogs of the Formulae XVII (a and b) and XVIII (a and b):

Formula (XVIIa)

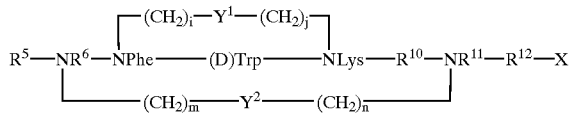

Formula (XVIIb)

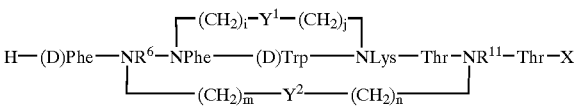

Formula (XVIIIa)

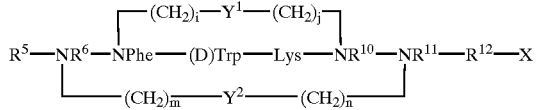

Formula (XVIIIb)

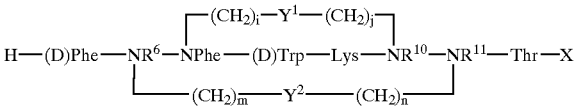

wherein i, j, m and n are independently 1, 2 or 3; X is $CH_2OH$ or $CONH_2$; $R^5$ is absent or is (D)- or (L)-Phe, Nal, or β-Asp(Ind); $R^6$ and $R^{11}$ are independently Gly or (D)- or (L)-Phe; $R^{10}$ is absent or is Gly, Abu, Val or Thr; $R^{12}$ is absent or is Thr or Nal; and $Y^1$ and $Y^2$ are independently selected from the group consisting of amide, disulfide, thioether, imines, ethers and alkenes.

Other more preferred bicyclic analogs differ from Formulae XVII and XVIII by the replacement of the amino acids at positions 6 and 11 by cysteines which form a disulfide bond, leaving only one backbone cyclization in the Formulae XIX (a and b) and XX (a and b):

Formula (XIXa)

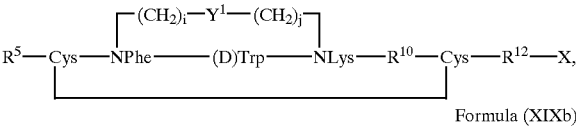

Formula (XIXb)

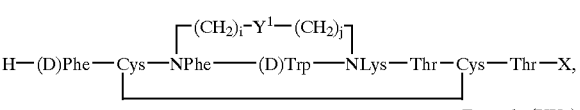

Formula (XXa)

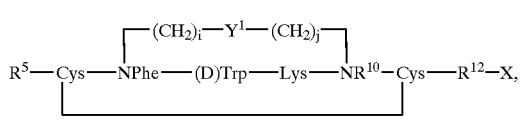

and

-continued

Formula (XXb)

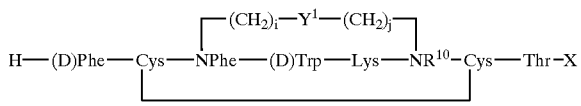

wherein i and j are independently 1, 2 or 3; X is $CH_2OH$ or $NH_2$; $R_5$ is absent or is (D)- or (L)-Phe, Nal, or β-Asp(Ind); $R^6$ and $R^{11}$ are independently Gly or Phe; $R^{10}$ is absent or is Gly, Abu or Thr; $R^{12}$ is absent or is Thr or Nal; and $Y^1$ is selected from the group consisting of amide, disulfide, thioether, imines, ethers and alkenes.

Another aspect of the present invention is a method for the preparation of cyclic peptides of the general Formula (I):

Formula (I)

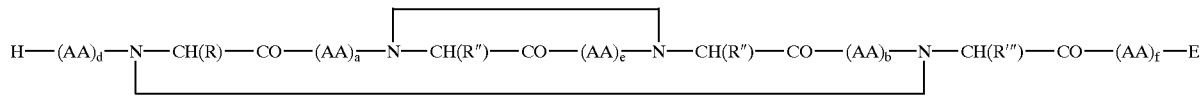

wherein: a and b each independently designates an integer from 1 to 8 or zero; d, e, and f each independently designates an integer from 1 to 10; (AA) designates an amino acid residue wherein the amino acid residues in each chain may be the same or different; E represents a hydroxyl group, a carboxyl protecting group or an amino group, or CO—E can be reduced to $CH_2$—OH; R, R', R", and R''' each designates an amino acid side-chain optionally bound with a specific protecting group; and the lines designate a bridging group of the Formula:

(i) —X—M—Y—W—Z—; or (ii) —X—M—Z— wherein: one line may be absent; M and W are independently selected from the group consisting of disulfide, amide, thioether, thioesters, imines, ethers and alkenes; and X, Y and Z are each independently selected from the group consisting of alkylene, substituted alkylene, arylene, homo- or hetero-cycloalkylene and substituted cycloalkylene. This method comprises the steps of incorporating at least one $N^\alpha$-ω-functionalized derivative of amino acids of Formula (VI):

Formula (VI)

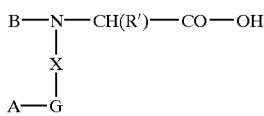

wherein X is a spacer group selected from the group consisting of alkylene, substituted alkylene, arylene, cycloalkylene and substituted cycloalkylene; R' is an amino acid side chain, optionally bound with a specific protecting group; B is a protecting group selected from the group consisting of alkyloxy, substituted alkyloxy, or aryl carbonyls; and G is a functional group selected from the group consisting of amines, thiols, alcohols, carboxylic acids and esters, aldehydes, alcohols and alkyl halides; and A is a specific protecting group of G; into a peptide sequence and subsequently selectively cyclizing the functional group with one of the side chains of the amino acids in said peptide sequence or with another ω-functionalized amino acid derivative.

A further object of the present invention is directed to building units known as a $N^\alpha$-ω-functionalized derivatives of the general Formula (VI) of amino acids which are prerequisites for the cyclization process:

Formula (VI)

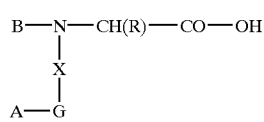

wherein X is a spacer group selected from the group consisting of alkylene, substituted alkylene, arylene, cycloalkylene and substituted cycloalkylene; R is the side chain of an amino acid, optionally bound with a specific protecting group; B is a protecting group selected from the group consisting of alkyloxy, substituted alkyloxy, or aryloxy carbonyls; and G is a functional group selected from the group consisting of amines, thiols, alcohols, carboxylic acids and esters, aldehydes and alkyl halides; and A is a protecting group thereof.

Preferred building units are the ω-functionalized amino acid derivatives wherein X is alkylene; G is a thiol group, an amine group or a carboxyl group; R is phenyl, methyl or isobutyl; with the proviso that when G is an amine group, R is other than H.

Further preferred are ω-functionalized amino acid derivatives wherein R is protected with a specific protecting group.

More preferred are ω-functionalized amino acid derivatives of the Formulae:

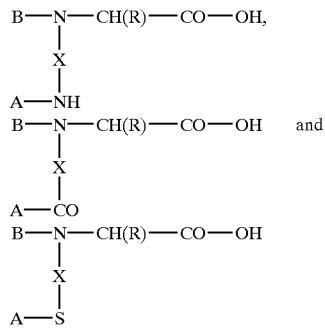

wherein X, R, A and B are as defined above.

Specifically preferred ω-functionalized amino acid derivatives include the following:

1) $N^\alpha$-(Fmoc) (3-Boc-amino propylene)-(S)Phenylalanine;
2) $N^\alpha$-(Fmoc) (3-Boc-amino propylene)-(R)Phenylalanine;
3) $N^\alpha$-(Fmoc) (4-Boc-amino butylene)-(S)Phenylalanine;
4) $N^\alpha$-(Fmoc) (3-Boc-amino propylene)-(S)Alanine;
5) $N^\alpha$-(Fmoc) (6-Boc-amino hexylene)-(S)Alanine;
6) $N^\alpha$-(Fmoc) (3-Boc-amino propylene)-(R)Alanine;
7) $N^\alpha$-(2-(benzylthio)ethylene)glycine ethyl ester;

8) $N^\alpha$-(2-(benzylthio)ethylene)(S)leucine methyl ester;
9) $N^\alpha$-(3-(benzylthio)propylene)(S)leucine methyl ester:
10) Boc-$N^\alpha$-(2-(benzylthio)ethylene)glycine;
11) Boc-$N^\alpha$-(2-(benzylthio)ethylene)(S)phenylalanine;
12) Boc-$N^\alpha$-(3-(benzylthio)propylene)(S)phenylalanine;
13) Boc-L-phenylalanyl-$N^\alpha$-(2-(benzylthio)ethylene) glycine ethyl ester;
14) Boc-L-phenylalanyl-$N^\alpha$-(2-(benzylthio)ethylene)-(S)phenylalanine methyl ester;
15) $N^\alpha$(Fmoc)-(2-t-butyl carboxy ethylene)glycine;
16) $N^\alpha$(Fmoc)-(3-t-butyl carboxy propylene)glycine;
17) $N^\alpha$(Fmoc) (2-t-butyl carboxy ethylene)(S) phenylalanine;
18) $N^\alpha$(Fmoc) (2-Boc amino ethylene)glycine;
19) $N^\alpha$(Fmoc) (3-Boc amino propylene)glycine;
20) $N^\alpha$(Fmoc) (4-Boc amino butylene)glycine; and
21) $N^\alpha$(Fmoc) (6-Boc amino hexylene)glycine.

Novel, practical, generally applicable processes for the preparation of these $N^\alpha$-ω-functionalized derivatives of amino acids are a further aspect of this invention.

As such, an object of this invention is a method of making an ω-functionalized amino acid derivative of the general Formula:

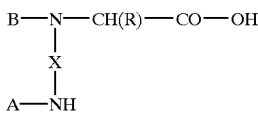

wherein X is a spacer group selected from the group consisting of alkylene, substituted alkylene, arylene, cycloalkylene and substituted cycloalkylene; R is the side chain of an amino acid, such as H, CH₃, etc.; A and B are protecting groups selected from the group consisting of alkyloxy, substituted alkyloxy, or aryloxy carbonyls;

comprising the steps of:

i) reacting a diamine compound of the general Formula:

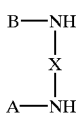

wherein A, B and X are as defined above,
with a triflate of Formula CF₃SO₂—O—CH(R)—CO—E wherein E is a carboxyl protecting group and R is as defined above; to yield a compound of Formula:

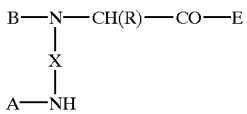

wherein A, B, E, R and X are as defined above
ii) and deprotecting the carboxyl to yield an $N^\alpha$ ω-functionalized amino acid derivative, wherein the ω-functional group is an amine.

A further object of this invention is a method of making an ω-functionalized amino acid derivative of the general Formula:

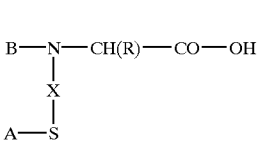

where B is a protecting group selected from the group of substituted alkyloxy, substituted alkyloxy, or aryloxy carbonyls; R is the side chain of an amino acid, such as H, CH₃, etc.; X is a spacer group selected from the group of alkylene, substituted alkylene, arylene, cycloalkylene or substituted cycloalkylene; and A is a protecting group selected from the group of alkyl or substituted alkyl, thio ethers or aryl or substituted aryl thio ethers;

comprising the steps of:

i) reacting a compound of the general Formula B—NH—X—S—A with a triflate of the general Formula CF₃SO₂—O—CH(R)—CO—E wherein E is a carboxyl protecting group and A, X and R are as defined above, to give a compound of the Formula:

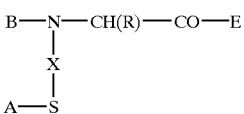

ii) selectively removing the protecting group E, and
iii) protecting the free amino group to yield an $N^\alpha$(ω-functionalized) amino acid derivative, wherein the ω-functional group is a thiol.

A further object of this invention is a method of making an ω-functionalized amino acid derivative of the general Formula:

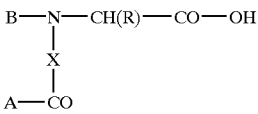

where B is a protecting group selected from the group of alkyloxy, substituted alkyloxy, or aryloxy carbonyls; R is the side chain of an amino acid, such as H, CH₃, etc.; X is a spacer group selected from the group of alkylene, substituted alkylene, arylene, cycloalkylene or substituted cycloalkylene; and A is a protecting group selected from the group of alkyl or substituted alkyl, esters, or thio esters or substituted aryl esters or thio esters;

comprising the steps of:

i) reacting a compound of the general Formula B—NH—X—CO—A with a triflate of the general Formula CF₃SO₂—O—CH(R)—CO—E wherein E is a carboxyl protecting group and A, B, X and R are as defined above, to give a compound of Formula:

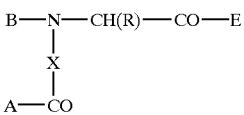

ii) and selectively removing protecting group E, to yield an $N^\alpha$(ω-functionalized) amino acid derivative, wherein the ω-functional group is a carboxyl.

A further aspect of this invention is to provide methods for the preparation of novel backbone cyclic peptides, comprising the steps of incorporating at least one $N^\alpha$-$\omega$-functionalized derivatives of amino acids into a peptide sequence and subsequently selectively cyclizing the functional group with one of the side chains of the amino acids in said peptide sequence, or with another $\omega$-functionalized amino acid derivative.

Backbone cyclized analogs of the present invention may be used as pharmaceutical compositions and for methods for the treatment of disorders including: acute asthma, septic shock, brain trauma and other traumatic injury, post-surgical pain, all types of inflammation, cancers, endocrine disorders and gastrointestinal disorders.

Therefore, further objects of the present invention are directed to pharmaceutical compositions comprising pharmacologically active backbone cyclized peptide agonists and antagonists prepared according to the methods disclosed herein and a pharmaceutically acceptable carrier or diluent; and methods for the treatment of inflammation, septic shock, cancer or endocrine disorders and gastrointestinal disorders therewith.

DETAILED DESCRIPTION OF THE INVENTION

Definitions

Figure 1:
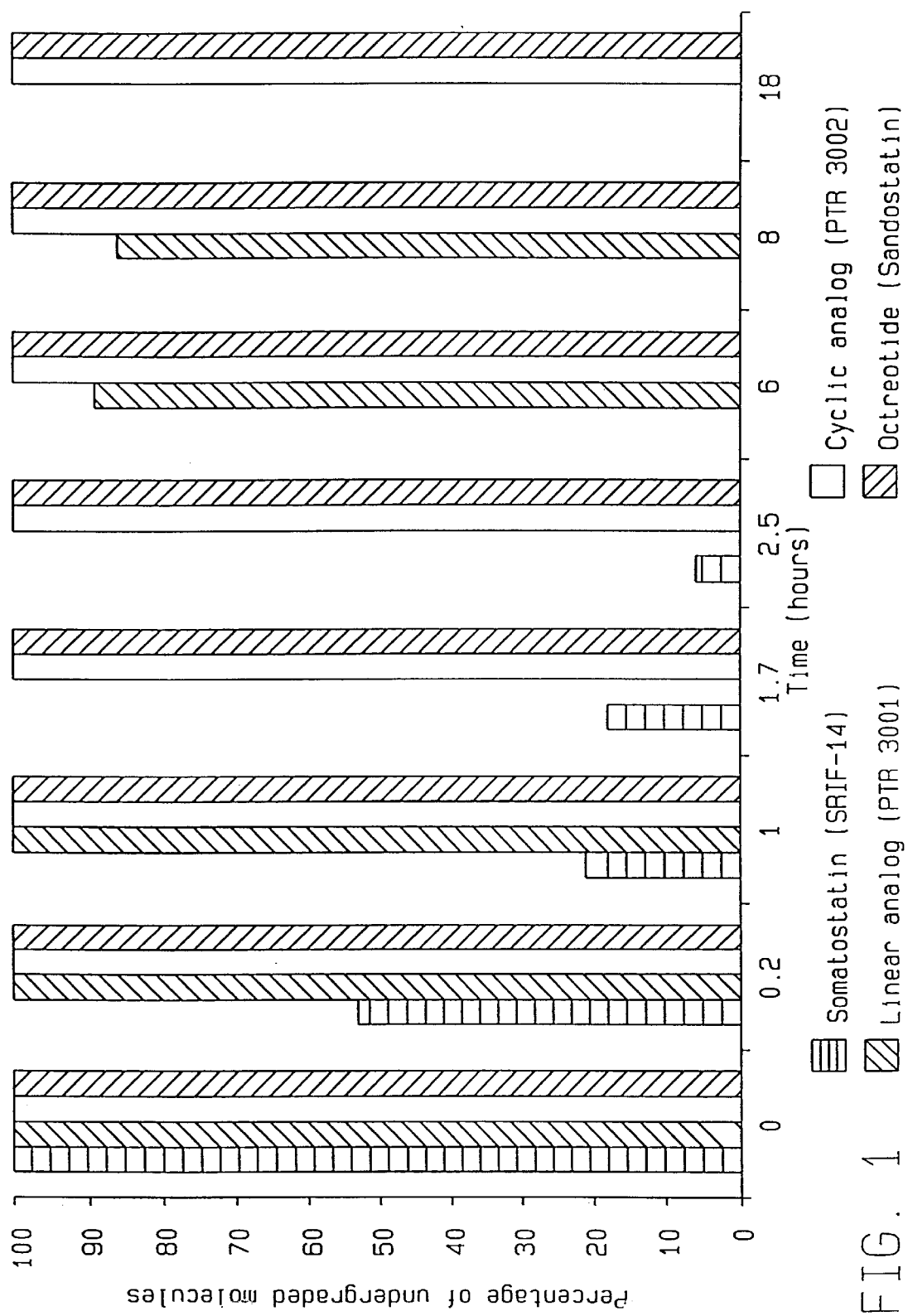
FIG. 1 is a graph showing in vitro biostability of somatostatin and three analogs thereof in human serum. The graph depicts the percentage of undegraded molecules for each of the compounds initially and after various periods of time.

All abbreviations used are in accordance with the IUPAC-IUB recommendations on Biochemical Nomenclature (*J. Biol. Chem.*, 247:977–983, 1972) and later supplements.

As used herein and in the claims, the phrase "an amino acid side chain" refers to the distinguishing substituent attached to the $\alpha$-carbon of an amino acid; such distinguishing groups are well known to those skilled in the art. For instance, for the amino acid glycine, the R group is H; for the amino acid alanine, R is $CH_3$, and so on. Other typical side chains of amino acids include the groups: $(CH_3)_2CH-$, $(CH_3)_2CHCH_2-$, $CH_3CH_2CH(CH_3)-$, $CH_3S(CH_2)_2-$, $HOCH_2-$, $CH_3CH(OH)-$, $HSCH_2-$, $NH_2C(=O)CH_2-$, $NH_2C(=O)(CH_2)_2-$, $NH_2(CH_2)_3-$, $HOC(=O)CH_2-$, $HOC(=O)(CH_2)_2-$, $NH_2(CH_2)_4-$, $C(NH_2)_2NH(CH_2)_3-$, HO-phenyl-$CH_2-$, benzyl, methylindole, and methylimidazole.

As used herein and in the claims, the letters "(AA)" and the term "amino acid" are intended to include common natural for synthetic amino acids, and common derivatives thereof, known to those skilled in the art, including but not limited to the following. Typical amino-acid symbols denote the L configuration unless otherwise indicated by D appearing before the symbol.

| Abbreviated Designation | Amino Acids |
| --- | --- |
| Abu | α-Amino butyric acid |
| Ala | L-Alanine |
| Arg | L-Arginine |
| Asn | L-Asparagine |
| Asp | L-Aspartic acid |
| βAsp (Ind) | β-Indolinyl aspartic acid |

-continued

| Abbreviated Designation | Amino Acids |
| --- | --- |
| Cys | L-Cysteine |
| Glu | L-Glutamic acid |
| Gln | L-Glutamine |
| Gly | Glycine |
| His | L-Histidine |
| Hyp | trans-4-L-Hydroxy Proline |
| Ile | L-Isoleucine |
| Leu | L-Leucine |
| Lys | L-Lysine |
| Met | L-Methionine |
| Nal | β-Naphthyl alanine |
| Orn | Ornithine |
| Phe | L-Phenylalanine |
| Pro | L-Proline |
| Ser | L-Serine |
| Thr | L-Threonine |
| Trp | L-Tryptophane |
| Tyr | L-Tyrosine |
| Val | L-Valine |

Typical protecting groups, coupling agents, reagents and solvents such as but not limited to those listed below have the following abbreviations as used herein and in the claims. One skill in the art would understand that the compounds listed within each group may be used interchangeably; for instance, a compound listed under "reagents and solvents" may be used as a protecting group, and so on. Further, one skill in the art would know other possible protecting groups, coupling agents and reagents/solvents; these are intended to be within the scope of this invention.

| Abbreviated Designation | |
| --- | --- |
| | Protecting Groups |
| Ada | Adamantane acetyl |
| Alloc | Allyloxycarbonyl |
| Allyl | Allyl ester |
| Boc | tert-butyloxycarbonyl |
| Bzl | Benzyl |
| Fmoc | Fluorenylmethyloxycarbonyl |
| OBzl | Benzyl ester |
| OEt | Ethyl ester |
| OMe | Methyl ester |
| Tos (Tosyl) | p-Toluenesulfonyl |
| Trt | Triphenylmethyl |
| Z | Benzyloxycarbonyl |
| | Coupling Agents |
| BOP | Benzotriazol-1-yloxytris-(dimethyl-amino)phosphonium hexafluorophosphate |
| DIC | Diisopropylcarbodiimide |
| HBTU | 2-(1H-Benzotriazol-1-yl)-1,1,3,3-tetramethyluronium hexafluorophosphate |
| PyBrOP | Bromotripyrrolidinophosphonium hexafluorophosphate |
| PyBOP | Benzotriazol-1-yl-oxy-tris-pyrrolidino-phosphonium hexafluorophosphate |
| TBTU | o-(1,2-dihydro-2-oxo-1-pyridyl)-N,N,N',N'-tetramethyluronium tetrafluoroborate |
| | Reagents and Solvents |
| ACN | Acetonitrile |
| AcOH | Acetic acid |
| Ac$_2$O | Acetic acid anhydride |
| AdacOH | Adamantane acetic acid |

| Abbreviated Designation | |
|---|---|
| Alloc-Cl | Allyloxycarbonyl chloride |
| Boc$_2$O | Di-tert butyl dicarbonate |
| DMA | Dimethylacetamide |
| DMF | N,N-dimethylformamide |
| DIEA | Diisopropylethylamine |
| Et$_3$N | Triethylamine |
| EtOAc | Ethyl acetate |
| FmocOSu | 9-fluorenylmethyloxy carbonyl N-hydroxysuccinimide ester |
| HOBT | 1-Hydroxybenzotriazole |
| HF | Hydrofluoric acid |
| MeOH | Methanol |
| Mes (Mesyl) | Methanesulfonyl |
| NMP | 1-methyl-2-pyrrolidinone |
| nin. | Ninhydrin |
| i-PrOH | Iso-propanol |
| Pip | Piperidine |
| PP | 4-pyrrolidinopyridine |
| Pyr | Pyridine |
| SRIF | Somatotropin release inhibiting factor |
| SST | Somatostatin |
| SSTR | Somatostatin receptor |
| TEA | Triethylamine |
| TFA | Trifluoroacetic acid |
| THF | Tetrahydrofuran |
| Triflate (Trf) | Trifluoromethanesulfonyl |
| Trf$_2$O | Trifluoromethanesulfonic acid anhydride |

The compounds herein described may have asymmetric centers. All chiral, diastereomeric, and racemic forms are included in the present invention. Many geometric isomers of olefins and the like can also be present in the compounds described herein, and all such stable isomers are contemplated in the present invention.

By "stable compound" or "stable structure" is meant herein a compound that is sufficiently robust to survive isolation to a useful degree of purity from a reaction mixture, and Formulation into an efficacious therapeutic agent.

As used herein and in the claims, "alkyl" or "alkylenyl" is intended to include both branched and straight-chain saturated aliphatic hydrocarbon groups having one to ten carbon atoms; "alkenyl" is intended to include hydrocarbon chains of either a straight or branched configuration and one or more unsaturated carbon-carbon bonds which may occur in any stable point along the chain, such as ethenyl, propenyl, and the like; and "alkynyl" is intended to include hydrocarbon chains of either a straight or branched configuration and one or more triple carbon-carbon bonds which may occur in any stable point along the chain, such as ethynyl, propynyl, and the like.

As used herein and in the claims, "aryl" is intended to mean any stable 5- to 7-membered monocyclic or bicyclic or 7- to 14-membered bicyclic or tricyclic carbon ring, any of which may be saturated, partially unsaturated or aromatic, for example, phenyl, naphthyl, indanyl, or tetrahydronaphthyl tetralin, etc.

As used herein and in the claims, "alkyl halide" is intended to include both branched and straight-chain saturated aliphatic hydrocarbon groups having one to ten carbon atoms, wherein 1 to 3 hydrogen atoms have been replaced by a halogen atom such as Cl, F, Br, and I.

As used herein and in the claims, the term "heterocyclic" is intended to mean any stable 5- to 7-membered monocyclic or bicyclic or 7- to 10-membered bicyclic heterocyclic ring, which is either saturated or unsaturated, and which consists of carbon atoms and from 1 to 3 heteroatoms selected from the group consisting of N, O and S and wherein the nitrogen and sulfur atoms may optionally be oxidized, and the nitrogen atom optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, piperidonyl, pyrrolidinyl, pyrrolinyl, tetrahydrofuranyl, tetrahydroquinolinyl, tetrahydroisoquinolinyl, decahydroquinolinyl, or octahydroisoquinolinyl and the like.

As used herein and in the claims, the phrase "therapeutically effective amount" means that amount of novel backbone cyclized peptide analog or composition comprising same to administer to a host to achieve the desired results for the indications described herein, such as but not limited of inflammation, septic shock, cancer, endocrine disorders and gastrointestinal disorders.

The term, "substituted" as used herein and in the claims, means that any one or more hydrogen atoms on the designated atom is replaced with a selection from the indicated group, provided that the designated atom's normal valency is not exceeded, and that the substitution results in a stable compound.

When any variable (for example R, x, z, etc.) occurs more than one time in any constituent or in Formulae (I to XX) or any other Formula herein, its definition on each occurrence is independent of its definition at every other occurrence. Also, combinations of substituents and/or variables are permissible only if such combinations result in stable compounds.

Synthetic Approach

According to the present invention peptide analogs are cyclized via bridging groups attached to the alpha nitrogens of amino acids that permit novel non-peptidic linkages. In general, the procedures utilized to construct such peptide analogs from their building units rely on the known principles of peptide synthesis; most conveniently, the procedures can be performed according to the known principles of solid phase peptide synthesis. The innovation requires replacement of one or more of the amino acids in a peptide sequence by novel building units of the general Formula:

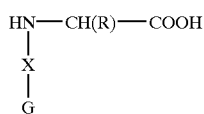

wherein R is the side chain of an amino acid, X is a spacer group and G is the functional end group by means of which cyclization will be effected. The side chain R is the side chain of any natural or synthetic amino acid that is selected to be incorporated into the peptide sequence of choice. X is a spacer group that is selected to provide a greater or lesser degree of flexibility in order to achieve the appropriate conformational constraints of the peptide analog. Such spacer groups include alkylene chains, substituted, branched and unsaturated alkylenes, arylenes, cycloalkylenes, unsaturated and substituted cycloakylenes. Furthermore, X and R can be combined to form a heterocyclic structure.

A preferred embodiment of the present invention utilizes alkylene chains containing from two to ten carbon atoms.

The terminal (ω) functional groups to be used for cyclization of the peptide analog include but are not limited to:
a. Amines, for reaction with electrophiles such as activated carboxyl groups, aldehydes and ketones (with or without subsequent reduction), and alkyl or substituted alkyl halides.

b. Alcohols, for reaction with electrophiles such as activated carboxyl groups.
c. Thiols, for the formation of disulfide bonds and reaction with electrophiles such as activated carboxyl groups, and alkyl or substituted alkyl halides.
d. 1,2 and 1,3 Diols, for the formation of acetals and ketals.
e. Alkynes or Substituted Alkynes, for reaction with nucleophiles such as amines, thiols or carbanions; free radicals; electrophiles such as aldehydes and ketones, and alkyl or substituted alkyl halides; or organometallic complexes.
f. Carboxylic Acids and Esters, for reaction with nucleophiles (with or without prior activation), such as amines, alcohols, and thiols.
g. Alkyl or Substituted Alkyl Halides or Esters, for reaction with nucleophiles such as amines, alcohols, thiols, and carbanions (from active methylene groups such as acetoacetates or malonates); and formation of free radicals for subsequent reaction with alkenes or substituted alkenes, and alkynes or substituted alkynes.
h. Alkyl or Aryl Aldehydes and Ketones for reaction with nucleophiles such as amines (with or without subsequent reduction), carbanions (from active methylene groups such as acetoacetates or malonates), diols (for the formation of acetals and ketals).
i. Alkenes or Substituted Alkenes, for reaction with nucleophiles such as amines, thiols, carbanions, free radicals, or organometallic complexes.
j. Active Methylene Groups, such as malonate esters, acetoacetate esters, and others for reaction with electrophiles such as aldehydes and ketones, alkyl or substituted alkyl halides.

It will be appreciated that during synthesis of the peptide these reactive end groups, as well as any reactive side chains, must be protected by suitable protecting groups. Suitable protecting groups for amines are alkyloxy, substituted alkyloxy, and aryloxy carbonyls including, but not limited to, tert butyloxycarbonyl (Boc), Fluorenylmethyloxycarbonyl (Fmoc), Allyloxycarbonyl (Alloc) and Benzyloxycarbonyl (Z).

Carboxylic end groups for cyclizations may be protected as their alkyl or substituted alkyl esters or thio esters or aryl or substituted aryl esters or thio esters. Examples include but are not limited to tertiary butyl ester, allyl ester, benzyl ester, 2-(trimethylsilyl)ethyl ester and 9-methyl fluorenyl.

Thiol groups for cyclizations may be protected as their alkyl or substituted alkyl thio ethers or disulfides or aryl or substituted aryl thio ethers or disulfides. Examples of such groups include but are not limited to tertiary butyl, trityl (triphenylmethyl), benzyl, 2-(trimethylsilyl)ethyl, pixyl(9-phenylxanthen-9-yl), acetamidomethyl, carboxy-methyl, 2-thio-4-nitropyridyl.

It will further be appreciated by the artisan that the various reactive moieties will be protected by different protecting groups to allow their selective removal. Thus, a particular amino acid will be coupled to its neighbor in the peptide sequence when the $N^\alpha$ is protected by, for instance, protecting group A. If an amine is to be used as an end group for cyclization in the reaction scheme the $N^\omega$ will be protected by protecting group B, or an $\epsilon$ amino group of any lysine in the sequence will be protected by protecting group C, and so on.

The coupling of the amino acids to one another is performed as a series of reactions as is known in the art of peptide synthesis. Novel building units of the invention, namely the $N^\alpha$-$\omega$ functionalized amino acid derivatives are incorporated into the peptide sequence to replace one or more of the amino acids. If only one such $N^\alpha$-$\omega$ functionalized amino acid derivative is selected, it will be cyclized to a side chain of another amino acid in the sequence. For instance: (a) an $N^\alpha$-($\omega$-amino alkylene) amino acid can be linked to the carboxyl group of an aspartic or glutamic acid residue; (b) an $N^\alpha$-($\omega$-carboxylic alkylene) amino acid can be linked to the $\epsilon$-amino group of a lysine residue; (c) an $N^\alpha$-($\omega$-thio alkylene) amino acid can be linked to the thiol group of a cysteine residue; and so on. A more preferred embodiment of the invention incorporates two such $N^\alpha$-$\omega$-functionalized amino acid derivatives which may be linked to one another to form N-backbone to N-backbone cyclic peptide analogs. Three or more such building units can be incorporated into a peptide sequence to create bi-cyclic peptide analogs as will be elaborated below. Thus, peptide analogs can be constructed with two or more cyclizations, including N-backbone to N-backbone, as well as backbone to side-chain or any other peptide cyclization.

As stated above, the procedures utilized to construct peptide analogs of the present invention from novel building units generally rely on the known principles of peptide synthesis. However, it will be appreciated that accommodation of the procedures to the bulkier building units of the present invention may be required. Coupling of the amino acids in solid phase peptide chemistry can be achieved by means of a coupling agent such as but not limited to dicyclohexycarbodiimide (DCC), bis(2-oxo-3-oxazolidinyl) phosphinic chloride (BOP-Cl), benzotriazolyl-N-oxytrisdimethyl-aminophosphonium hexafluoro phosphate (BOP), 1-oxo-1-chlorophospholane (Cpt-Cl), hydroxybenzotriazole (HOBT), or mixtures thereof.

It has now been found that coupling of the bulky building units of the present invention may require the use of additional coupling reagents including, but not limited to: coupling reagents such as PyBOP® (Benzotriazole-1-yl-oxy-tris-pyrrolidino-phosphonium hexafluorophosphate), PyBrOP® (Bromo-tris-pyrrolidino-phosphonium hexafluoro-phosphate), HBTU (2-(1H-Benzotriazole-1-yl)-1,1,3,3-tetramethyluronium hexafluoro-phosphate), TBTU (2-(1H-Benzotriazole-1-yl)-1,1,3,3-tetramethyluronium tetrafluoroborate).

Novel coupling chemistries may be used, such as pre-formed urethane-protected N-carboxy anhydrides (UNCA's) and pre-formed acyl fluorides. Said coupling may take place at room temperature and also at elevated temperatures, in solvents such as toluene, DCM (dichloromethane), DMF (dimethylformamide), DMA (dimethylacetamide), NMP (N-methyl pyrrolidinone) or mixtures of the above.

One object of the present invention is a method for the preparation of backbone cyclized peptide analogs of Formula Formula (I)

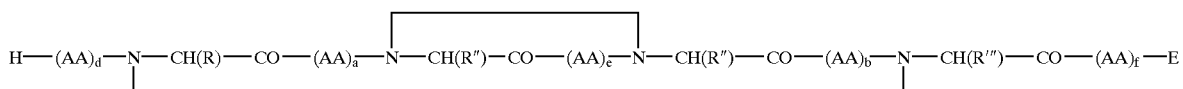

wherein the substituents are as defined above;
comprising the steps of incorporating at least one N<sup>α</sup>-ω-functionalized derivatives of amino acids of Formula (VI):

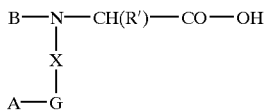
Formula (VI)

wherein X is a spacer group selected from the group consisting of alkylene, substituted alkylene, arylene, cycloalkylene and substituted cycloalkylene; R' is an amino acid side chain such as H, CH$_3$, etc., optionally bound with a specific protecting group; B is a protecting group selected from the group consisting of alkyloxy, substituted alkyloxy, or aryloxy carbonyls; and G is a functional group selected from the group consisting of amines, thiols, alcohols, carboxylic acids and esters, aldehydes, alcohols and alkyl halides; and A is a specific protecting group of G;
with a compound of the Formula (VII):

H$_2$N—(AA)$_f$—CO—E  Formula (VII)

wherein f is an integer from 1 to 10; (AA) designates an amino acid residue wherein the amino acid residues may be the same or different, and E is a hydroxyl, a carboxyl protecting group or an amide to give a compound of the general Formula:

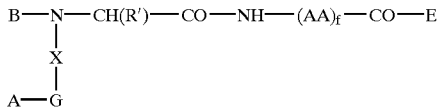
Formula (VIII)

(ii) selectively removing protecting group B and reacting the unprotected compound with a compound of Formula:

B—NH—(AA)$_e$—COOH  Formula (IX)

wherein B and (AA) are as described above and e is an integer from 1 to 10, to give a compound of Formula:

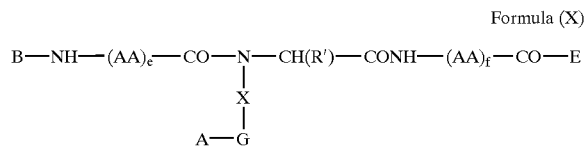
Formula (X)

wherein B, (AA), e, R$^1$, and f are as described above;

(iii) removing the protecting group B from the compound of the Formula (X) and reacting the unprotected compound with a compound of Formula:

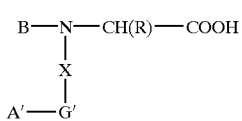
Formula (VIa)

wherein X' is a spacer group selected from the group consisting of alkylenes, substituted alkylenes, arylenes, cycloalkylenes and substituted alkylenes; G' is a functional group selected from amines, thiols, carboxyls, aldehydes or alcohols; A' is a specific-protecting group thereof; R$^1$ is an amino acid side chain such as H, CH$_3$, etc., optionally bound with a specific protecting group; and B is a protecting group;

to yield a compound of Formula:

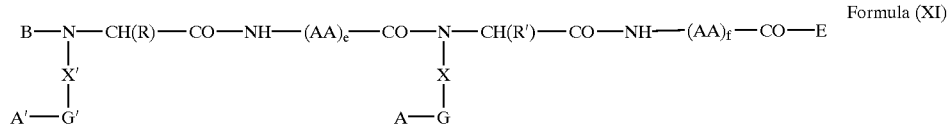
Formula (XI)

(iv) removing the protecting group B and reacting the unprotected compound with a compound of Formula:

B—NH—(AA)$_d$—COOH  Formula (IXa)

to yield a compound of Formula:

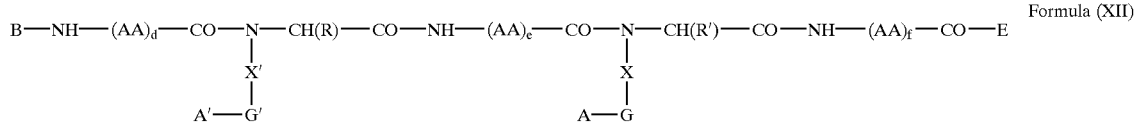
Formula (XII)

(v) selectively removing protecting groups A and A' and reacting the terminal groups G and G' to form a compound of the Formula:

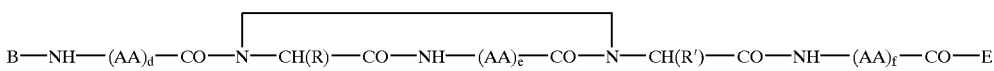

Formula (XIII)

wherein d, e and f are independently an integer from 1 to 10; (AA) is an amino acid residue wherein the amino acid residues in each chain may be the same or different; E is an hydroxyl group, a carboxyl protecting group or an amino group; R and R' are independently an amino acid side-chain such as H, $CH_3$, etc.; and the line designates a bridging group of the Formula: —X—M—Y—W—Z— wherein M and W are independently selected from the group consisting of disulfide, amide, thioether, imine, ether, and alkene; X, Y and Z are independently selected from the group consisting of alkylene, substituted alkylene, arylene, cycloalkylene, and substituted cycloalkylene;

(vi) removing all remaining protecting groups to yield a compound of Formula (I).

Bicyclic analogs are prepared in the same manner, that is, by repetition of steps (v) and (vi). The determination of which residues are cyclized with which other residues is made through the choice of blocking groups. The various blocking groups may be removed selectively, thereby exposing the selected reactive groups for cyclization.

Preferred are methods for the preparation of backbone cyclized peptide analogs of Formula (I) wherein G is an amine, thiol or carboxyl group; R and $R^1$ are each other than H, such as $CH_3$, $(CH_3)_2CH—$, $(CH_3)_2CHCH_2—$, $CH_3CH_2CH(CH_3)—$, $CH_3S(CH_2)_2—$, $HOCH_2—$, $CH_3CH(OH)—$, $HSCH_2—$, $NH_2C(=O)CH_2—$, $NH_2C(=O)(CH_2)_2—$, $HOC(=O)CH_2—$, $HOC(=O)(CH_2)_2—$, $NH_2(CH_2)_4—$, $C(NH_2)_2NH(CH_2)_3—$, HO-phenyl-$CH_2—$, benzyl, methylindole, and methylimidazole, and wherein E is covalently bound to an insoluble polymeric support.

Another object of the present invention is a method for the preparation of backbone cyclized peptide analogs of Formula (II):

Formula (II)

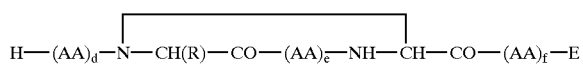

wherein the substituents are as defined above;
comprising the steps of: incorporating at least one ω-functionalized amino acid derivative of the general Formula (VI):

Formula (VI)

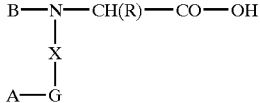

wherein X is a spacer group selected from the group consisting of alkylene, substituted alkylene, arylene, cycloalkylene and substituted cycloalkylene; R is the side chain of an amino acid, such as H, $CH_3$, etc.; B is a protecting group selected from the group consisting of alkyloxy, substituted alkyloxy, or aryloxy carbonyls; and G is a functional group selected from the group consisting of amines, thiols, alcohols, carboxylic acids and esters or alkyl halides and A is a protecting group thereof;

into a peptide sequence and subsequently selectively cyclizing the functional group with one of the side chains of the amino acids in said peptide sequence.

Preferred is the method for the preparation of backbone cyclized peptide analogs of Formula (II) wherein G is a carboxyl group or a thiol group; R is $CH_3$, $(CH_3)_2CH—$, $(CH_3)_2CHCH_2—$, $CH_3CH_2CH(CH_3)—$, $CH_3S(CH_2)_2—$, $HOCH_2—$, $CH_3CH(OH)—$, $HSCH_2—$, $NH_2C(=O)CH_2—$, $NH_2C(=O)(CH_2)_2—$, $HOC(=O)CH_2—$, $HOC(=O)(CH_2)_2—$, $NH_2(CH_2)_4—$, $C(NH_2)_2NH(CH_2)_3—$, HO-phenyl-$CH_2—$, benzyl, methylindole, and methylimidazole, and wherein E is covalently bound to an insoluble polymeric support.

Preparation of backbone to side chain cyclized peptide analogs is exemplified in Scheme I below. In this schematic example, the bridging group consists of alkylene spacers and an amide bond formed between an acidic amino acid side chain (e.g. aspartic or glutamic acid) and an ω-functionalized amino acid having a terminal amine.

(Scheme I)
Preparation of Peptides with Backbone to Side Chain Cyclization

One preferred procedure for preparing the desired backbone cyclic peptides involves the stepwise synthesis of the linear peptides on a solid support and the backbone cyclization of the peptide either on the solid support or after removal from the support. The C-terminal amino acid is bound covalently to an insoluble polymeric support by a carboxylic acid ester or other linkages such as amides. An example of such support is a polystyrene-co-divinyl benzene resin. The polymeric supports used are those compatible with such chemistries as Fmoc and Boc and include for example PAM resin, HMP resin and chloromethylated resin. The resin bound amino acid is deprotected for example with TFA to give (1) below and to it is coupled the second amino acid, protected on the $N^\alpha$ for example by Fmoc, using a coupling reagent like BOP. The second amino acid is deprotected to give (3) using for example piperidine 20% in DMF. The subsequent protected amino acids can then be coupled and deprotected at ambient temperature. After several cycles of coupling and deprotection that gives peptide (4), an amino acid having for example carboxy side chain is coupled to the desired peptide. One such amino acid is Fmoc-aspartic acid t-butyl ester. After deprotection of the $N^\alpha$ Fmoc protecting group that gives peptide (5), the peptide is again elongated by methods well known in the art to give (6). After deprotection a building unit for backbone cyclization (the preparation of which is described in Schemes III-VIII) is coupled to the peptide resin using for example the coupling reagent BOP to give (7). One such building unit is for example Fmoc-$N^\alpha$(ω-Boc-amino alkylene)amino acid. After deprotection the peptide can then be elongated, to the desired length using methods well known in the art to give (8). The coupling of the protected amino acid subsequent to the building unit is performed by such coupling agents exemplified by PyBrOP® to ensure high yield.

After the linear, resin bound peptide, e.g. (8), has been prepared the ω-alkylene-protecting groups for example Boc and t-Bu are removed by mild acid such as TFA to give (9). The resin bound peptide is then divided into several parts. One part is subjected to on-resin cyclization using for example TBTU as cyclization agent in DMF to ensure high yield of cyclization, to give the N-backbone to side chain cyclic peptide resin (10). After cyclization on the resin the terminal amino protecting group is removed by agents such as piperidine and the backbone to side chain cyclic peptide (11) is obtained after treatment with strong acid such as HF. Alternatively, prior to the removal of the backbone cyclic peptide from the resin, the terminal amino group is blocked by acylation with agents such as acetic anhydride, benzoic anhydride or any other acid such as adamantyl carboxylic acid activated by coupling agents such as BOP.

The other part of the peptide-resin (9) undergoes protecting of the side chains used for cyclization, for example the ω-amino and carboxy groups. This is done by reacting the ω-amino group with for example $Ac_2O$ and DMAP in DMF and activating the free ω-carboxy group by for example DIC and HOBT to give the active ester which is then reacted with for example $Dh_3NH_2$ to give the linear analog (13) of the cyclic peptide (10). Removal of the peptide from the resin and subsequent removal of the side chains protecting groups by strong acid such as HF to gives (14) which is the linear analog of the backbone to side chain cyclic peptide (11).

The linear analogs are used as reference compounds for the biological activity of their corresponding cyclic compounds.

Reaction Scheme I Follows at this Point

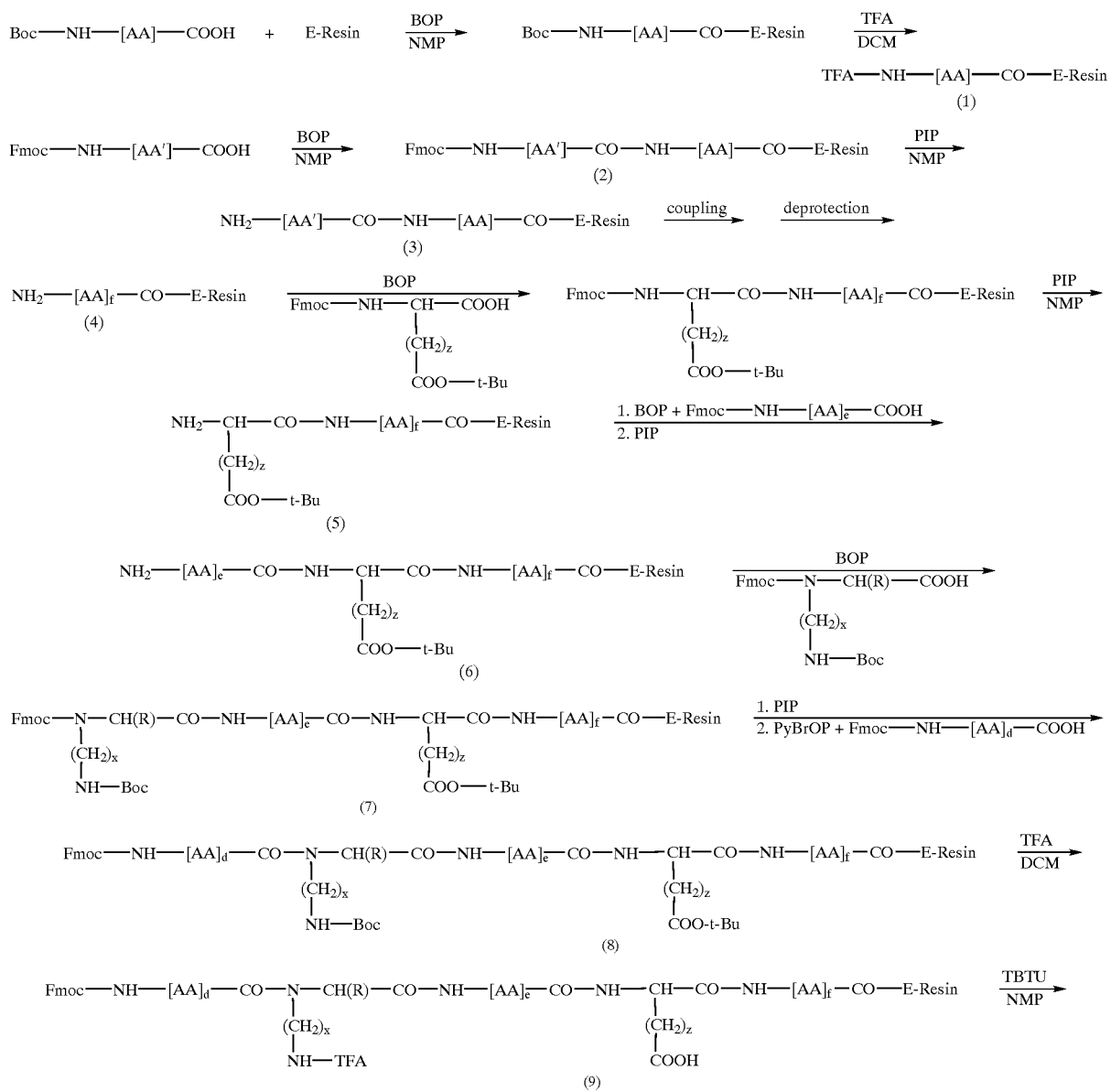

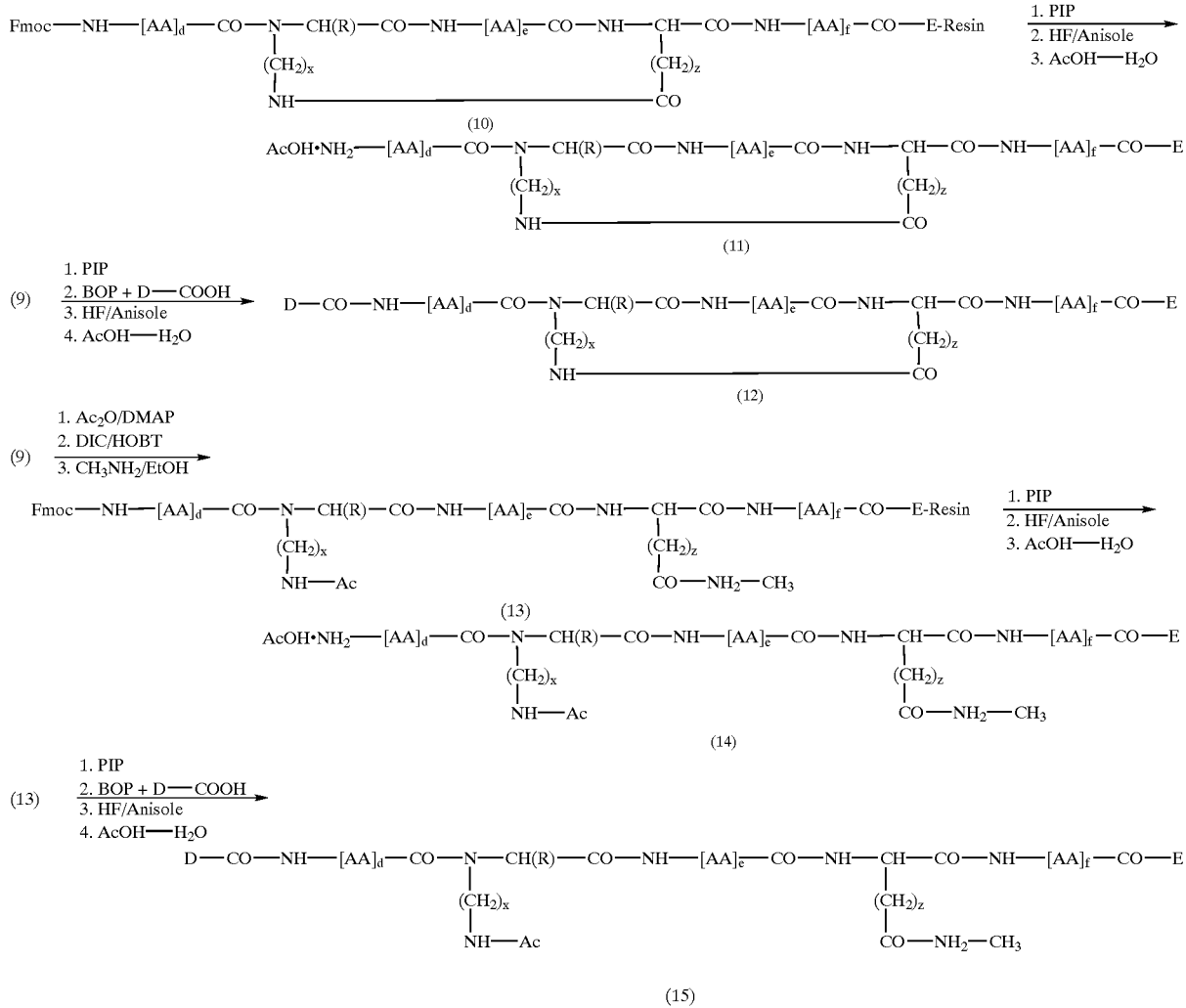

The selection of $N^\alpha$ and side chain protecting groups is, in part, dictated by the cyclization reaction which is done on the peptide-resin and by the procedure of removal of the peptide from the resin. The $N^\alpha$ protecting groups are chosen in such a manner that their removal will not effect the removal of the protecting groups of the $N^\alpha(\omega$-aminoalkylene) protecting groups. In addition, the removal of the $N^\alpha(\omega$-aminoalkylene)protecting groups or any other protecting groups on $\omega$-functional groups prior to the cyclization, will not effect the other side chain protection and/or the removal of the peptide from the resin. The selection of the side chain protecting groups other than those used for cyclization is chosen in such a manner that they can be removed subsequently with the removal of the peptide from the resin. Protecting groups ordinarily employed include those which are well known in the art, for example, urethane protecting substituents such as Fmoc, Boc, Alloc, Z and the like.

It is preferred to utilize Fmoc for protecting the α-amino group of the amino acid undergoing the coupling reaction at the carboxyl end of said amino acid. The Fmoc protecting group is readily removed following such coupling reaction and prior to the subsequent step by the mild action of base such as piperidine in DMF. It is preferred to utilize Boc for protecting ω-amino group of the $N^\alpha(\omega$-aminoalkylene) group and t-Bu for protecting the carboxy group of the amino acids undergoing the reaction of backbone cyclization. The Boc and t-Bu protecting groups are readily removed simultaneously prior to the cyclization.

(Scheme II)

Preparation of Peptides with Backbone to Backbone Cyclization

Preparation of N-backbone to N-backbone cyclized peptide analogs is exemplified in scheme II. In this schematic example, the building group consists of alkylene spacers and two amide bonds.

A building unit for backbone cyclization (the preparation of which described in Schemes III-VIII) is coupled to a peptide resin, for example peptide-resin (4), using for example the coupling reagent BOP to give (16). One such building unit is for example Fmoc-Nα(ω-Boc-amino alkylene)amino acid. The side chain Boc protecting group is removed by mild acid such as TFA in DCM and an N-Boc protected ω-amino acid, or any other Boc protected amino acid, is coupled to the side chain amino group using coupling agent such as BOP to give peptide-resin (17).

After deprotection of the $N^\alpha$ Fmoc protecting group by mild base such as piperidine in DMF, the peptide can then be elongated, if required, to the desired length using methods well known in the art to give (18). Alternatively, the deprotection of the $N^\alpha$ Fmoc and subsequent elongation of the peptide can be done before deprotection of the side chain Boc protecting group. The elongation of the N-alkylene side chain allow control of the ring size. The coupling of the protected amino acid subsequent to the building unit is performed by such coupling agents exemplified by PyBrOP® to ensure high yield. After deprotection of the terminal $N^\alpha$ Fmoc group, a second building unit, for example Fmoc-$N^\alpha$(ω-t-Bu-carboxy-alkylene)amino acid is coupled to the peptide-resin to give (19). After deprotection of the $N^\alpha$ Fmoc protecting group, the peptide can then be elongated, if required, to the desired length using methods well known in the art to give (20). The coupling of the protected amino acid subsequent to the building unit is performed by such coupling agents exemplified by PyBrOP® to ensure high yield. After the linear, resin bound peptide, e.g. (20), has been prepared the ω-alkylene-protecting groups for example Boc and t-Bu are removed by mild acid such as TFA to give (21). The resin peptide is then divided into several parts. One part is subjected to on-resin cyclization using for example TBTU as cyclization agent in DMF to ensure high yield of cyclization, to give the N-backbone to N-backbone cyclic peptide resin (22). After cyclization on the resin the terminal amino protecting group is removed by agents such as piperidine and the backbone to backbone cyclic peptide (23) is obtained after treatment with strong acid such as HF. Alternatively, prior to the removal of the backbone cyclic peptide from the resin, the terminal amino group of (22) is blocked, after deprotection, by acylation with agents such as acetic anhydride, benzoic anhydride or any other acid such as adamantyl carboxylic acid activated by coupling agents such as BOP to give the N-terminal blocked backbone to backbone cyclic peptide (24).

The other part of the peptide-resin (21) undergoes protecting of the side chains used for cyclization, for example the ω-amino and carboxy groups. This is done by reacting the ω-amino group with for example $Ac_2O$ and DMAP in DMF and activating the free ω-carboxy group by for example DIC and HOBT to give the active ester which is then reacted with for example $MeNH_2$. Removal of the peptide from the resin and subsequent removal of the side chains protecting groups by strong acid such as HF to gives (26) which is the linear analog of the backbone to backbone cyclic peptide (23). The linear analogs are used as reference compounds for the biological activity of their corresponding cyclic compounds.

Reaction Scheme II Follows at this Point

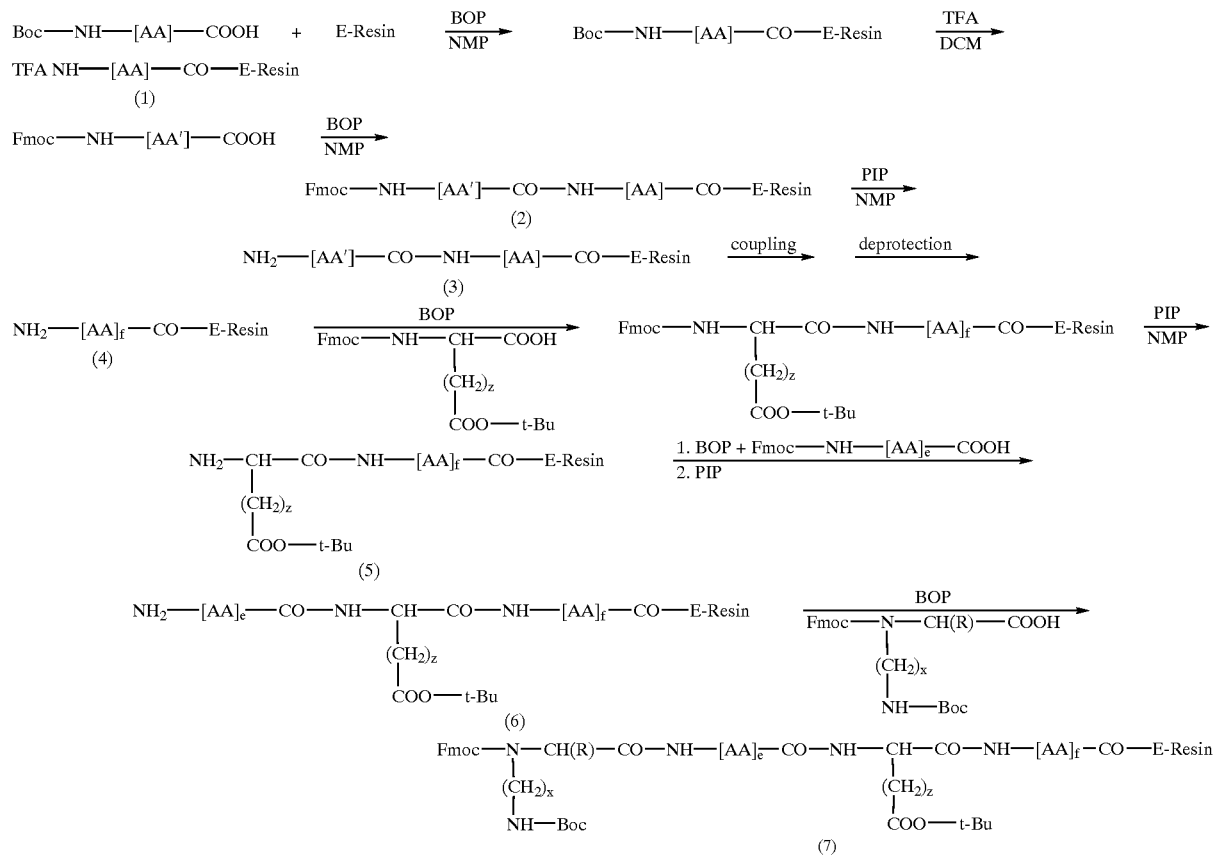

SCHEME II
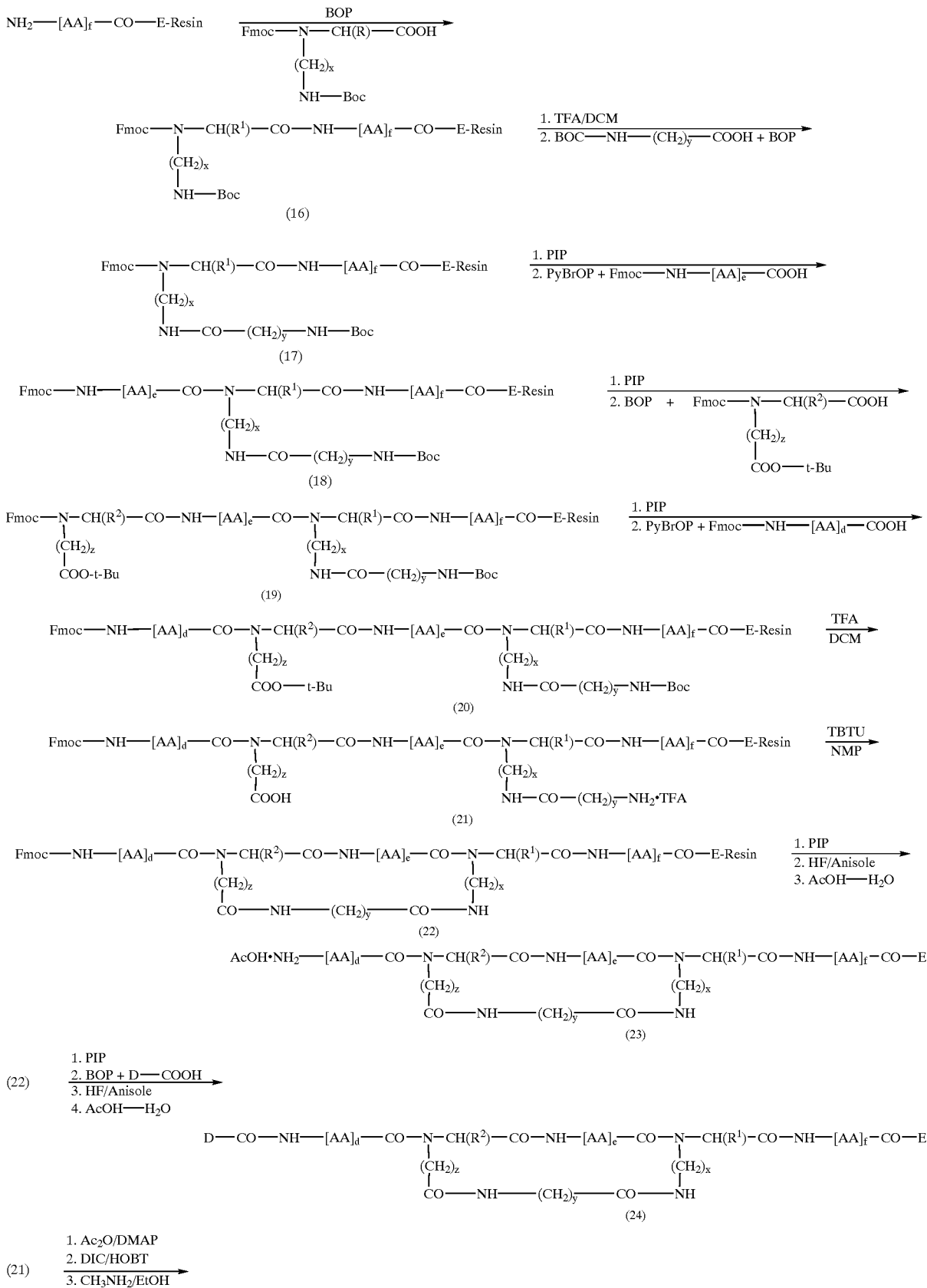

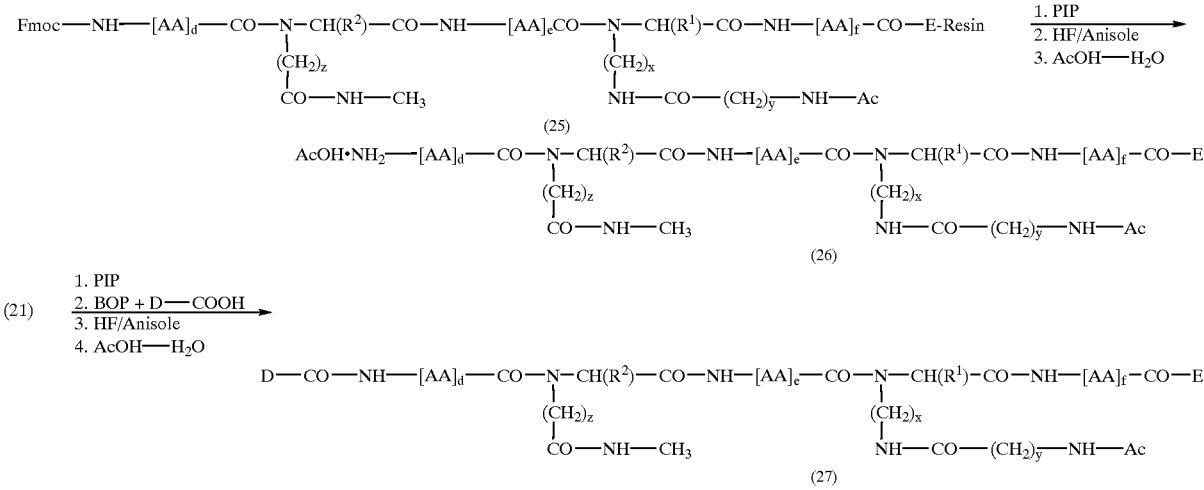

Novel Synthesis of Building Units

The novel synthesis providing N(ω-(functionalized) alkylene) amino acids used to generate backbone cyclic peptides is depicted in schemes III–VIII. In this approach we have implemented the following changes in order to devise a practical, general synthesis:

1. The nucleophile is a secondary nitrogen, which is a better nucleophile than the primary nitrogen previously used. This also prevents the possibility of double alkylation.
2. The leaving group was changed to trifluoromethanesulfonyl (triflate), which has a much lower tendency to eliminate than a halogen, thus making it possible to implement the synthesis with amino acids other than glycine. Furthermore, the triflate leaving group prevents racemization during the alkylation reaction.
3. The carboxylate is esterified prior to the substitution reaction, to facilitate the substitution by removing the negative charge next to the electrophilic carbon.

(Scheme III)
Preparation of $N^\alpha$, $N^\omega$ Protected ω-amino alkylene amino acids Building Units One preferred procedure for the preparation of protected $N^\alpha$(ω-amino alkylene) amino acids involves the $N^\alpha$ alkylation of suitably protected diamino alkanes. One preferred $N^\alpha,N^\omega$ di-protected diamino alkane is for example $N^\alpha$-Benzyl, $N^\omega$-Boc diamino alkane (27). This starting material contains one protecting group such as Boc which is necessary for the final product, and a temporary protecting group such as Bzl to minimize unwanted side reactions during the preparation of the titled compound. One preferred procedure for the preparation of the starting material (27) involves reductive alkylation of N-Boc diamino alkane with aldehydes such as benzaldehyde. The temporary protection of the $N^\alpha$ amino group, which is alkylated in the reaction by such protecting groups as Bzl, minimizes the dialkylation side reaction and allows removal by such conditions that do not remove the $N^\omega$-protecting group.

The $N^\alpha,N^\omega$ di-protected diamino alkane is reacted with for example chiral α-hydroxy α-substituted acid esters where the hydroxyl moiety is converted to a leaving group for example Triflate.

The use of Triflate as the leaving group was found to be superior to other leaving groups such as halogens, Tosyl, Mesyl, etc., because it prevents the β-elimination reaction encountered with the other leaving groups. The use of Triflate as the leaving group also ensures high optical purity of the product (28). The temporary $N^\alpha$ protecting group, such as Bzl, and the carboxyl protecting group, such as methyl ester, are removed by mild conditions, such as catalytic hydrogenation and hydrolysis, that do not remove the $N^\omega$ protecting group such as Boc to give the $N^\omega$ protected amino acid (29). Introduction of the $N^\alpha$ protecting group suitable for peptide synthesis is accomplished by methods well known in the art, to give the protected $N^\alpha(N^\omega$ protected amino alkylene) amino acid (30).

The choice of the $N^\alpha$ and the $N^\omega$ protecting groups is dictated by the use of the building units in peptide synthesis. The protecting groups have to be orthogonal to each other and orthogonal to the other side chains protecting groups in the peptide. Combinations of $N^\alpha$ and $N^\omega$ protecting groups are for example: $N^\alpha$-Fmoc, $N^\omega$-Boc; $N^\alpha$-Fmoc, $N^\omega$-Alloc; $N^\alpha$-Boc, $N^\omega$-Alloc. These combinations are suitable for peptide synthesis and backbone cyclization, either on solid support or in solution.

(Scheme IV)
Preparation of $N^\alpha$, $N^\omega$ Protected ω-amino Alkylene Glycine Building Units One preferred procedure for the preparation of protected $N^\alpha(N^\omega$-amino alkylene) glycines involves the reaction of the $N^\alpha,N^\omega$ di-protected di amino alkane (27) with commercially available α-activated carboxylic acid esters, for example benzylbromo acetate. Since the titled compound is achiral, the use of leaving groups such as Trf, Tos or Mes is not necessary. The use of the same temporary protecting groups for the $N^\alpha$ and the carboxy groups, for example the Bzl protecting group, ensures the prevention of the undesired dialkylation side reaction and allows concomitant removal of the temporary protecting groups thus giving high yield of the $N^\omega$ protected amino acid (32). Introduction of the $N^\alpha$ protecting group suitable for peptide synthesis is accomplished by methods well known in the art, to give the protected $N^\alpha(N^\omega$ protected amino alkylene) glycines (33).

The choice of the $N^\alpha$ and the $N^\omega$ protecting groups is dictated by the use of the building units in peptide synthesis. The protecting groups have to be orthogonal to each other and orthogonal to the other side chains protecting groups in the peptide. Combinations of $N^\alpha$ and $N^\omega$ protecting groups are for example: $N^\alpha$ Fmoc, $N^\omega$ Boc ; $N^\alpha$ Fmoc, $N^\omega$ Alloc; $N^\alpha$ Boc. $N^\omega$ Alloc. These combinations are suitable for peptide synthesis and backbone cyclization, either on solid support or in solution.

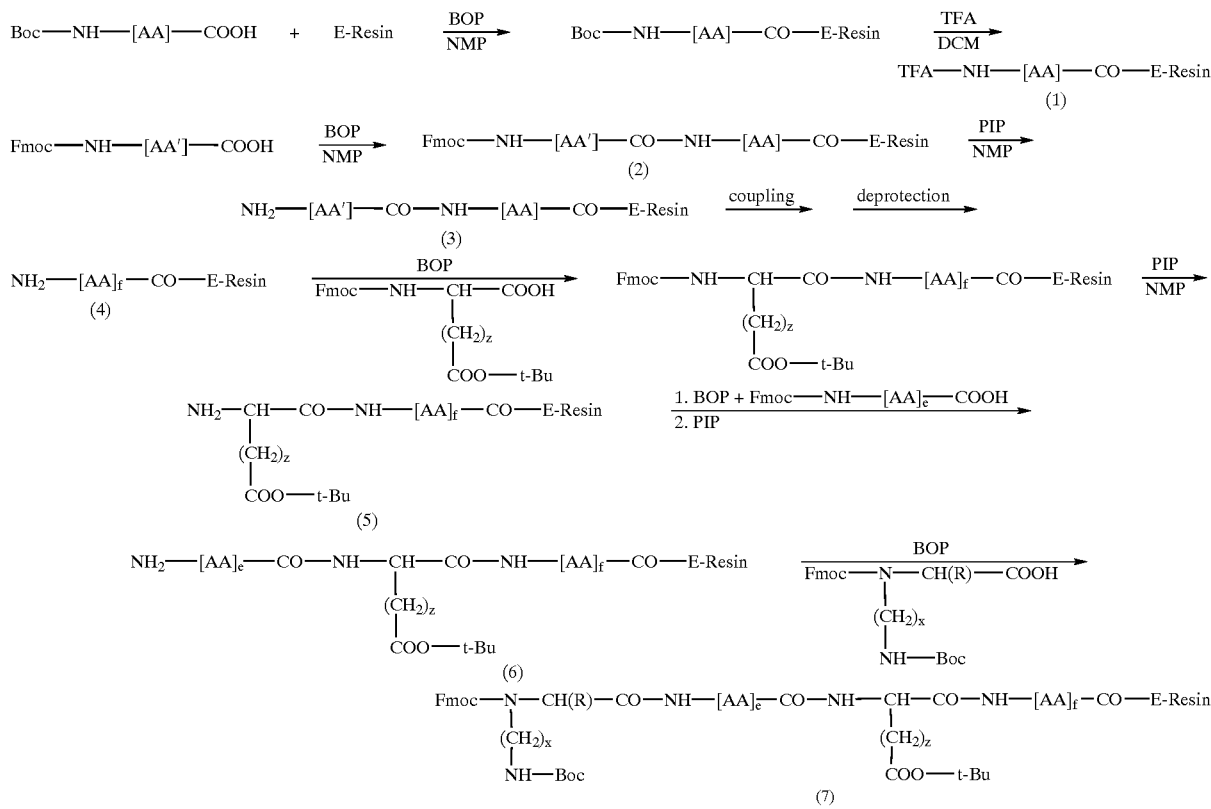
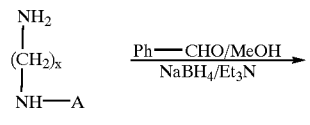
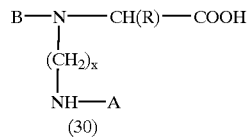
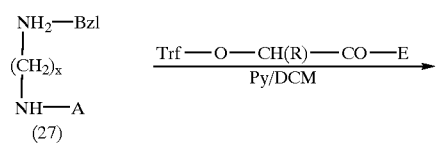
A = for example Boc, Fmoc, Alloc.
B = for example Fmoc, Boc, Alloc.
B—L = for example Fmoc—Osu, Boc$_2$O, Alloc—Cl
E = for example OMe, OEt, OBzl.
x = 1–10
R = amino acid side chains
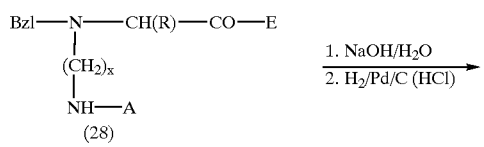
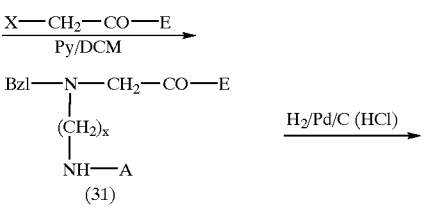
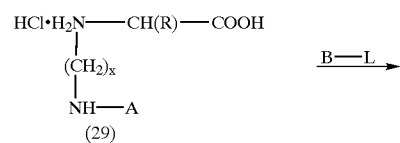
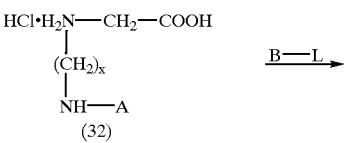

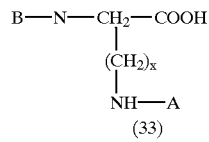

(33)

A = for example Boc, Fmoc, Alloc.
B = for example Fmoc, Boc, Alloc.
B—L = for example Fmoc——Osu, Boc₂O, Alloc——Cl
E = for example OMe, OEt, OBzl.
x = 1–10
X = Cl, Br, I (Scheme V)
Preparation of $N^\alpha$, ω-carboxy Protected w-carboxy alkylene amino acids One preferred procedure for the preparation of protected $N^\alpha$(ω-carboxy alkylene) amino acids involves the $N^\alpha$-alkylation of suitably $N^\alpha$, ω-carboxy deprotected amino acids. One preferred deprotected amino acid is $N^\alpha$-Benzyl ω-amino acids t-butyl esters (34). This starting material contains one protecting group such as t-Bu ester which is necessary for the final product, and a temporary protecting group such as $N^\alpha$ Bzl to minimize side reactions during the preparation of the titled compound. One preferred procedure for the preparation of the starting material (34) involves reductive alkylation of ω-amino acids t-butyl esters with aldehydes such as benzaldehyde. The temporary protection of the amino group which is used as nucleophile in the proceeding alkylation reaction by such protecting groups as Bzl minimizes the dialkylation side reaction.

The $N^\alpha$, ω-carboxy deprotected amino acids (34) are reacted with, for example, chiral α-hydroxy α-substituted acid esters where the hydroxyl moiety is converted to a leaving group, for example, Triflate. The use of Triflate as the leaving group was found to be superior to other leaving groups such as halogens, Tosyl, Mesyl; etc., because it prevents the β-elimination reaction encountered with the other leaving groups. The use of Triflate as the leaving group also ensures high optical purity of the product, for example (36). The temporary $N^\alpha$ protecting group, such as Bzl, and the α-carboxyl protecting group, such as benzyl ester, are concomitantly removed by mild condition, such as catalytic hydrogenation, that to not remove the ω-carboxy protecting group such as t-Bu to give the $N^\alpha$(protected ω-carboxy alkylene) amino acid (36). Introduction of the $N^\alpha$ protecting group suitable for peptide synthesis is accomplished by methods well known in the art, to give the protected $N^\alpha$(ω protected carboxy alkylene) amino acid (37).

The choice of the $N^\alpha$ and the ω-carboxy protecting groups is dictated by the use of the building units in peptide synthesis. The protecting groups have to be orthogonal to each other and orthogonal to the other side chains protecting groups in the peptide. A combination of $N^\alpha$ and ω-carboxy protecting groups are for example: $N^\alpha$-Fmoc, ω-carboxy t-Bu; $N^\alpha$-Fmoc, ω-carboxy Alloc; $N^\alpha$-Boc, ω-carboxy Alloc. These combinations are suitable for peptide synthesis and backbone cyclization, either on solid support or in solution.

(Scheme VI)
Preparation of $N^\alpha$, ω-carboxy Protected ω-carboxy alkylene glycine Building Units One preferred procedure for the preparation of protected $N^\alpha$(ω-carboxy alkylene)glycines involves the $N^\alpha$-alkylation of suitably $N^\alpha$, ω-carboxy deprotected amino acids(34) with commercially available α-activated carboxylic acid esters for example, benzyl bromo acetate. Since the titled compound is achiral, the use of leaving groups such as Trf, Tos or Mes is not necessary.

The use of the same temporary protecting groups for the $N^\alpha$ and the α-carboxy groups, for example the Bzl protecting group, ensures the prevention of the undesired dialkylation side reaction and allows concomitant removal of the temporary protecting groups thus giving high yield of the $N^\alpha$(protected ω-carboxy alkylene) glycines (39). Introduction of the $N^\alpha$ protecting group suitable for peptide synthesis is accomplished by methods well known in the art, to give the protected $N^\alpha$ (ωprotected carboxy alkylene) glycines (40).

The choice of the $N^\alpha$ and the ω-carboxy protecting groups is dictated by the use of the building units in peptide synthesis. The protecting groups have to be orthogonal to each other and orthogonal to the other side chains protecting groups in the peptide. A combination of $N^\alpha$ and ω-carboxy protecting groups are, for example: $N^\alpha$ Fmoc, ω-carboxy t-Bu; $N^\alpha$ Fmoc, ω-carboxy Alloc; $N^\alpha$ Boc, ω-carboxy Alloc. These combinations are suitable for peptide synthesis and backbone cyclization, either on solid support or in solution.

SCHEME V

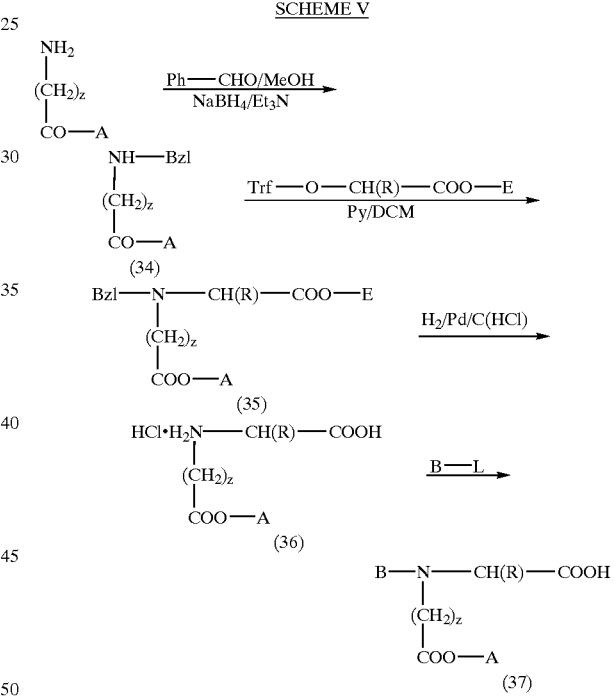

A = for example O——t-Bu,O-All
B = for example Fmoc, Boc
B——L = for example Fmoc——Osu, Boc₂O
E = for example OMe, OEt, OBzl
z = 1–10
R = amino acid side chains

SCHEME VI

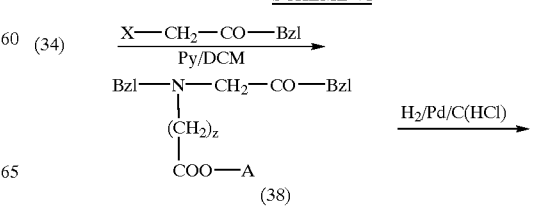

-continued

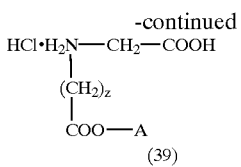

(39)

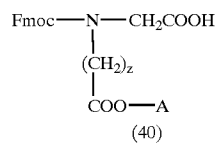

(40)

A = for example O—t-Bu,O-All
B = for example Fmoc, Boc
B—L = for example Fmoc—Osu, Boc$_2$O
E = for example OMe, OEt, OBzl
z = 1–10

(Scheme VII)
Preparation of N$^\alpha$S$^\omega$ protected ω-thio Alkylene Amino Acid Building Units.

One preferred procedure for the preparation of N$^\alpha$,S$^\omega$-deprotected N$^\alpha$(ω-thio alkylene) amino acids involves the N$^\alpha$-alkylation of suitably S$^\omega$ protected ω-thio amino alkanes. Suitable S$^\omega$ protecting groups are, for example, Bzl, t-Bu, Trt. One preferred S$^\omega$-protected ω-thio amino alkanes is for example ω-(S-Benzyl) amino alkanes (41). One preferred procedure for the preparation of the starting material (41) involves the use of salts of S-protected thiols as nucleophiles for a nucleophilic substitution reaction on suitably N$^\alpha$-protected ω-activated amino alkanes. Removal of the amino protection gives the starting material (41).

The S-protected ω-thio amino alkanes (41) are reacted with for example chiral α-hydroxy α-substituted acid esters where the hydroxyl moiety is converted to a leaving group for example Triflate. The use of Triflate as the leaving group was found to be superior to other leaving groups such as halogens, Tosyl, Mesyl etc. because it prevents the β-elimination reaction encountered with the other leaving groups. The use of Triflate as the leaving group also ensures high optical purity of the product for example (42). The temporary α-carboxyl protecting group, such as methyl ester, is removed by mild condition, such as hydrolysis with base, that to not remove the ω-thio protecting group such as S-Bzl to give the N$^\alpha$(S-protected ω-thio alkylene) amino acid (43). Introduction of the N$^\alpha$ protecting group suitable for peptide synthesis is accomplished by methods well known in the art, to give the protected N,S protected N$^\alpha$(ω-thio alkylene) amino acid (44).

The choice of the N$^\alpha$ and the ω-thio protecting groups is dictated by the use of the building units in peptide synthesis. The protecting groups have to be orthogonal to each other and orthogonal to the other side chains protecting groups in the peptide. A combination of N$^\alpha$ and ω-thio protecting groups are for example: N$^\alpha$ Fmoc, S$^\omega$ t-Bu; N$^\alpha$ Fmoc, S$^\omega$ Bzl; N$^\alpha$ Fmoc, S$^\omega$ Trt; N$^\alpha$ Boc, S$^\omega$ Bzl. These combinations are suitable for peptide synthesis and backbone cyclization, either on solid support or in solution.
(Scheme VIII)
Preparation of N$^\alpha$, S$^\omega$ Protected ω-thio alkylene glycine Building Units.

One preferred procedure for the preparation of N$^\alpha$, S$^\omega$-deprotected N$^\alpha$(ω-thio alkylene) amino acids involves the N$^\alpha$-alkylation of suitably S$^\omega$ protected ω-thio amino alkanes (41) with commercially available α-activated carboxylic acid esters for example ethyl bromo acetate. Since the titled compound is achiral, the use of leaving groups such as Trf, Tos or Mes is not necessary.

Suitable protecting groups for the ω-thio groups are for example Bzl, t-Bu, Trt. One preferred S-protected ω-thio amino alkanes is for example ω-(S-Benzyl) amino alkanes (41). The N-alkylation reaction gives the ester (45). The temporary α-carboxyl protecting group, such as ethyl ester, is removed by mild conditions, such as hydrolysis with base, that to not remove the ω-thio protecting group such as S-Bzl to give the N$^\alpha$(S-protected ω-thio alkylene) glycines (46). Introduction of the N$^\alpha$ protecting group suitable for peptide synthesis is accomplished by methods well known in the art, to give the protected N$^\alpha$, S$^\omega$-deprotected N$^\alpha$(ω-thio alkylene) glycines (47).

The choice of the N$^\alpha$ and the ω-thio protecting groups is dictated by the use of the building units in peptide synthesis. The protecting groups have to be orthogonal to each other and orthogonal to the other side chains protecting groups in the peptide. A combination of N$^\alpha$ and ω-thio protecting groups are for example: N$^\alpha$ Fmoc, S$^\omega$ t-Bu; N$^\alpha$ Fmoc, S$^\omega$ Bzl; N$^\alpha$ Fmoc, S$^\omega$ Trt; N$^\alpha$ Boc, S$^\omega$ Bzl. These combinations are suitable for peptide synthesis and backbone cyclization, either on solid support or in solution.

SCHEME VII

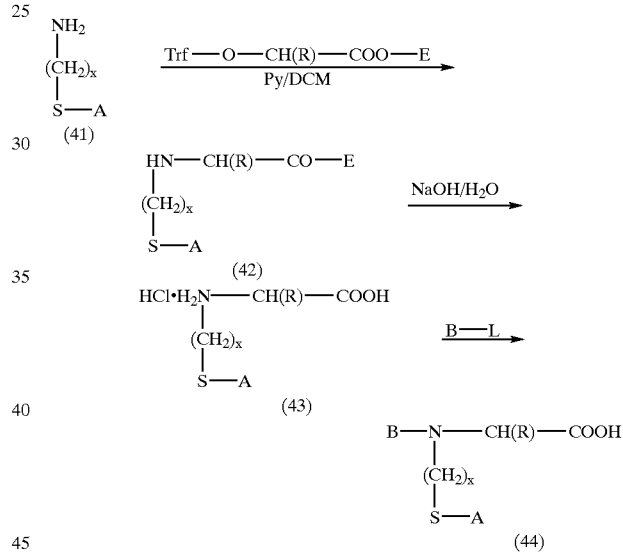

A = for example Bzl, t-Bu, Trt
B = for example Fmoc, Boc, Alloc
B—L = for example Fmoc—Osu, Boc$_2$O, Alloc—Cl
E = for example OMe, OEt
x = 1–10
R = amino acid side chains

SCHEME VIII

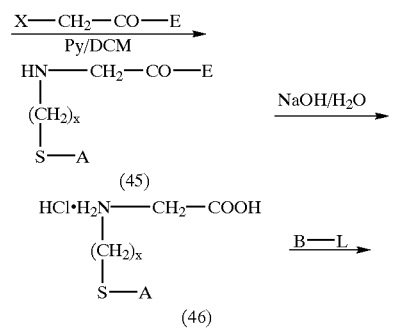

-continued

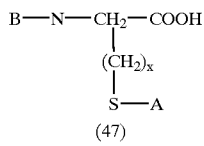

A = for example Bzl, t-Bu, Trt
B = for example Fmoc, Boc, Alloc
B——L = for example Fmoc——Osu, Boc₂O, Alloc——Cl
E = for example OMe, OEt
x = 1–10
X = Cl, Br, I.

SPECIFIC EXAMPLES OF PEPTIDES

Preparation of the novel backbone cyclized peptide analogs using the schematics outlined above will be illustrated by the following non-limiting specific examples:

Example 1

Ada-(D)Arg-Arg-cyclo(N$^\alpha$(1-(6-aminohexylene)
Gly-Hyp-Phe-D-Asp)-D-Phe-Phe-Arg-OH Stage 1
Boc-Arg(Tos)-O-resin→Fmoc-Phe-Arg(Tos)-O-resin Boc-L-Arg(Tos)-O-resin (0.256 g, 0.1 mmole, 0.39 meq of nitrogen/g) was placed in a shaker flask and swelled for two hours by the addition of DCM. The resin was then carried out through the procedure in Table 1 which includes two deprotections of the Boc protecting group with 55% TFA in DCM for a total of 22 minutes, washing, neutralization with 10% DIEA in NMP and washing (Table 1 steps 1–8). After positive ninhydrin test, as described in Kaiser et al., Anal Biochem., 34:595, 1970 and is incorporated herein by reference in its entirety, coupling (Table 1 steps 9–10) was achieved in NMP by the addition of Fmoc-L-Phe (0.232 g, 0.6 mmole) and after 5 minutes of shaking, solid BOP reagent (0.265 g, 0.6 mmole) was added to the flask.

TABLE 1

PROCEDURE FOR 0.1 mMOLE SCALE

| STEP NO. | SOLVENT/REAGENT | VOLUME (ML) | TIME (MIN) | REPEAT (XS) | COMMENT |
|---|---|---|---|---|---|
| 1 | DCM | 5 | 120 | 1 | Swells resin |
| 2 | DCM | 5 | 2 | 3 | |
| 3 | TFA/DCM 55% | 5 | 2 | 1 | Deprotection |
| 4 | TFA/DCM 55% | 5 | 20 | 1 | Deprotection |
| 5 | DCM | 5 | 2 | 3 | |
| 6 | NMP | 5 | 2 | 4 | check for positive nin. |
| 7 | DIEA/NMP | 5 | 5 | 2 | Neutralization |
| 8 | NMP | 5 | 2 | 5 | |
| 9 | Fmoc-AA in NMP | | 5 | 5 | Coupling add BOP 6 eq. add DIEA 120 600 1 12 eq. Check pH, adjust to pH 8 with DIEA |
| 10 | NMP | 5 | 2 | 5 | check for negative nin. |
| 11 | Pip/NMP 20% | 5 | 10 | 1 | Deprotection |
| 12 | Pip/NMP 20% | 5 | 10 | 1 | |
| 13 | NMP | 5 | 2 | 6 | check for positive nin. |

After shaking for 10 minutes, the mixture was adjusted to pH 8 (measured with wetted pH stick) by the addition of DIEA (0.209 mL, 1.2 mmole) and the flask shaken for 10 hours at ambient temperature. The resin was then washed and subjected to ninhydrin test. After negative ninhydrin test the resin was used for the next coupling.

Stage 2
Fmoc-Phe-Arg(Tos)-O-resin→Fmoc-N$^\alpha$(6-Boc amino hexylene)Gly-Hyp(OBzl)-Phe-D-Asp(t-Bu)-D-Phe-Phe-Arg(Tos)-O-resin The Fmoc-Phe-Arg(Tos)-O-resin (Stage 1) was subjected to two deprotections of the Fmoc protecting group by 20% Pip in NMP (Table 1 steps 11–13). After washing and ninhydrin test (Method J, below), coupling of Fmoc-D-Phe was achieved as described in Stage 1 (Table 1 steps 9–10) using Fmoc-D-Phe (0.232 g, 0.6 mmole), BOP reagent (0.265 g, 0.6 mmole) and DIEA (0.209 mL, 1.2 mmole). The resin was washed and the Fmoc group deprotected as described above (Table 1 steps 11–13). After washing and ninhydrin test, coupling of Fmoc-D-Asp(t-Bu) was achieved as described in Stage 1 (Table 1 steps 9–10) using Fmoc-D-Asp(t-Bu) (0.247 g, 0.6 mmole), BOP reagent (0.265 g, 0.6 mmole) and DIEA (0.209 mL, 1.2 mmole). The resin was washed and the Fmoc group deprotected as described above (Table 1 steps 11–13). After washing and ninhydrin test, coupling of Fmoc-L-Phe was achieved as described in Stage 1 (Table 1 steps 9–10) using Fmoc-L-Phe (0.232 g, 0.6 mmole), BOP reagent (0.265 g, 0.6 mmole) and DIEA (0.209 mL, 1.2 mmole). The resin was washed and the Fmoc group deprotected as described above (Table 1 steps 11–13). After washing and ninhydrin test, coupling of Fmoc-L-Hyp (OBzl) was achieved as described in Stage 1 (Table 1 steps 9–10) using Fmoc-L-Hyp(OBzl) (0.266 g, 0.6 mmole), BOP reagent (0.265 g, 0.6 mmole) and DIEA (0.209 mL, 1.2 mmole). The resin was washed and the Fmoc group deprotected as described above (Table 1 steps 11–13). The resin was washed and subjected to picric acid test (Method K). Coupling of Fmoc-N$^\alpha$(6-Boc amino hexylene)glycine was achieved as described in Stage 1 (Table 1 steps 9–10) using Fmoc-N$^\alpha$(6-Boc amino hexylene)glycine (0.3 g, 0.6 mmole), BOP reagent (0.265 g, 0.6 mmole) and DIEA (0.209 mL, 1.2 mmole). The resin was then washed and subjected to the picric acid test (Method K below). After negative test the resin was used for the next coupling.

Stage 3
Fmoc-N$^\alpha$(6-Boc amino hexylene)Gly-Hyp(OBzl)-Phe-D-Asp(t-Bu) -D-Phe-Phe-Arg (Tos)-O-resin→Fmoc-D-Arg (Tos)-Arg(Tos)-Arg(Tos,-N$^\alpha$(6-Boc amino hexylene)Gly-Hyp(OBzl)-Phe-D-Asp(t-Bu)-D-Phe-Phe-Arg(Tos)-O-resin The Fmoc-N$^\alpha$(6-Boc amino hexylene)Gly-Hyp(OBzl)-Phe-D-Asp(t-Bu)-D-Phe-Phe-Arg(Tos)-O -resin (Stage 2) was subjected to three deprotection of the Fmoc protecting group by 20% Pip in NMP (Table-2 steps 1–2). After washing, the picric acid test (Method K) was performed. If the test did not show 98±2%, deprotection of the peptide resin was subjected again to 3 deprotection steps (Table 2 steps 1–2), washing and picric acid test (Method K). Coupling of Fmoc-L-Arg(Tos) was achieved in NMP by the addition of (0.33 g, 0.6 mmole) and after 5 minutes of shaking, solid PyBOP reagent (0.28 g, 0.6 mmole) was added to the flask. After shaking for 10 minutes, the mixture was adjusted to pH 8 (measured with wetted pH stick) by the addition of DIEA (0.209 mL, 1.2 mmole) and the flask shaken for 2.5 hours at ambient temperature. The resin was then washed and subjected to a second coupling by the same procedure for 20 hours. After washing the resin was subjected to picric acid test (Method K) (Table 2 steps 3–6). If the test did not show 98±2% coupling the peptide resin was subjected again to a third coupling for 2 hours at 50°C.

(Table 2 step 7). The resin was washed subjected to three deprotection of the Fmoc protecting group by 20% Pip in NMP (Table 2 steps 1–2). After washing picric acid test (Method K) was performed.

TABLE 2

PROCEDURE FOR 0.1 mMOLE SCALE

| STEP NO. | SOLVENT/ REAGENT | VOLUME (ML) | TIME (MIN) | REPEAT (XS) | COMMENT |
|---|---|---|---|---|---|
| 1 | Piperidine/ NMP 20% | 5 | 10 | 3 | Deprotection |
| 2 | NMP | 5 | 2 | 6 | Picric acid test. |
| 3 | Fmoc-AA in NMP add | 5 | 5 | | Coupling 6 eq. |
| | PyBroP add DIEA | | 150 | 1 | 12 eq. Check pH, adjust to pH 8 with DIEA. |
| 4 | NMP | 5 | 2 | 3 | check for negative nin. |
| 5 | Fmoc-AA in NMP add | 5 | 5 | | Coupling 6 eq. |
| | PyBroP add DIEA | | 20 hr. | 1 | 12 eq. Check pH, adjust to pH 8 with DIEA. |
| 6 | NMP | 5 | 2 | 4 | Picric acid test. If less than 98 ± 2% coupling repeat Steps 4–5 |
| 7 | Fmoc-AA in NMP add | 5 | 5 | | Coupling at 50° C. 6 eq. |
| | PyBOP add DIEA | | 120 | 1 | 12 eq. Check pH, adjust to pH 8 with DIEA. |
| 8 | NMP | 5 | 2 | 4 | |

If the test did not show 98±2% deprotection, the peptide resin was subjected again to 3 deprotection steps (Table 2 steps 1–2), washing and the picric acid test (Method K). Coupling of Fmoc-D-Arg(Tos) was achieved in NMP as described in Stage 1 (Table 1 steps 9–10) using Fmoc-D-Arg(Tos) (0.33 g, 0.6 mmole), BOP reagent (0.265 g, 0.6 mmole) and DIEA (0.209 mL, 1.2 mmole). The resin was washed 6 times with NMP (Table 1 step 15) and used in the next stages.

Stage 4

Fmoc-D-Arg(Tos)-Arg(Tos)-N$^\alpha$(6-Boc amino hexylene)Gly-HYp(OBzl)-Phe-D-Asp(t-Bu)-D-Phe-Phe-Arg(Tos)-O-resin→Ada-D-Arg-Arg-cyclo(N$^\alpha$(1-(6-amidohexylene)Gly-Hyp-Phe-D-Asp)-D-Phe-Phe-Arg-OH The Fmoc-D-Arg(Tos)-Arg(Tos)-N$^\alpha$(6-Boc amino hexylene)Gly-Hyp(OBzl)-Phe-D-Asp(t-Bu)-D-Phe-Phe-Arg(Tos)-O-resin (Stage 3) was subjected to deprotection of the Boc and t-Bu protecting groups and on resin cyclization according to Table 3. The peptide resin was washed with DCM and deprotected as described in Stage 1 by 55% TFA in DCM. After washing and neutralization by 10%. DIEA in NMP and washing 6 times with DCM the peptide resin was dried in vacuo for 24 hours. The dry peptide resin weight, 0.4 g, it was divided into two parts. 0.2 g of the peptide resin was swollen 2 hours in 5 mL NMP and cyclized as follows: Solid TBTU reagent (0.19 g, 6 mmole) was added to the flask. After shaking for 10 minutes, the mixture was adjusted to pH 8 by the addition of DIEA (0.209 mL, 1.2 mmole) and the flask shaken for 2.5 hours at ambient temperature. The resin was then washed and subjected to a second coupling by the same procedure for 20 hours. After washing the resin was subjected to picric acid test (Method K) (Table 3 steps 8–11). If the test did not show 98±2% cyclization the peptide resin was subjected again to a third cyclization for 2 hours at 50° C. (Table 2 step 12). The resin was washed, subjected to three deprotection of the Fmoc protecting group by 20% Pip in NMP (Table 2 steps 1–2). After washing and ninhydrin test, the N-terminal amino group was blocked by Ada. Adamantane acetic acid (0.108 g, 6 mmole), BOP reagent (0.265 g, 0.6 mmole) and DIEA (0.209 mL, 1.2 mmole) were added and the flask shaken for 2 hours. After washing 6 times with NMP (Table 2 step 13), ninhydrin test (Method J) was performed. If the test was positive or slightly positive the protecting with adamantane acetic acid was repeated. If the ninhydrin test was negative, the peptide resin was washed 6 times with NMP and 6 times with DCM. The resin was dried under vacuum for 24 hours. The dried resin was subjected to HF as follows: to the dry peptide resin (0.2 g) in the HF reaction flask, anisole (2 mL) was added and the peptide treated with 20 mL liquid HF at −20° C. for 2 hours. After the evaporation of the HF under vacuum, the anisole was washed with ether (20 mL, 5 times) and the solid residue dried in vacuum. The peptide was extracted from the resin with TFA (10 mL, 3 times) and the TFA evaporated under vacuum. The residue was dissolved in 20 mL 30% AcOH and lyophilized. This process was repeated 3 times. The crude peptide was purified by semiprep HPLC (Method H). The final product was obtained as white powder by lyophilization from dioxane, which gave 42 mg (56%) of the title compound.

HPLC (Method G) RT 32.15 minutes, 95%

TOF MS: 1351.4 (M$^+$)

AAA in agreement with the title compound

Table 3 Follows at This Point

TABLE 3

PROCEDURE FOR 0.05 mMOLE SCALE

| STEP NO. | SOLVENT/ REAGENT | VOLUME (ML) | TIME (MIN) | REPEAT (XS) | COMMENT |
|---|---|---|---|---|---|
| 1 | DCM | 5 | 2 | 3 | |
| 2 | TFA/DCM 55% | 5 | 2 | 1 | Deprotection |
| 3 | TFA/DCM 55% | 5 | 20 | 1 | Deprotection |
| 4 | DCM | 5 | 2 | 3 | |
| 5 | NMP | 5 | 2 | 4 | |
| 6 | DIEA/NMP 10% | 5 | 5 | 2 | Neutralization |
| 7 | NMP | 5 | 2 | 5 | |
| 8 | TBTU/NMP/ DIEA | 5 | 150 | 3 | Cyclization |
| 9 | NMP | 5 | 2 | 4 | Picric acid test. If less than 98 ± 2% coupling perform Steps 10–12. If above 98 ± 2%, go to step 13. |
| 10 | TBTU/NMP/ DIEA | 5 | 20 hr | 3 | Cyclization. Check pH, adjust to pH 8 with DIEA. |
| 11 | NMP | 5 | 2 | 4 | Picric acid test. If less than 98 ± 2% coupling perform Steps 12. If above 98 ± 2%, go to step 13 |
| 12 | TBTU/NMP/ DIEA | 5 | 120 | 3 | Cyclization, 50 C. Check pH, adjust to pH 8 with DIEA. |
| 13 | NMP | 5 | 2 | 6 | |

TABLE 3-continued

PROCEDURE FOR 0.05 mMOLE SCALE

| STEP NO. | SOLVENT/ REAGENT | VOLUME (ML) | TIME (MIN) | REPEAT (XS) | COMMENT |
|---|---|---|---|---|---|
| 14 | Pip/NMP 20% | 5 | 10 | 1 | Deprotection |
| 15 | Pip/NMP 20% | 5 | 10 | 1 | |
| 16 | NMP | 5 | 2 | 6 | Check for positive nin. |
| 17 | AdacOH/ BOP/NMP | 5 | 2 | 1 | |
| 18 | NMP | 5 | 2 | 6 | Check for negative nin. |
| 19 | DCM | 5 | 2 | 4 | |

Example 2

NON-CYCLIZED PEPTIDE (Control for Biological Assays)

Ada-D-Arg-Arg-N$^{\alpha}$(6-acetamidohexylene)Gly-Hyp-Phe-D-Asp(NH-Me)-D-Phe-Phe-Arg-OH The Fmoc-D-Arg(Tos)-Arg(Tos)-N$^{\alpha}$(6-amino hexylene)Gly-Hyp(OBzl)-Phe-D-Asp-D-Phe-Phe-Arg(Tos)-O-resin (0.2 g) which was prepared in Example 1 Stage 4 was subjected to acetylation of the 6-amino side chain of N$^{\alpha}$(6-acetamidohexylene)Gly and to methyl amidation of the carboxylic group of D-Asp as described in Table 4. The peptide resin was swollen in 5 mL NMP for 2 hours and AcO (0.113 mL, 12 mmole) and PP (17 mg) were added. After 30 minutes, the resin was washed with NMP 6 times and subjected to ninhydrin test. If the test was positive or slightly positive the acetylation reaction was repeated. If the ninhydrin test was negative, the carboxy group of D-Asp was activated by the addition of HOBT (0.040 g, 0.3 mmole) and DIC (0.047 mL, 0.3 mmole) to the peptide resin in NMP. The mixture was shaken for half an hour and a solution of 30% methylamine in EtOH (0.2 mL) was added. After one hour, the resin was washed 6 times with NMP and the terminal Fmoc group removed by 20% Pip in NMP (Table 4 steps 7–9). After washing with NMP the N-terminal amino group was blocked by Ada as described in Example 1 Stage 4 and the resin was washed with NMP and DCM (Table 4 steps 10–12) and the resin dried in vacuo. The peptide was deprotected and cleaved from the resin by HF. To the dry peptide resin (0.2 g) in the HF reaction flask, anisole (2 mL) was added and the peptide treated with 20 mL liquid HF at −20° C. for 2 hours. After the evaporation of the HF under vacuum, the anisole was washed with ether (20 mL 5 times) and the solid residue dried in vacuo. The peptide was extracted from the resin with TFA (10 mL, 3 times) and the TFA evaporated under vacuum. The residue was dissolved in 20 mL 30% AcOH and lyophilized. This process was repeated 3 times. The crude peptide was purified by semi-prep HPLC (Method H). The final product was obtained as white powder by lyophilization from dioxane, which gave 48 mg (64%) of the title compound.

HPLC (Method G) RT 27.70 minutes, 93%

TOF MS: 1424.6 (M$^+$)

AAA in agreement with the title compound

TABLE 4

PROCEDURE FOR 0.05 mMOLE SCALE

| STEP NO. | SOLVENT/ REAGENT | VOLUME (ML) | TIME (MIN) | REPEAT (XS) | COMMENT |
|---|---|---|---|---|---|
| 1 | NMP | 5 | 120 | 1 | Swells resin |
| 2 | AC$_2$O/PP/ NMP | 5 | 30 | 1 | Protecting of side chain |
| 3 | NMP | 5 | 2 | 6 | Check for negative nin. |
| 4 | DIC/HOBT/ NMP | 5 | 30 | 1 | Activation of COOH side chain |
| 5 | MeNH$_2$/ EtOH/ | 5 | 60 | 1 | Protecting of side chain |
| 6 | NMP | 5 | 2 | 6 | |
| 7 | Pip/NMP 20% | 5 | 10 | 1 | Deprotection |
| 8 | Pip/NMP 20% | 5 | 10 | 1 | |
| 9 | NMP | 5 | 2 | 6 | Check for positive nin. |
| 10 | AdacOH/ BOP/NMP | 5 | 2 | 1 | |
| 11 | NMP | 5 | 2 | 6 | Check for negative nin. |
| 12 | DCM | 5 | 2 | 4 | |

Example 3

H-D-Arg-Arg-cyclo(N$^{\alpha}$(1-(4-propanoyl))Gly-Hyp-Phe-N$^{\alpha}$(3-amido-propylene)Gly)-Ser-D-Phe-Phe-Arc-OH Stage 1

Fmoc-Phe-Arg(Tos)-O-resin→Fmoc-N$^{\alpha}$(4-t-Bu-propanoyl) Gly-Hyp(oBzl)-Phe-NN$^{\alpha}$(3-Boc amino proylene)-Gly-Ser (Bzl)-D-Phe-Phe-Arg(Tos)-O-resin Fmoc-Phe-Arg(Tos)-O-resin prepared from Boc-Arg(Tos)-O-Resin (0.3 g, 0.1 mmole) (Example 1, Stage 1) was subjected to two deprotection of the Fmoc protecting group by 20% piperidine in NMP (Table 1, steps 11–13). After washing and ninhydrin test (Method J), coupling of Fmoc-D-Phe was achieved as described in Stage 1 (Example 1) (Table 1 steps 9–10) using Fmoc-D-Phe (0.232 g, 0.6 mmole), BOP reagent (0.265 g, 0.6 mmole) and DIEA (0.209 mL, 1.2 mmole). The resin was washed and the Fmoc group deprotected as described above (Table 1, steps 11–13). After washing and ninhydrin test (Method J), coupling of Fmoc-Ser(BzL) was achieved as described in Stage 1 (Example 1) (Table 1 steps 9–10) using Fmoc-Ser(Bzl) (0.25 g, 0.6 mmole), BOP reagent (0.265 g, 0.6 mmole) and DIEA (0.209 mL, 1.2 mmole). The resin was washed and the Fmoc group deprotected as described above (Table 1, steps 11–13). After washing and picric acid test (Method K), coupling of Fmoc-N$^{\alpha}$(3-Boc amino propylene)glycine was achieved as described in Table 1, steps 9–10 using Fmoc-N$^{\alpha}$(3-Boc amino propylene)Gly (0.272 g, 0.6 mmole), BOP reagent (0.265 g, 0.6 mmole) and DIEA (0.209 mL, 1.2 mmole). The resin was washed and subjected to three deprotection of the Fmoc protecting group by 20% Pip in NMP (Table 2, steps 1–2). After washing picric acid test (Method K) was performed. If the test did not show 98±2% deprotection the peptide resin was subjected again to 3 deprotection steps (Table 2, steps 1–2), washing and picric acid test (Method K). Coupling of Fmoc-L-Hyp(OBzl) was achieved in NMP by the addition of Fmoc-L-Hyp(OBzl) (0.33 g, 0.6 mmole) and after 5 minutes of shaking, solid PyBrOP reagent (0.28 g, 0.6 mmole) was added to the flask. After shaking for 10 minutes, the mixture was adjusted to pH 8 by the addition of DIEA (0.209 mL, 1.2 mmole) and the flask shaken for 2.5 hours at ambient temperature. The resin was then washed and subjected to a second coupling by the same procedure for 20 hours. After washing the resin was subjected to picric acid test (Method K) (Table 2, steps 3–6). If the test did not show 98±2% coupling the peptide resin was subjected again to a third coupling for 2 hours at 50° C. (Table 2, step 7). The resin was washed subjected to three deprotection of the Fmoc protecting group by 20% Pip in NMP (Table 2, steps 1–2). After washing picric acid test (Method K) was performed. If the picric acid test did not show $^{98\pm2}$% deprotection, the resin was subjected again to deprotections steps (Table 2, steps 1–2). Coupling of Fmoc-Phe was achieved in NMP by the addition of Fmoc-Phe (0.232 g, 0.6 mmole), BOP reagent (0.265 g, 0.6 mmole) and DIEA (0.209 mL, 1.2 mmole). The resin was washed and after picric acid test (Method K) the Fmoc group deprotected as described above (Table 2, steps 1–2). After washing picric acid test (Method K) was performed. If the test did not show 98±2% deprotection the peptide resin was subjected again to 3 deprotection steps (Table 2, steps 1–2), washing and picric acid test (Method K). Coupling of $N^\alpha$(3-t-Bu carboxy propylene)Gly was achieved as described in Table 1 steps 9–10 using $N^\alpha$(3-t-Bu carboxy propylene)Gly (0.264 g, 0.6 mmole), BOP reagent (0.265 g, 0.6 mmole) and DIEA (0.209 mL, 1.2 mmole). The resin was then washed and subjected to the picric acid test (Method K). After negative test the resin was used for the next coupling.

Stage 2

Fmoc-$N^\alpha$(4-t-Bu-propanoyl)Gly-Hyp(OBzl)-Phe-$N^\alpha$(3-Boc amino propylene)-Gly-Ser(Bzl)-D-Phe-Phe-Arg(Tos)-O-resin→Fmoc-D-ArQ(Tos)-Arg(Tos)-$N^\alpha$(4-t-Bu-Propanoyl) Gly-Hyp(OBzl)-Phe-$N^\alpha$(3-Boc amino propylene)-Gly-Ser (Bzl)-D-Phe-Phe-Arg(Tos)-O-resin Fmoc-$N^\alpha$(4-t-Bu-propanoyl)Gly-Hyp(oBzl)-Phe-$N^\alpha$(3-Boc amino propylene)-Gly-Ser(Bzl)-D-Phe-Phe-Arg(Tos)-O-resin (Stage 1) was subjected to three deprotection of the Fmoc protecting group by 20% Piperidine in NMP (Table 2, steps 1–2). After washing picric acid (Method K) test was performed. If the test did not show 98±2% deprotection the peptide resin was subjected again to 3 deprotection steps (Table 6, steps 1–2), washing and picric acid test. Coupling of Fmoc-L-Arg(Tos) was achieved in NMP by the addition of (0.33 g, 0.6 mmole) and after 5 minutes of shaking, solid PyBroP reagent (0.28 g, 0.6 mmole) was added to the flask. After shaking for 10 minutes, the mixture was adjusted to pH 8 by the addition of DIEA (0.209 mL, 1.2 mmole) and the flask shaken for 2.5 hours at ambient temperature. The resin was then washed and subjected to a second coupling by the same procedure for 20 hours. After washing the resin was subjected to picric acid test (Method K) (Table 2, steps 3–6). If the test did not show 98±2% coupling the peptide resin was subjected again to a third coupling for 2 hours at 50° C. (Table 2, step 7). The resin was washed subjected to three deprotection of the Fmoc protecting group by 20% Pip in NMP (Table 2, steps 1–2). After washing picric acid test (Method K) was performed. If the test did not show 98±2% deprotection the peptide resin was subjected again to 3 deprotection steps (Table 2, steps 1–2), washing and picric acid test (Method K). Coupling of Fmoc-D-Arg(Tos) was achieved in NMP as described in Stage 1 (Table 1, steps 9–10) using Fmoc-D-Arg(Tos) (0.33 g, 0.6 mmole), BOP reagent (0.265 g, 0.6 mmole) and DIEA (0.209 mL, 1.2 mmole). The resin was washed 6 times with NMP (Table 1, step 15) and used in the next stages.

Stage 3

Fmoc-D-Arg(Tos)-Arg(Tos)-$N^\alpha$(4-t-Bu-Propanoyl)Gly-Hyp (OBzl)-Phe-$N^\alpha$(3-Boc amino-propylene)Gly-Ser(Bzl)-D-Phe-Phe-Arg(Tos)-O-resin→H-D-Arg-ArQ-cyclo($N^\alpha$(4-propanoyl))Gly-Hyp-Phe-$N^\alpha$(3-amido-propyl)Gly)-Ser-D-Phe-Phe-Arg-OH Fmoc-D-Arg(Tos)-Arg(Tos)-$N^\alpha$(4-t-Bu-propanoyl)Gly-Hyp(OBzl)-Phe-$N^\alpha$(3-Boc amino-propylene)Gly-Ser(Bzl)-D-Phe-Phe-Arg(Tos)-O-resin (Stage 2) was subjected to deprotection of the Boc and t-Bu protecting groups and on resin cyclization according to Table 5. The peptide resin was washed with DCM and deprotected as described in Stage 1 by 55%. TFA in DCM. After washing and neutralization by 10% DIEA in NMP and washing 6 times with and NMP (Table 5, steps 1–5) the peptide was cyclized as follow: solid TBTU reagent (0.19 g, 6 mmole) was added to the flask. After shaking for 10 minutes, the mixture was adjusted to pH 8 by the addition of DIEA (0.209 mL, 1.2 mmole) and the flask shaken for 2.5 hours at ambient temperature. The resin was then washed and subjected to a second coupling by the same procedure for 20 hours. After washing the resin was subjected to picric acid test (Method K) (Table 3, steps 8–11). If the test did not show 98±2% cyclization the peptide resin was subjected again to a third cyclization for 2 hours at 50° C. (Table 2, step 12). The resin was washed, subjected to three deprotection of the Fmoc protecting group by 20% Pip in NMP (Table 5, steps 14–15). After washing 6 times with NMP and 4 times with DCM, the resin was dried in vacuo for 24 hours. The dried resin was subjected to HF as follows: to the dry peptide resin (0.4 g) in the HF reaction flask, anisole (2 mL) was added and the peptide treated with 20 mL liquid HF at −20° C. for 2 hours. After the evaporation of the HF under vacuum, the anisole was washed with ether (20 mL, 5 times) and the solid residue dried in vacuo. The peptide was extracted from the resin with TFA (10 mL 3 times) and the TFA evaporated under vacuum. The residue was dissolved in 20 mL 30% AcOH and lyophilized. This process was repeated 3 times. The crude peptide was purified by semipreparative HPLC (Method H). The final product was obtained as white powder by lyophilization from dioxane, which gave 59 mg (340) of the title compound.

Table 5 Follows at this Point

TABLE 5

PROCEDURE FOR 0.1 mMOLE SCALE

| STEP NO. | SOLVENT/ REAGENT | VOLUME (ML) | TIME (MIN) | REPEAT (XS) | COMMENT |
|---|---|---|---|---|---|
| 1 | DCM | 10 | 2 | 3 | |
| 2 | TFA/DCM 55% | 10 | 2 | 1 | Deprotection |
| 3 | TFA/DCM 55% | 10 | 20 | 1 | Deprotection |
| 4 | DCM | 10 | 2 | 3 | |
| 5 | NMP | 10 | 2 | 4 | |
| 6 | DIEA/NMP 10% | 10 | 5 | 2 | Neutralization |
| 7 | NMP | 10 | 2 | 5 | |
| 8 | TBTU/NMP/ DIEA | 10 | 150 | 3 | Cyclization |
| 9 | NMP | 10 | 2 | 4 | Picric acid test. If less than 98 ± 2% Coupling perform Steps 10. |

TABLE 5-continued

PROCEDURE FOR 0.1 mMOLE SCALE

| STEP NO. | SOLVENT/ REAGENT | VOLUME (ML) | TIME (MIN) | REPEAT (XS) | COMMENT |
|---|---|---|---|---|---|
| 10 | TBTU/NMP/ DIEA | 10 | 20h | 3 | Cyclization, Check pH, adjust to pH 8 with DIEA. |
| 11 | NMP | 10 | 2 | 4 | Picric acid test. If less than 98 ± 2% coupling perform Step 12. |
| 12 | TBTU/NMP/ DIEA | 10 | 120 | 3 | Cyclization, 50° C. Check pH, adjust to pH 8 with DIEA. |
| 13 | NMP | 10 | 2 | 6 | |
| 14 | Piperidine/ NMP 20% | 10 | 10 | 1 | Deprotection |
| 15 | Piperidine/ NMP 20% | 10 | 1 | | |
| 16 | NMP | 10 | 2 | 6 | Check for positive nin. |
| 17 | DCM | 10 | 2 | 4 | |

HPLC (Method G)RT 33.62 minutes (91%)

TOF MS: 1278 (M$^+$)

AAA in agreement with the title compound

Example 4

H-D-Arg-Arg-cyclo (N$^\alpha$(4-propanoyl)Gly-Hyp-Phe-N$^\alpha$(3-amido-propyl)-S-Phe)-Ser-D-Phe-Phe-Arg-OH Title compound was synthesized according to Example 3 except that in stage 1, Fmoc-N$^\alpha$(3-Boc-amino-propylene)-S-Phe 0.326) was substituted for Fmoc-N$^\alpha$(3-Boc amino propylene)Gly. A total of 0.643 g Boc-L-Arg(Tos)-O-resin (0.39 meq/g, 0.250 mole) was used and reagent quantities were adjusted accordingly. Cyclic peptide yield (from half the total resin sed) was 74 mg (42%) of the title compound.

SPECIFIC EXAMPLES OF BUILDING UNITS

The following specific examples of novel building units are provided for illustrative purposes not meant to be limiting. The following is described in sections, including "Procedures", "Methods", "Compounds" and "EXAMPLES". "Procedures" are detailed stepwise descriptions of synthetic procedures according to the more general schemes. "Methods" are general descriptions of analyses used to determine the progress of the synthetic process. Numbered "Compounds" are either the starting material or intermediates for further numbered "Compounds" the synthesis of which progresses according to the specified "Procedure." Several "Compounds" used in series produce "EXAMPLES" of novel building units of the present invention. For instance, "Compounds" 27–29, 41–44, 46–47, 51–55, 62, 63, 67 and 76–79 are actually "EXAMPLES" 5–25, respectively, of novel building units of the present invention. "Compounds" 1–26, 30–40, 45, 48–50, 56–61, 64–66, 68–75 are starting materials or intermediates (only) for the synthesis of "EXAMPLES".

Procedure 1
Synthesis of N-Boc alkylene diamines (BocNH(CH$_2$)$_n$NH$_2$) (Known Compounds)

To a solution of 0.5 mole alkylene diamine in 0.5 L CHCl$_3$ cooled in an ice-water bath, was added dropwise, with stirring, a solution of 10.91 g (0.05 mole) BoC$_2$O in 0.25 L CHCl$_3$ for 3 h. The reaction mixture was stirred for 16 h. at room temperature and then washed with water (8×250 mL). The organic phase was dried over Na$_2$SO$_4$ and evaporated to dryness in vacuo.

Procedure 2
Synthesis of N-Boc, N-Bzl alkylene diamines (BocNH (CH$_2$)$_n$NH-Bzl).

To a solution of 0.05 mole of mono Boc alkylene diamine in 60 mL MeOH was added 2.77 mL (0.02 mole) Et$_3$N, 9.02 g (0.075 mole) MgSO$_4$, and 5.56 mL (0.055 mole) of freshly distilled benzaldehyde. The reaction mixture was stirred under room temperature for 1.5 h. Then 11.34 g (0.3 mole) of NaBH$_4$ were added in small portions during 0.5 h with cooling to −5° C. The reaction mixture was then stirred for 1 h at −5° C. and for another 1 h at 0° C. The reaction was stopped by addition of 200 mL water and the product was extracted with EtOAc (3×200 mL). The combined EtOAc extracts were washed with water (4×100 mL). The organic phase was extract with 0.5 N HCl (4×100 mL) and the aqueous solution was neutralized under cooling with 25 mL 25% NH$_4$OH, extracted with CHCl$_3$ (3×100 ml) and the combined extracts were washed with water (3×80 mL), dried over Na$_2$SO$_4$ and evaporated to dryness in vacuo.

Procedure 3
Synthesis of (R) or (S) α-hydroxy acids (Known Compounds)

To a solution of 16.52 g (0.1 mole) (R) or (S)amino acid in 150 ml 1N H$_2$SO$_4$ was added dropwise a solution of 10.35 g (0.15 mole) NaNO$_2$ in 100 mL H$_2$O during 0.5 h with stirring and cooling in an ice bath. The reaction mixture was stirred 3 h. at 0° C. and additional 18 h at room temperature, then the (R)- or (S)-hydroxy acid was extracted with ether in a continuous ether extractor. The etheral solution was washed with 1N HCl (2×50 mL), H$_2$O (3×80 mL), dried over Na$_2$SO$_4$ and evaporated to dryness. The product was triturated twice from ether:petrol-ether (40–60° C.) (1:10). The precipitate was filtered, washed with 50 mL petrol-ether and dried.

Procedure 4
Synthesis of (R) or (S) α-hydroxy acid methyl esters (Known Compounds)

To a suspension of 0.065 mole (R)- or (S)-hydroxy acid in 100 mL ether was added under cooling in an ice bath 300 mL of an etheral solution of CH$_2$N$_2$ until stable yellow color of reaction mixture was obtained. Then the ether solution was washed with 5% KHCO$_3$ (3×100 mL) and H$_2$O (2×80 mL), dried over Na$_2$SO$_4$ and evaporated to dryness. The product was dried in vacuo.

Procedure 5
Synthesis of triflate of (R) or (S) α-hydroxy acid methyl esters To a cooled solution of 2.67 ml (0.033 mole) pyridine in 20 mL dry DCM was added 5.55 mL (0.033 mole) Trf$_2$O at −20° C. (dry ice in EtOH bath), then after 5 min a solution of 0.03 mole (R) or (S) α-hydroxy acid methyl ester in 20 mL dry DCM was added dropwise. The reaction mixture was stirred at room temperature for 45 min, then was passed through a short silica gel column (2 cm). The product was eluted with 400 mL of petrol-ether:methylene-chloride (1:1). The solvent was evaporated in vacuo.

Procedure 6

Synthesis of (R) or (S) $N^\alpha$(Bzl) ($N^\omega$-Boc-amino alkylene) amino acid methyl esters ((R) or (S) BocNH(CH$_2$)$_n$N(Bzl)CH(R)COOMe)

To a solution of 0.022 mole of $N^\alpha$-Boc, $N^\omega$-Bzl alkylene diamine in 20 mL of dry DCM was added 3.04 mL (0.022 mole) Et$_3$N. Then a solution of 0.02 mole of (R) or (S) α-hydroxy acid methyl ester triflate in 25 mL dry DCM was added dropwise (0.5 h.) under cooling in an ice-water bath. The reaction mixture was stirred at room temperature for 18 h. Then 150 mL of CHCl$_3$ was added and the yellow solution was washed with water (3×80 mL). The organic phase was dried over Na$_2$SO$_4$ and adsorbed on silica-gel and dried in vacuo. The silica-gel was washed on filter with 0.5 L of petrol-ether and with 0.5 L of 2% EA in PE. Then the product was eluted from silica with 0.5 L of mixture petrol-ether:ethyl-acetate (4:1). The solvent was evaporated in vacuo. If the product was not clean it was further purified on a small column of silica-gel (250 mL). The first impurities were eluted with 0.8 L of hexane then the product was eluted with 1.5 L of mixture of petrol-ether:ethyl-acetate (4:1).

Procedure 7

Hydrolysis of methyl esters

To a solution of 0.015 mole of methyl ester in 40 mL MeOH was added 10 mL 7.5 N NaOH cooled in an ice-water bath. The reaction mixture was stirred at room temperature for approximately 24 h (until the methyl ester spot disappears on TLC). Then 100 mL of water were added and the reaction mixture was washed with petrol-ether (3×80 mL). The aqueous solution was acidified under cooling by addition of 40 mL 2N HCL. The product was extracted with a mixture of CHCl$_3$:i-PrOH-(3:1) (3×80 mL), dried over Na$_2$SO$_4$, evaporated to dryness and dried in vacuo to obtain a white foam in quantitative yield.

Procedure 8

Removal of Bzl by Hydrogenation with Pd/C

To a solution of 0.012 mole (R) or (S)$N^\alpha$(Bzl) ($N^\omega$-Boc-amino alkylene) amino acid in 60 mL MeOH-DMF (11-1) was added 0.5 g 10% Pd/C. The solution was hydrogenated for 4 h under a pressure of 45–50 Psi at room temperature. Then 200 mL of a mixture of DMF:MeOH:H$_2$O:glacial AcOH (1:3:5:1) was added.

The catalyst was filtrated off and washed (is the acetic acid?) with H$_2$O or MeOH (2×15 mL). The combined filtrate was evaporated to dryness and recrystallized from methanol:ether (15 mL:250). The precipitate was filtered and dried in vacuo.

Procedure 9

Synthesis of (R) or (S)$N^\alpha$(Fmoc) ($N^\omega$-Boc-amino alkylene) amino acid To 50 mL water was added 0.07 mole of (R) or (S) $N^\omega$($N^\alpha$-Boc-amino alkylene) amino acid and 1.95 mL (0.014 mole) Et$_3$N. The suspension was stirred 2–3 h until a clear solution was obtained. Then a solution of 2.25 g (0.07 mole) of FmocOSu in 100 mL ACN was added. The reaction mixture was stirred 18 h at room temperature, then 150 mL water was added and the solution was washed with petrol-ether (3×100 mL) and with ether:petrol-ether (1:4). The aqueous solution was acidified by addition of 14 mL 1N HCL. The product was extracted with EtOAc (4×100 mL) and the organic phase was washed with 0.5 N HCl (2×50 mL), H$_2$O (3×80 mL), dried over Na$_2$SO$_4$, evaporated to dryness and recrystallized from ether:petrol-ether (80 mL:200 mL)

Procedure 10

Synthesis of S-benzylcysteamine (Bzl-S—(CH$_2$HN$_2$) (Known compound).

To a suspension of 0.1 mole cysteamine hydrochloride in 20 mL methanol were added 13.6 mL of 25% ammonia solution, followed by dropwise addition of 0.12 mole benzyl bromide at room temperature. The mixture was stirred for 0.5 h, and the formed precipitate of S-dibenzylcysteamine was collected by filtration. The product was extracted with ether (3×100 mL) and the organic phase was successively washed with brine (2×100 mL), dried over MgSO$_4$ and the solvent evaporated in vacuo. The crude product was essentially pure enough for the next step. It could, however, be recrystallized from ethyl acetate. Yield 86%, of white solid. m.p. 85–6° C. NMR (CDCl$_3$) in agreement with the title compound.

Procedure 11

Synthesis of $N^\alpha$-(ω-(benzylthio)alkylene)phthalimides ((Bzl-S—(CH$_2$)$_n$—N=Pht)) (Known Compounds)

N-(ω-bromoalkylene)phthalimide (0.1 mole) and benzyl mercaptane (0.11 mole) were stirred with 0.1 mole potassium carbonate in 100 mL DMSO at 50° C. for 24 hours. The mixture was poured into ice-water and the product was allowed to crystallize for 0.5 hour, collected by filtration and recrystallized from i-PrOH.

Procedure 12

Synthesis of $N^\alpha$-(ω-(benzylthio)alkyl)amines (Bzl-S—(CH$_2$)$_n$—NH$_2$) (Known Compounds)

Hydrazinolysis of the phthalimide group was performed by refluxing 0.09 mole of N-(ω-(benzylthio)alkylene)-phthalimide (Procedure 11) with 120 mL 1M solution of hydrazine hydrate in ethanol (diluted with additional 220 mL ethanol) for 2 hours. The formed precipitate was collected by filtration and hydrolyzed with 180 mL 2N HCl at 50° C. for 0.5 hour. The water was evaporated in vacuo and the crude hydrochloride dissolved in 50 mL 25% ammonia solution. The free amine was extracted with DCM (4×100 mL) and the organic phase was washed with brine (2×100 mL), dried over MgSO$_4$ and the solvent evaporated in vacuo. The crude N-(ω-(benzylthio)alkyl)amine was distilled under reduced pressure, and appeared as colorless oil, which could be kept refrigerated under nitrogen for prolonged periods.

Procedure 13

Synthesis of (R) and (S) N-(ω-(benzylthio)alkylene)amino acids methyl esters ((R) or (S)(Bzl-S—(CH$_2$)$_n$—NH—CH(R)—COOMe))

To a solution of 15 mmol N-(ω-(benzylthio)alkyl)amine and 15 mmol DIEA in 55 mL DCM was added dropwise a solution of 15 mmol (R) or (S) α-hydroxy acid methyl ester triflate (Procedure 5) in 55 mL DCM at 0° C. The reaction mixture was then stirred at room temperature for 18 h. The mixture was then diluted with 100 mL DCM and washed with water (3×100 mL). The crude product was cleaned on a silica-gel column with DCM:MeOH (99:1), and was further crystallized from DIE:hexane.

In the case of Glycine, bromoacetic acid esters were suitable starting materials. Identical results were obtained when both these substrates were reacted with N-(ω-(benzylthio)alkyl)amines.

Procedure 14

Synthesis of (R) or (S)Boc-N-(ω-(benzylthio)alkylene) amino acids ((R) or (S)(Bzl-S-(CH$_2$)$_n$—N(Boc)-CH(R)—COOH))

10 mmol (R) or (S) N-(ω-(benzylthio)alkylene)amino acid methyl ester was dissolved in 50 mL 1,4-dioxane and 50 mL 1N NaOH were added. The mixture was stirred at room temperature overnight. The disappearance of the starting material was followed by TLC (Silica gel+$F_{254}$, $CHCl_3$:MeOH-1:4). When all the ester was hydrolyzed, 50 mL water were added, followed by 30 mmol $Boc^2O$. The mixture was stirred overnight, then the dioxane was evaporated in vacuo, the mixture was cooled in an ice-water bath, covered with 100 mL EtAc and acidified with saturated $KHSO_4$ to pH 2–3. The layers were separated, and the aqueous layer was extracted with additional 2×100 mL EtOAc. The organic layer was washed with water (2×100 mL), dried over $MgSO_4$ and the solvent evaporated in vacuo. The crude product was cleaned on a silica-gel column with DCM:MeOH-99:1 or crystallized from DIE:hexane.

Procedure 15

Synthesis of dipeptides (S,S)-Boc-amino acid-$N^\alpha$-(ω-(benzylthio)alkylene)amino acids esters A solution of 1.1 mmol Boc-amino acid, 1 mmol $N^\alpha$-(ω-(benzylthio)alkylene)amino acid ester, 1.1 mmol BOP and 3 mmol DIEA in 10 mL DCM was stirred at room temperature for 2 hours. Then the mixture was diluted with 40 mL of DCM and washed successively with saturated $KHSO_4$ (3×100 mL), saturated $KHCO_3$ (3×100 mL) and brine (2×100 mL), dried over $MgSO_4$ and the solvent evaporated in vacuo. The crude product was cleaned on a silica-gel column with DCM:MeOH-99:1 or crystallized from DIE:hexane.

Procedure 16

Synthesis of $N^\alpha$-Bzl ω-amino acids t-butyl esters (Bzl-NH—$(CH_2)_n$—COO-t-Bu)

A solution of 0.05 mole of amino acid t-butyl ester acetate in 200 mL $H_2O$ was acidified to pH 2 with AcOH, washed with PE (70 mL×5) cooled and the pH adjusted to 9 by $NH_4OH$ 25%. The free amino acid t-butyl ester was extracted with i-Pr:CHCl (3:1, 3×100 mL). The combined extracts were dried on $Na_2SO_4$ and evaporated to dryness under vacuum. The benzylation reaction was performed according to Procedure 2.

Procedure 17

Synthesis of $N^\alpha$-(Bzl)(ωt-Bu carboxy alkylene)glycine Bzl ester (N-(Bzl)$(CH_2)_n$—COO-t-Bu)$CH_2$—COO-Bzl)

To a stirred solution of 0.015 mole of N-Bzl ω-amino acid t-butyl ester in 10 mL DMF at 0° C. were added 2.61 mL of DIEA and 2.38 mL of benzyl bromo acetate. The reaction mixture was stirred 30 min at 0° C. and 3 h at room temperature. After the addition of 200 mL of ether, the precipitate was removed by filtration and the organic phase washed with $H_2O$ (3×80 mL), 1N HCl (3×80 mL), $H_2O$ (3×80 mL), dryed over $Na_2SO_4$ and evaporated to dryness under vacuum. The resulting oil was dried under vacuum.

Methods

ANALYTICAL TLC was performed on TLC plates of silica gel E (Merck $F_{254}$), using the following solvent systems:
METHOD A DCM:MeOH:AcOH 16:4:0.5
METHOD B PE:EtOAc 1:1
METHOD C PE:EtOAc 4:1
METHOD D $CHCl_3$:EtOAc 4:1
METHOD E PE:EtOAc 9:1
METHOD F $CHCl_3$:EtOAc 19:1
METHOD G ANALYTICAL REVERSE PHASE HPLC

| Column | Merck LICHROCART RP-18 5 μm, 250 × 4 mm. |
|---|---|
| Mobile Phases | A = 0.1% TFA in $H_2O$ |
| | B = 0.1% TFA in ACN |
| Gradient | T = 0–5 min A(75%), B(25%) |
| | T = 30 min A(50%), B(50%) |
| | T = 40 min A(100%), B(0%) |
| | T = 50 min A(100%), B(0%) |
| Flow = 1 mL/minute | Temperature = 23° C. |

METHOD H—SEMIPREPARATIVE REVERSE PHASE HPLC

The crude peptide was dissolved in MeOH (1 mL) and chromatographed using reverse phase semipreparative HPLC with the following conditions:

| Column | Merck Hibar LICHROSORB RP-18 7 μm, 250 × 410 mm |
|---|---|
| Mobile Phases | A = 0.1% TFA in $H_2O$ |
| | B = 0.1% TFA in ACN |
| Gradient | T = 0–10 min A(80%), B(20%) |
| | T = 60 min A(100%), B(0%) |
| | T = 70 min A(100%), B(0%) |
| Flow = 4 mL/minute | Temperature = 23° C. |

METHOD J NINHYDRIN TEST (NIN. TEST)

The test was performed according to Kaiser et al. *Anal. Biochem.*, 34:595 (1970) which is incorporated herein by reference in its entirety. Test was considered negative when the resin did not change color after heating to 11° C. for 2 minutes with the test mixture. Test was considered positive or slightly positive when the resin was dark or faint purple after heating to 110° C. for 2 minutes with the test mixture.

METHOD K—QUANTITATIVE PICRIC ACID TEST

Picric acid test was performed after removal of the Fmoc protecting group from the amino acid preceding the coupling of protected Nα(ω-alkylene) building unit. This absorbance was taken as 100% free amines. After coupling the test was used to check yield of t coupling by comparison.

The resin 0.1 mmole was treated according to steps 1–8, Table 1. After step 8 the resin was introduced into a centrifuge tube and shaken with 40 mL of 5% DIEA:95% DCM for ten minutes. The resin was centrifuged 5 minutes and 4 mL of the solution were pipette into 40 mL. EtOH and the absorbance at 358 nm measured. This procedure was repeated 3 times and the average absorbance calculated.

TABLE 6

PROCEDURE FOR 0.1 mMOLE SCALE

| STEP NO. | SOLVENT/ REAGENT | VOLUME (ML) | TIME (MIN) | REPEAT (XS) | COMMENT |
|---|---|---|---|---|---|
| 1 | NMP | 10 | 1 | 3 | |
| 2 | DCM | 10 | 1 | 2 | |
| 3 | Picric acid 0.05 M/DCM | 10 | 1 | 2 | |
| 4 | DMF | 10 | 0.5 | 10 | |
| 5 | NMP | 10 | 1 | 2 | |
| 6 | NMP | 10 | 2 | 3 | |
| 7 | 10% EtOH/DCM | 10 | 1 | 1 | |
| 8 | DCM | 10 | 1 | 2 | |

Compound 1

Boc diamino ethane (Known Compound)

A solution of 33.4 mL of ethylene diamine in $CHCl_3$ and 10.91 g of $Boc_2O$ were used (Procedure 1). Yield 97% of colorless oil.

TLC (Method A) Rf 0.2–0.24 (one spot)
NMR (CDCl$_3$) in agreement with the title compound Compound 2
N-Boc 1,3 diamino propane (Known Compound)
A solution of 41.7 mL of 1,3 diamino propane in CHCl$_3$ and 10.91 g of Boc$_2$O were used (Procedure 1). Yield 96% of colorless oil.
TLC (Method A) Rf 0.27–0.3 (one spot)
NMR (CDCl$_3$) in agreement with the title compound Compound 3
N-Boc 1.4 diamino butane (Known Compound)
A solution of 44.08 g of 1,4 diamino butane and 10.91 g of Boc$_2$O were used (Procedure 1). Yield 98% of white oil.
TLC (Method A) Rf 0.32–0.35 (one spot).
NMR (CDCl$_3$) in agreement with the title compound.

Compound 4
N-Boc 1,6 diamino hexane (Known Compound)
A solution of 58.10 g of 1,6 diamino hexane in CHCl$_3$ and 10.91 g of Boc$_2$O were used (Procedure 1). Yield 70% of colorless oil after purification on a silica gel column and elution with CHCl$_3$—MeOH (4:1).
TLC (Method A) Rf 0.50–0.54 (one spot)
NMR (CDCl$_3$) in agreement with the title compound Compound 5
N-Boc, N-Bzl 1,2 diamino ethan
A solution of 8.01 g of Boc ethylene diamine (COMPOUND 1) was used (Procedure 2). Yield 65% of colorless oil.
TLC (Method A) Rf 0.62–0.65 (one spot)
NMR (CDCl$_3$) in agreement with the title compound Compound 6
N-Boc, N-Bzl, 1,3 Diamino Propane
A solution of 8.71 g of N-Boc 1,3 diamino propane (COMPOUND 2) was used (Procedure 1). Yield 75% of colorless.
TLC (Method A) Rf 0.63–0.68 (one spot)
NMR (CDCl$_3$) in agreement with the title compound Compound 7
N-Boc, N-Bzl 1,4 diamino butane
A solution of 9.41 g of N-Boc 1,4 diamino butane (Compound 3) was used (Procedure 1). Yield 63% of white oil.
TLC (Method A) Rf 0.65–0.72 (one spot)
NMR (CDCl$_3$) in agreement with the title compound Compound 8
N-Boc, N-Bzl 1,6 diamino hexane
A solution of 10.82 g of N-Boc 1,6 diamino hexane (Compound 4) was used (Procedure 1). The ethyl acetate solution after extraction was dried over Na$_2$SO$_4$ and evaporated under vacuum to dryness. The remaining crude product was dissolved in 400 mL chloroform and washed with 0.5 N HCl (3×80 mL, 0.12 mole), water (2×100 mL) dried over Na$_2$SO$_4$ and evaporated to dryness. Then 200 mL of ether was added. The precipitate was filtered, washed with ether (3×50 mL) and dried under vacuum.
Yield 70% of white solid mp 150–152° C.
TLC (Method A) Rf 0.8 (one spot)
To remove HCl from product with n=6, the HCl salt was dissolved in CHCl$_3$, washed with an alkali solution (0.5% NH$_4$OH), dried over Na$_2$SO$_4$ and evaporated to dryness.
NMR (CDCl$_3$) in agreement with the title compound.

Compound 9
(S)-3-Phenylacetic acid.methyl ester (Known Compound)
A suspension of 10.8 g of (S)-3-Phenylacetic acid in 100 mL ether was treated with diazomethane (Procedure 4). Yield 85%.
TLC (Method B) Rf 0.6–0.65 (one spot)
$(\alpha)_D$=+3,3 (c=1, MeOH)
NMR (CDCl$_3$) in agreement with the title compound Compound 10
(R)-3-Phenylacetic acid methyl ester (Known Compound)
A suspension of 10.8 g (R)-3-Phenylacetic acid in 100 mL ether was treated with diazomethane (Procedure 4). Yield 84%.
TLC (Method B) Rf 0.6–0.65 (one spot)
$(\alpha)_D$=−3,3 (c=1, MeOH)
NMR (CDCl$_3$) in agreement with the title compound.

Compound 11
(S)-O-Trf-3-Phenylacetic acid methyl ester
To a cooled solution of Trf$_2$O and pyridine in dry DCM (Procedure 5), a solution of 5.4 g of (S)-3-Phenylacetic acid methyl ester was added. After the workup (Procedure 5), the yield was 74%. The product was used immediately or kept in a cold desiccator under Ar.

Compound 12
(R)-O-Trf-3-Phenylacetic acid methyl ester
To a cooled solution of Trf$_2$O and pyridine in dry DCM (Procedure 5), a solution of 5.4 g of (R)-3-Phenylacetic acid methyl ester was added. After the workup (Procedure 5), the yield was 74%. The product was used immediately or kept in a cold desiccator under Ar.

Compound 13
N$^\alpha$(Bzl)(2-Boc-amino ethylene)(R)phenylalanine methyl ester
A solution of 6.24 g of (S)-O-Trf-3-Phenyllactic acid methyl ester in dry DCM (Compound 11) was added to a solution of 5.51 g of N-Boc, N-Bzl-diamino ethane (Compound 5) in dry DCM (Procedure 6). Yield 69.2%
$(\alpha)_D$=+64.0 (c=1, MeOH)
TLC (Method C) Rf=0.41 (one spot)
NMR (CDCl$_3$) in agreement with the title compound.

Compound 14
N$^\alpha$(Bzl)(3-Boc-amino propylene)(S)phenylalanine methyl ester
A solution of 6.24 g of (R)-O-Trf-3-Phenyllactic acid methyl ester in dry DCM (Compound 12) was added to a solution of 5.82 g of N-Boc, N-Bzl-diamino propane (Compound 6) in dry DCM (Procedure 6). Yield 67.7%
$(\alpha)_D$=−55.8 (c=1, MeOH)
TLC (Method C) Rf=0.38 (one spot)
NMR (CDCl$_3$) in agreement with the title compound.

Compound 15
N$^\alpha$(Bzl)(4-Boc-amino Butylene)(S)Phenylalanine methyl ester
A solution of 6.24 g of O-Trf-(R)-3-Phenyllactic acid methyl ester in dry DCM (Compound 12) was add to a solution of 6.12 g of N-Boc, N-Bzl-diamino butane (Compound 7) in dry DCM (Procedure 6). Yield 58.6%
$(\alpha)_D$=−62.6 (c=1, MeOH)
Rf (Method C ) 0.42 (one spot)
NMR (CDCl$_3$) in agreement with the title compound.

Compound 16
N$^\alpha$(Bzl)(6-Boc-amino hexylene)(S)Phenylalanine Methyl Ester A solution of 6.24 g of O-Trf-(R)-3-Phenyllactic acid methyl ester in dry DCM (Compound 12) was add to a solution of 6.74 g of N-Boc, N-Bzl-diamino hexane (Compound 8) in dry DCM (Procedure 6). Yield 78.9%

$(\alpha)_D$=−60.0 (c=1, MeOH)

TLC (Method C) Rf=0.47 (one spot)

NMR (CDCl$_3$) in agreement with the title compound.

Compound 17
N$^\alpha$(Bzl)(3-Boc-amino Propylene)(R)Phenylalanine methyl ester A solution of 6.24 g of O-Trf-(S)-3-Phenyllactic acid methyl ester in dry DCM (Compound 11) was add to a solution of 5.82 g of N-Boc, N-Bzl-diamino propane (Compound 6) in dry DCM (Procedure 6). Yield 51.5%

$(\alpha)_D$=+58.8 (c=1, MeOH)

TLC (Method C) Rf=0.35 (one spot)

NMR (CDCl$_3$) in agreement with the title compound.

Compound 18
N$^\alpha$(Bzl)(4-Boc-amino Butylene)(R)Phenylalanine methyl ester A solution of 6.24 g of O-Trf-(S)-3-Phenyllactic acid methyl ester in dry DCM (Compound 11) was add to a solution of 6.12 g of N-Boc, N-Bzl-diamino butane (Compound 7) in dry DCM (Procedure 6). Yield 66.80%

$(\alpha)_D$=+59.0 (c=1, MeOH)

TLC (Method C) Rf=0.33 (one spot)

NMR (CDCl$_3$) in agreement with the title compound.

Compound 19
N$^\alpha$(Bzl)(3-Boc-amino propylene)(S)Phenylalanine

A solution of 6.61 g of N$^\alpha$(Bzl)(3-Boc-amino propylene)(S)Phenylalanine methyl ester in MeOH (Compound 14) was hydrolyzed by NaOH 7.5N (Procedure 7). Yield 89.5%

$(\alpha)_D$=−24.0 (c=1, MeOH)

TLC (Method B) Rf=0.16 (one spot)

NMR (CDCl$_3$) in agreement with the title compound.

Compound 20
N$^\alpha$(Bzl)(4-Boc-amino Butylene)(S)Phenylalanine

A solution of 6.61 g of N$^\alpha$(Bzl)(4-Boc-amino butylene)(S)Phenylalanine methyl ester in MeOH (Compound 15) was hydrolyzed by NaOH 7.5N (Procedure 7). Yield 73.5%

$(\alpha)_D$=−12.0 (c=1, MeOH)

TLC (Method D) Rf=0.6 (one spot)

NMR (CDCl$_3$) in agreement with the title compound.

Compound 21
N$^\alpha$(Bzl)(3-Boc-amino Propylene)(R)Phenylalanine

A solution of 6.40 g of N$^\alpha$(Bzl)(3-Boc-amino propylene)(R)Phenylalanine methyl ester in MeOH (Compound 17) was hydrolyzed by NaOH 7.5N (Procedure 7). Yield 100%

$(\alpha)_D$=+15.33 (c=1, MeOH)

TLC (Method B) Rf=0.38 (one spot)

NMR (CDCl$_3$) in agreement with the title compound.

Compound 22
N$^\alpha$(Bzl)(4-Boc-amino Butylene)(R)Phenylalanine

A solution of 6.61 g of N$^\alpha$(Bzl)(4-Boc-amino butylene)(R)Phenylalanine methyl ester in MeOH (Compound 18) was hydrolyzed by NaOH 7.5N (Procedure 7). Yield 100%

$(\alpha)_D$=+12.0 (c=1, MeOH)

TLC (Method D) Rf=0.54 (one spot)

NMR (CDCl$_3$) in agreement with the title compound.

Compound 23
N$^\alpha$(3-Boc-amino Propylene)(S)Phenylalanine HCl

A solution of 5.39 g of N$^\alpha$(Bzl)(3-Boc-amino propylene)(S)Phenylalanine (Compound 19) in MeOH-DMF was hydrogenated on Pd/C (Procedure 8). Yield 86.1%

TLC (Method A) Rf=0.51 (one spot)

NMR (D$_2$O+Na$_2$CO$_3$) in agreement with the title compound.

Compound 24
N$^\alpha$(4-Boc-amino Butylene)(S)Phenylalanine HCl

A solution of 5.56 g of N$^\alpha$(Bzl)(4-Boc-amino butylene)(S)Phenylalanine (Compound 20) in MeOH-DMF was hydrogenated on Pd/C (Procedure 8). Yield 79.25%

TLC (Method A) Rf=0.50 (one spot)

NMR (D$_2$O+Na$_2$CO$_3$) in agreement with the title compound.

Compound 25
N$^\alpha$(3-Boc-amino Propylene)(R)Phenylalanine HCl

A solution of 5.39 g of N-(Bzl)(3-Boc-amino propylene)(R)Phenylalanine (Compound 21) in MeOH-DMF was hydrogenated on Pd/C (Procedure 8). Yield 75.5%

TLC (Method A)Rf=0.51 (one spot)

NMR (D$_2$O+Na$_2$CO$_3$) in agreement with the title compound.

Compound 26
N$^\alpha$(4-Boc-amino Butylene)(R)Phenylalanine HCl

A solution of 5.56 g of N$^\alpha$Bzl)(4-Boc-amino butylene)(R)Phenylalanine (Compound 22) in MeOH-DMF was hydrogenated on Pd/C (Procedure 8). Yield 73.85%

TLC (Method A) Rf=0.50 (one spot)

NMR (D$_2$O+Na$_2$CO$_3$) in agreement with the title compound.

Example 5

Compound 27
N$^\alpha$Fmoc)(3-Boc-amino Propylene)(S)Phenylalanine

A solution of 2.51 g of N$^\alpha$(3-Boc-amino propylene)(S)Phenylalanine.HCl (Compound 23) in H$_2$O-ACN was reacted with FmocOSu (Procedure 9). Yield 64.84%

TLC (Method D) Rf=0.74 (one spot)

$(\alpha)_D$=−87 (c=1, MeOH)

HPLC (Method G) 92%

NMR (CDCl$_3$) in agreement with the title compound.

Example 6

Compound 28
N$^\alpha$(Fmoc)(3-Boc-amino Propylene)(R)Phenylalanine

A solution of 2.51 g of N$^\alpha$(3-Boc-amino propylene)(R)Phenylalanine.HCl (Compound 25) in H$_2$O-ACN was reacted with FmocOSu (Procedure 9). Yield 61.56%

TLC (Method D) Rf=0.62 (one spot)

$(\alpha)_D$=+79.6 (c=1, MeOH)

HPLC (Method G) 94%

NMR (CDCl$_3$) in agreement with the title compound.

Example 7

Compound 29
N$^\alpha$(Fmoc)(4-Boc-amino Butylene)(S)Phenylalanine
A solution of 2.61 g of N$^\alpha$(4-Boc-amino butylene)(S)Phenylalanine.HCl (Compound 24) in H$_2$O-ACN was reacted with FmocOSu (Procedure 9). Yield 56%
TLC (Method D) Rf=0.64 (one spot)
HPLC (Method G) 89%
NMR (CDCl$_3$) in agreement with the title compound.

Compound 30
O-Trf-(S)-Lactic acid methyl ester
To a cooled solution of Trf$_2$O and pyridine in DCM (Procedure 5), a solution of 2.9 mL of (S)lactic acid methyl ester was added. After the workup (Procedure 5), the yield was 70%. The product was used immediately or kept in a cold desiccator under Ar.

Compound 31
O-Trf-(R)-Lactic acid methyl ester
To a cooled solution of Trf$^2$O and pyridine in DCM (Procedure 5), a solution of 2.9 mL of (R)lactic acid methyl ester was added. After the workup (Procedure 5), the yield was 70%. The product was used immediately or kept in a cold desiccator under Ar.

Compound 32
N$^\alpha$(Bzl)(3-Boc-amino Propylene)(S)Alanine methyl ester
A solution of 4.72 g of O-Trf-(R)-lactic acid methyl ester in dry DCM (Compound 31) was add to a solution of 5.82 g of N-Boc, N-Bzl-diamino propane (Compound 6) in dry DCM (Procedure 6). Yield 69.5%
$(\alpha)_D$=−6.6 (C=1, MeOH)
TLC (Method C) Rf=0.42 (one spot)
TLC (Method D) Rf=0.92 (one spot)
TLC (Method E) Rf=0.13 (one spot)
NMR (CDCl$_3$) in agreement with the title compound.

Compound 33
N$^\alpha$(Bzl)(3-Boc-amino Propylene)(R)Alanine methyl ester
A solution of 4.72 g of O-Trf-(S-lactic acid methyl ester in dry DCM (Compound 30) was add to a solution of 5.82 g of N-Boc, N-Bzl-diamino propane (Compound 6) in dry DCM (Procedure 6). Yield 71%
$(\alpha)_D$=+6.53 (C=1, MeOH)
TLC (Method C) Rf=0.42 (one spot)
TLC (Method D) Rf=0.93 (one spot)
NMR (CDCl$_3$) in agreement with the title compound.

Compound 34
N$^\alpha$(Bzl)(6-Boc-amino hexylene)(S)Alanine methyl ester
A solution of 4.72 g of O-Trf-(R)-lactic acid methyl ester in dry DCM (Compound 31) was add to a solution of 6.74 g of N-Boc, N-Bzl-diamino hexane (Compound 8) in dry DCM (Procedure 6). Yield 81.42%
$(\alpha)_D$=−6.76 (C=1, MeOH)
TLC (Method D) Rf=0.95 (one spot)
TLC (Method E) Rf=0.26 (one spot)
NMR (CDCl$_3$) in agreement with the title compound.

Compound 35
N$^\alpha$(Bzl)(2-Boc-amino Propylene)(S)Alanine
A solution of 5.25 g of N$^\alpha$Bzl)(2-Boc-amino ethylene)(S)Alanine methyl ester in MeOH (Compound 32) was hydrolyzed by NaOH 7.5N (Procedure 7). Yield 100% of white solid, mp 64° C.
$(\alpha)_D$=+0.5 (C=1, MeOH)
TLC (Method A) Rf=0.64 (one spot)
TLC (Method D) Rf=0.47 (one spot)
NMR (CDCl$_3$) in agreement with the title compound.

Compound 36
N$^\alpha$Bzl)(6-Boc-amino Hexylene)(S)Alanine
A solution of 5.88 g of N$^\alpha$Bzl)(6-Boc-amino hexylene)(S)Alanine methyl ester (Compound 34) in MeOH was hydrolyzed by NaOH 7.5N (Procedure 7). Yield 100%
$(\alpha)_D$=+0.7 (C=1, MeOH)
TLC (Method D) Rf=0.51 (one spot)
NMR (CDCl$_3$) in agreement with the title compound.

Compound 37
N$^\alpha$(Bzl)(3-Boc-amino Propylene)(R)Alanine
A solution of 5.25 g of N$^\alpha$(Bzl)(2-Boc-amino ethylene)(R)Alanine methyl ester (Compound 35) in MeOH was hydrolyzed by NaOH 7.5N (Procedure 7). Yield 100%
$(\alpha)_D$=−0.5 (C=1, MeOH)
TLC (Method D) Rf=0.51 (one spot)
NMR (CDCl$_3$) in agreement with the title compound.

Compound 38
N$^\alpha$(3-Boc-amino Propylene)(S)Alanine.HCl
A solution of 4.47 g of N$^\alpha$(Bzl)(3-Boc-amino propylene)(S)Alanine (Compound 35) in MeOH was hydrogenated on Pd/C (Procedure 8). Yield 75%
TLC (Method A) Rf=0.42 (one spot)
NMR (CDCl$_3$) in agreement with the title compound.

Compound 39
N$^\alpha$(6-Boc-amino hexylene) (S)Alanine.HCl
A solution of 5 g of N$^\alpha$(Bzl)(4-Boc-amino hexylene)(S)Alanine (Compound 36) in MeOH-DMF was hydrogenated on Pd/C (Procedure 8). Yield 64.5% of white solid, mp 134–136° C.
TLC (Method A) Rf=0.39 (one spot)
NMR (CDCl$_3$) in agreement with the title compound.

Compound 40
N$^\alpha$(3-Boc-amino Propylene)(R)Alanine.HCl
A solution of 5 g of N$^\alpha$(Bzl)(4-Boc-amino propylene)(R)Alanine (Compound 37) in MeOH-DMF was hydrogenated on Pd/C (Procedure 8). Yield 79.1%
TLC (Method A) Rf=0.39 (one spot)
NMR (CDCl$_3$) in agreement with the title compound.

Example 8

Compound 41
N$^\alpha$(Fmoc)(3-Boc-amino Propylene)(S)Alanine
A solution of 2.82 g of N$^\alpha$(Bzl)(4-Boc-amino propylene)(S)Alanine.HCl (Compound 38) in H$_2$O-ACN was reacted with FmocOSu (Procedure 9). Yield 75% of white solid, mp 70–72° C.
TLC (Method D) Rf=0.65 (one spot)
NMR (CDCl$_3$) in agreement with the title compound.

| Elemental Analysis: | % C | % H | % N |
| --- | --- | --- | --- |
| Found: | 66.40 | 6.78 | 5.63 |
| Calc: | 66.65 | 6.88 | 5.93 |

Example 9

Compound 42
N$^\alpha$(Fmoc)(6-Boc-amino hexylene)(S)Alanine

A solution of 3.25 g of N$^\alpha$(Bzl)(4-Boc-amino hexylene) (S)Alanine.HCl (Compound 39) in H$_2$O-ACN was reacted with FmocOSu (Procedure 9). Yield 72.8% of white solid, mp 70–72° C.

TLC (Method D) Rf=0.7 (one spot)
NMR (CDCl$_3$) in agreement with the title compound.

| Elemental Analysis: | % C | % H | % N |
|---|---|---|---|
| Found: | 68.37 | 7.40 | 5.23 |
| Calc: | 68.21 | 7.50 | 5.49 |

HPLC (Method G) 90%

Example 10

Compound 43
N$^\alpha$(Fmoc)(3-Boc-amino propylene)(R)Alanine

A solution of 2.82 g of N$^\alpha$(Bzl)(4-Boc-amino propylene) (S)Alanine.HCl (Compound 40) in H$_2$O-ACN was reacted with FmocOSu (Procedure 9). Yield 75.9% of white solid, mp 70–72° C.

TLC (Method D) Rf=0.5 (one spot)
NMR (CDCl$_3$) in agreement with the title compound.

| Elemental Analysis: | % C | % H | % N |
|---|---|---|---|
| Found: | 66.4 | 6.78 | 5.63 |
| Calc: | 66.65 | 6.88 | 5.93 |

Example 11

Compound 44
N-(2-(benzylthio)ethylene)glycine ethyl ester

The title compound was prepared according to procedure 13 from ethyl bromo acetate.
Yield 75% of colorless oil.
NMR (CDCl$_3$) in agreement with the title compound.
Elemental analysis-calculated: C, 61.16; H, 7.70; N, 3.96; found: C, 61.45; H, 8.03; N, 3.49.

Compound 45
N-(3-(benzylthio)propylene)glycine methyl ester

The title compound was prepared according to procedure 13 from methyl bromo acetate.
Yield 74% of colorless oil.
NMR (CDCl$_3$) in agreement with the title compound.

Example 12

Compound 46
N-(2-(benzylthio)ethylene)(S)leucine methyl ester

The title compound was prepared according to procedure 13 from the Triflate of (R)leucine methyl ester (Procedure 5).
Yield 70% of colorless oil.
NMR (CDCl$_3$) in agreement with the title compound.
Elemental analysis-calculated: C, 65.05; H, 8.53; N, 4.74; found: C, 66.29; H, 9.03; N, 4.49.
$(a)_{D14}$=51.2° (C 0.94,DCM)

Example 13

Compound 47
N-(3-(benzylthio)propylene)(S)leucine methyl ester

The title compound was prepared according to procedure 13 from the Triflate of (R)leucine methyl ester (Procedure 5).
Yield 60% of colorless oil.
NMR (CDCl$_3$) in agreement with the title compound.
Elemental analysis-calculated: C, 65.98; H, 8.79; N, 4.53; found: C, 67.09; H, 9.20; N, 4.54.
$(\alpha)_{D23}$=−17.4° (C 1.44, DCM).

Compound 48
N-(2-(benzylthio)ethylene)(S)Phenylalanine Methyl Ester

The title compound was prepared according to procedure 13 from the Triflate of (R)phenyl lactic acid methyl ester (Procedure 5).
Yield 82% of white crystals.
m.p.=48–49° C.
NMR (CDCl$_3$) in agreement with the title compound.
Elemental analysis-calculated: C, 69.27; H, 7.04; N, 4.25; found: C, 69.55; H, 7.21; N, 4.08.
$(a)_{D14}$=−23.3° (C=1.01, DCM).

Compound 49
N-(3-(benzylthio)propylene)(S)phenylalanine methyl ester

The title compound was prepared according to procedure 13 from the Triflate of (R)phenyl lactic acid methyl ester (Procedure 5).
Yield 71% of white crystals.
m.p.=38–39° C.
NMR (CDCl$_3$) in agreement with the title compound.
Elemental analysis-calculated: C, 69.94; H, 7.34; N, 4.08; found: C, 69.66; H, 7.39; N, 4.37.
$(a)_{D26}$=+2.0° (C 1.00, DCM).

Compound 50
N-(4-(benzylthio)butylene)(S)Phenylalanine methyl ester

The title compound was prepared according to procedure 13 from the Triflate of (S)phenyl lactic acid methyl ester (Procedure 5).
Yield 8% of colorless oil.
NMR (CDCl$_3$) in agreement with the title compound.
Elemental analysis-calculated: C, 70.55; H, 7.61; N, 3.92 found: C, 70.51; H, 7.69; N, 4.22.
(a) $D_{26}$=+4.9° (C 1.00, DCM).

Example 14

Compound 51
Boc-N-(2-(benzylthio)ethylene)glycine

The title compound was prepared from Compound 44 by hydrolysis according to Procedure 11.
Yield 88% of white crystals.
m.p.=71–72° C.
NMR (CDCl$_3$) in agreement with the title compound.
Elemental analysis-calculated: C, 59.05; H, 7.12; N, 4.30; found: C, 59.39; H, 7.26; N, 4.18.

Example 15

Compound 52
Boc-N-(2-(benzylthio)ethylene)(S)phenylalanine

The title compound was prepared from Compound 48 by hydrolysis according to Procedure 11.
Yield 78% of white crystals.
m.p.=82–83° C.

NMR (CDCl$_3$) in agreement with the title compound.
(a)$_{D25}$=−105.9° (C 1.01, DCM)

Example 16

Compound 53
Boc-N-(3-(benzylthio)propylene)(S)phenylalanine

The title compound was prepared from Compound 49 by hydrolysis according to Procedure 11.
Yield 99% of white crystals.
m.p.=63–64° C.
NMR (CDCl$_3$) in agreement with the title compound.
(a)$_{D25}$=−87.4° (C 1.01, DCM).

Example 17

Compound 54
Boc-L-phenylalanyl-N-(2-(benzylthio)ethylene)glycine ethyl ester Boc-L-Phe was coupled to N-(2-(benzylthio)ethylene)glycine ethyl ester (Compound 44) according to Procedure 12.
Yield 32% of colorless oil.
NMR (CDCl$_3$) in agreement with the title compound.
Elemental analysis-calculated: C, 64.77; H, 7.25; N, 5.60; found: C, 64.39; H, 7.02; N, 5.53.
(a)$_{D16}$=+4.5° (C 0.88, DCM)

Example 18

Compound 55
Boc-L-phenylalanyl-N-(2-(benzylthio)ethylene)(S)phenylalanine methyl ester Boc-L-Phe was coupled to N-(2-(benzylthio)ethylene)(S)phenylalanine methyl ester (Compound 48) according to Procedure 12.
Yield 46% of colorless oil.
NMR (CDCl$_3$) in agreement with the title compound.
(a)$_{D26}$=−115.9° (C 1.0, CHCl$_3$).

Compound 56
N-Bzl-β-alanine t-butyl ester

A solution of 6.16 g of β-alanine t-butyl ester acetate in 150 mL water was reacted with benzaldhyde (Procedure 2) to give 4.5 g, 64.5%) yield
TLC (Method A) Rf=0.78 (one spot)
NMR (CDCl$_3$) in agreement with the title compound.

Compound 57
N-Bzl-γ-amino butyric acid t-butyl ester

A solution of 6.58 g of γ-aminobutyric acid t-butyl ester acetate in 150 mL water was reacted with benzaldhyde (Procedure 2) to give 4.24 g, 57.9% yield
TLC (Method A) Rf=0.74 (one spot)
NMR (CDCl$_3$) in agreement with the title compound.

Compound 58
N(Bzl)(2-t-butyl Carboxy Ethylene)glycine benzyl ester

A solution of 3.53 g of N-Bzl-β-alanine t-butyl ester (Compound 56) in DMF was reacted with 2.61 mL benzyl bromoacetate (Procedure 17). Yield 86.9%
TLC (Method F) Rf=0.95 (one spot)
NMR (CDCl$_3$) in agreement with the title compound.

Compound 59
N$^\alpha$Bzl)(3-t-butyl carboxy propylene)glycine benzyl ester A solution of 3.53 g of N-Bzl-γ-aminobutyric acid t-butyl ester (Compound 57) in DMF was reacted with 2.61 mL benzyl bromoacetate (Procedure 17). Yield 83%
TLC (Method F) Rf=0.92 (one spot)
NMR (CDCl$_3$) in agreement with the title compound.

Compound 60
N$^\alpha$(2-t-butyl Carboxy Ethylene)glycine

A solution of N$^\alpha$Bzl)(2-t-butyl carboxy ethylene)glycine benzyl ester (Compound 58) in MeOH was hydrogenated (Procedure 8). Yield 87.8%
TLC (Method A) Rf=0.56 (one spot)
NMR (CDCl$_3$) in agreement with the title compound.

Compound 61
N$^\alpha$(3-t-butyl carboxy propylene)glycine

A solution of N$^\alpha$(Bzl)(3-t-butyl carboxy propylene)glycine benzyl ester (Compound 59) in MeOH was hydrogenated (Procedure 8). Yield 94%
TLC (Method A) Rf=0.3 (one spot)
NMR (CDCl$_3$) in agreement with the title compound.

Example 19

Compound 62
N$^\alpha$(Fmoc)(2-t-butyl carboxy ethylene)glycine

A solution of N(2-t-butyl carboxy ethylene)glycine (Compound 60) in H$_2$O:Et$_3$N was reacted with FmocOSu (Procedure 9). Yield 90%
TLC (Method D) Rf=0.5 (one spot)
NMR (CDCl$_3$) in agreement with the title compound.

| Elemental Analysis: | % C | % H | % N |
| --- | --- | --- | --- |
| Found: | 67.38 | 6.34 | 3.11 |
| Calc: | 67.75 | 6.40 | 3.29 |

Example 20

Compound 63
N$^\alpha$(Fmoc)(3-t-butyl carboxy propylene)glycine

A solution of N$^\alpha$(3-t-butyl carboxy propylene)glycine (Compound 61) in H$_2$O:Et$_3$N was reacted with FmocOSu (Procedure 9). Yield 82%
TLC (Method D) Rf=0.58 (one spot)
NMR (CDCl$_3$) in agreement with the title compound.

| Elemental Analysis: | % C | % H | % N |
| --- | --- | --- | --- |
| Found: | 68.29 | 6.83 | 3.88 |
| Calc: | 68.32 | 6.65 | 3.19 |

Compound 64
(R)-O-Trf-3-Phenyllactic acid benzyl ester

To a cooled solution of Trf$_2$O and pyridine in dry DCM (Procedure 5), a solution of 5.3 g of (R)-3-Phenyllactic acid benzyl ester was added. After the workup (Procedure 5), the yield was 91.43%. The product was used immediately or kept in a cold desiccator under Ar.

Compound 65
N$^\alpha$(Bzl)(2-t-butyl carboxy ethylene)(S)Phenylalanine benzyl ester A solution of 5.48 g of N-Bzl-β-alanine t-butyl ester (Compound 56) in DCM was reacted with 7.35 g of (R)-O-Trf-3-Phenyllactic acid benzyl ester (COMPOUND 64) in dry DCM (Procedure 6). After workup the crude product was purified by flash chromatography. PE:EtOAc (4:1) 1.5 L. After solvent evaporation under vacuum, the product was dried under vacuum.

Yield 71.5%
TLC (Method C) Rf=0.77 (one spot)
$(\alpha)_D$=−62.7 (C=1, MeOH)
NMR (CDCl$_3$) in agreement with the title compound.

Compound 66
N$^\alpha$(2-t-butyl Carboxy Ethylene)(S)Phenylalanine
A solution of 6.3 g of N$^\alpha$(Bzl)(2-t-butyl carboxy ethylene)(S) Phenylalanine benzyl ester (Compound 65) in MeOH was hydrogenated (Procedure 8). Yield 48.6%
TLC (Method A) Rf=0.52–0.54 (one spot)
NMR (CDCl$_3$) in agreement with the title compound.

Example 21

Compound 67
N$^\alpha$(Fmoc)(2-t-butyl carboxy ethylene)(S)Phenylalanine
A solution of 2.13 g of N$^\alpha$(2-t-butyl carboxy ethylene)(S)Phenylalanine (Compound 66) in H$_2$O:Et$_3$N was reacted with FmocOSu (Procedure 9). Yield 38%
TLC (Method D) Rf=0.77 (one spot)
NMR (CDCl$_3$) in agreement with the title compound.

| Elemental Analysis: | % C | % H | % N |
| --- | --- | --- | --- |
| Found: | 71.92 | 639 | 2.87 |
| Calc: | 72.21 | 6.45 | 2.72 |

HPLC (Method G) 93%

Compound 68
N$^\alpha$(Bzl)(2-Boc Amino Ethylene)glycine Benzyl Ester
Elemental analysis-calculated: C, 59.05; H, 7.12; N, 4.30; found: C, 59.39; H, 7.26; N, 4.18.

Example 15

Compound 52
Boc-N-(2-(benzylthio)ethylene)(S)phenylalanine
The title compound was prepared from Compound 48 by hydrolysis according to Procedure 11.
Yield 78% of white crystals.
m.p.=82–83° C.
NMR (CDCl$_3$) in agreement with the title compound.
$(\alpha)_{D25}$=−105.9° (C 1.01, DCM).

Example 16

Compound 53
Boc-N-(3-(benzylthio)propylene)(S)phenylalanine
The title compound was prepared from Compound 49 by hydrolysis according to Procedure 11.
Yield 99% of white crystals.
m.p.=63–64° C.
NMR (CDCl$_3$) in agreement with the title compound.
$(\alpha)_{D25}$=−87.4° (C 1.01, DCM).

Example 17

Compound 54
Boc-L-phenylalanyl-N-(2-(benzylthio)ethylene)glycine ethyl ester
Boc-L-Phe was coupled to N-(2-(benzylthio)ethylene) glycine ethyl ester (Compound 44) according to Procedure 12.

Yield 32% of colorless oil.
NMR (CDCl$_3$) in agreement with the title compound.
Elemental analysis-calculated: C, 64.77; H, 7.25; N, 5.60; found: C, 64.39; H, 7.02; N, 5.53.
$(\alpha)_{D16}$=+4.5° (C 0.88, DCM).

Example 18

Compound 55
Boc-L-phenylalanyl-N-(2-(benzylthio)ethylene)(S) phenylalanine methyl ester
NMR (CDCl$_3$) in agreement with the title compound.

Compound 73
N$^\alpha$(3-Boc amino propylene)glycine
A solution of 0.025 mole of N$^\alpha$(Bzl)(3-Boc amino propylene)glycine benzyl ester (Compound 69) in 60 mL MeOH was hydrogenated (Procedure 8). Yield 74% of white solid. mp 214–6° C.
TLC (Method A) Rf=0.27 (one spot)
NMR (CDCl$_3$) in agreement with the title compound.

Compound 74
N$^\alpha$(4-Boc amino butylene)glycine
A solution of 0.025 mole of N$^\alpha$(Bzl)(4-Boc amino butylene)glycine benzyl ester (Compound 70) in 60 mL MeOH was hydrogenated (Procedure 8). Yield 89.5 of white solid. mp 176–8° C.
TLC (Method A) Rf=0.23 (one spot)
NMR (CDCl$_3$) in agreement with the title compound.

Compound 75
N$^\alpha$(6-Boc amino hexylene)glycine
A solution of 0.025 mole of N$^\alpha$(Bzl)(6-Boc amino hexylene)glycine benzyl ester (Compound 71) in 60 mL MeOH was hydrogenated (Procedure 8). Yield 80% of white solid. mp 172–4° C.
TLC (Method A) Rf=0.26 (one spot)
NMR (CDCl$_3$) in agreement with the title compound.

Example 22

Compound 76
N$^+$(Fmoc)(2-Boc amino ethylene)glycine
A solution of 0.02 mole of N$^\alpha$(2-Boc amino ethylene)glycine (Compound 72) in H$_2$O:Et$_3$N was reacted with FmocOSu (Procedure 9). Yield 80% of white solid. mp 130–132° C. TLC (Method D) Rf=0.5 (one spot)
NMR (CDCl$_3$) in agreement with the title compound.

| Elemental Analysis: | % C | % H | % N |
| --- | --- | --- | --- |
| Found: | 65.18 | 6.11 | 5.91 |
| Calc: | 65.43 | 6.40 | 6.63 |

Example 23

Compound 77
N$^\alpha$(Fmoc)(3-Boc amino propylene)glycine
A solution of 0.02 mole of N$^\alpha$(Fmoc)(3-Boc amino propylene)glycine (Compound 73) in H$_2$O:Et$_3$N was reacted with FmocOSu (Procedure 9). Yield 85% of white solid. mp 125° C.
TLC (Method D) Rf=0.5–0.6 (one spot)

NMR (CDCl$_3$) in agreement with the title compound.

| Elemental Analysis: | % C | % H | % N |
|---|---|---|---|
| Found: | 66.05 | 6.65 | 6.00 |
| Calc: | 66.06 | 6.65 | 6.16 |

Example 24

Compound 78

N$^\alpha$(Fmoc)(4-Boc amino butylene)glycine

A solution of 0.02 mole of N$^\alpha$(Fmoc)(4-Boc amino butylene)glycine (Compound 74) in H$_2$O:Et$_3$N was reacted with FmocOSu (Procedure 9). Yield 79.4% of white solid. mp 150–152° C.

TLC (Method D) Rf=0.42–0.47 (one spot)

NMR (CDCl$_3$) in agreement with the title compound.

| Elemental Analysis: | % C | % H | % N |
|---|---|---|---|
| Found: | 66.35 | 6.84 | 5.77 |
| Calc: | 66.06 | 6.88 | 5.98 |

Example 25

Compound 79

N$^\alpha$(Fmoc)(6-Boc amino hexylene)glycine

A solution of 0.02 mole of N$^\alpha$(Fmoc)(6-Boc amino hexylene)glycine (Compound 75) in H$_2$O:Et$_3$N was reacted with FmocOSu (Procedure 9). Yield 81.5% of white solid. mp 78–80° C. TLC (Method D) Rf=0.7 (one spot)

NMR (CDCl$_3$) in agreement with the title compound.

| Elemental Analysis: | % C | % H | % N |
|---|---|---|---|
| Found: | 68.02 | 7.08 | 5.37 |
| Calc: | 67.72 | 7.31 | 5.64 |

SYNTHETIC EXAMPLES

Two series of octapeptide somatostatin analogs of the present invention were synthesized, characterized, and tested for biological activity.

1) The first series of compounds corresponds to the general Formula (XIVb); this series comprises compounds of the specific formula

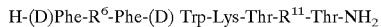

H-(D)Phe-R$^6$-Phe-(D) Trp-Lys-Thr-R$^{11}$-Thr-NH$_2$ wherein R$^6$ and R$^{11}$ are N$^\alpha$ ωW-functionalized alkylene amino acid building units.

2) The second series of compounds corresponds to the general Formula (XVIc); this series comprises compounds of the specific formula

H-(D) Phe-R$^6$-Phe-(D)Trp-Lys-R$^{10}$-Thr-NH$_2$ wherein R$^6$ and R$^{10}$ are N$^\alpha$ ω-functionalized alkylene amino acid building units.

The structures of these novel synthetic peptide analogs into which N$^\alpha$ ω-functionalized amino acid building units were incorporated, are summarized in Tables 7 and 8. In both series, the building units used were glycine building units in which the bridging groups, attached via the alpha nitrogens to the peptide backbone, were varied.

For the sake of simplicity, these two series are referred to herein as the SST Gly$^6$,Gly$^{11}$ and SST Gly$^6$,Gly$^{10}$ series, respectively.

In each series, the position of the cyclization points was constant, while the length and direction of the bridge was varied. Thus, C2,N2 refers to a bridge consisting of an amide bond in which the carbonyl group is closer to the amino end of the peptide and which contains two methylene groups between the bridge amide and each of the backbone nitrogens involved in the bridge.

Peptide assembly was carried out either manually or with an automatic peptide synthesizer (Applied Biosystems Model 433A). Following peptide assembly, de-protection of bridging groups that form the cyclization arms was carried out with Pd(PPh$_3$)$_4$ (palladium tetrakis triphenyl phosphine) in the case of Allyl/Alloc protecting groups or with TFA in the case of tBu/Boc protecting groups. For obtaining the linear (non-cyclized) analog, the peptides were cleaved from the resin at this stage. Cyclization of the peptides was carried out with PyBOP. Cleavage of the peptides from the polymeric support was carried out with suitable reagents depending on the type of resin used, e.g., with TFA for Rink amide type resins and with HF for mBHA (para-methyl benzhydryl amine) type resins. The crude products were characterized by analytical HPLC. The peptides were purified by preparative reversed phase HPLC. The purified products where characterized by analytical HPLC, mass spectroscopy, and amino acid analysis.

TABLE 7

SST Gly$^6$,Gly$^{11}$

| Example No. | Bridging Groups | Compound Number | Method | Crude Yield |
|---|---|---|---|---|
| 26 | C1,N2 Cyclic | DE-3-32-4 | 1 | NA** |
| 27 | C1,N2 Linear | DE-3-32-2 | 1 | NA |
| 28 | C1,N3 Cyclic | PTR 3004 | 2 | 79 mg |
| 29 | C1,N3 Linear | PTR 3005 | 2 | 34 mg |
| 30 | C2,N2 Cyclic | PTR 3002 | 1 | NA |
| 31 | C2,N2 Linear | PTR 3001 | 1 | NA |
| 32 | C2,N3 Cyclic | PTR 3007 | 2 | 40 mg |
| 33 | C2,N3 Linear | PTR 3008 | 2 | 40 mg |
| 34 | N2,C2 Cyclic | YD-9-166-1 | 2 | NA |
| 35 | N2,C2 Linear | YD-9-168-1 | 2 | NA |
| 36 | N3,C2 Cyclic | PTR 3010 | 2 | 100 mg |
| 37 | N3,C2 Linear | PTR 3011 | 2 | NA |
| 38 | Linear* | PTR 3003 | 3 | 96 mg |

*Linear refers to the identical sequence with Gly residues in place of R$^6$ and R$^{11}$.
**NA denotes not available.

Table 7 Methods

1) Manual synthesis on mBHA resin. HF cleavage.
2) Manual synthesis on Rapp tentagel resin. TPA age.
3) Rink amide resin; assembly in automated peptide synthesizer, 0.1 mmol scale.

TABLE 8

SST Gly$^6$, Gly$^{10}$

| Example No. | Bridging Groups | Compound Number | Method | Crude Yield |
|---|---|---|---|---|
| 39 | C1, N2 Cyclic | YD-9-171-3 | 1 | 20 mg |
| 40 | C1, N2 Linear | YD-9-171-2 | 1 | 10 mg |

TABLE 8-continued

SST Gly⁶, Gly¹⁰

| Example No. | Bridging Groups | Compound Number | Method | Crude Yield |
|---|---|---|---|---|
| 41 | C1, N3 Cyclic | YD-9-175-3 | 1 | 44.9 mg |
| 42 | C1, N3 Linear | YD-9-175-2 | 1 | 25.4 mg |
| 43 | C2, N2 Cyclic | PTR 3019 | 1 | 40 mg |
| 44 | C2, N2 Linear | PTR 3020 | 1 | 26 mg |
| 45 | C2, N3 Cyclic | YD-5-28-3 | 3 | 101.5 mg |
| 46 | C2, N3 Linear | YD-5-28-2 | 3 | 48.3 mg |
| 47 | N2, C2 Cyclic | PTR 3016 | 2 | 60 mg |
| 48 | N2, C2 Linear | PTR 3017 | 2 | 40 mg |
| 49 | N3, C2 Cyclic | YS-8-153-1 | 2 | 93 mg |
| 50 | N3, C2 Linear | YS-8-152-1 | 2 | 54 mg |
| 51 | * Linear ** Acetylated Des-D-Phe⁵ | PTR 3021 | 1 | 100 mg |
| 52 | N3, C2 Cyclic | PTR 3013 | | 67 mg |
| 53 | N3, C2 Linear | PTR 3014 | | 48 mg |

* Linear refers to the identical sequence with Gly residues in place of R⁶ and R¹⁰.
** Acetylated Des-D-Phe⁵ refers to the same sequence in which the N terminal D-Phe⁵ is absent and the N-terminus is acetylated.

Table 8 Methods
1) Assembly in automated peptide synthesizer; 0.1 scale. (HBTU).
2) Manual synthesis; PyBrop.
3) Assembly in automated peptide synthesizer, 0.25 scale. (HBTU).

Synthesis of SST Gly⁶,Gly¹⁰ N3,C2

Five grams of Rink amide resin (NOVA) (0.49 mmol/g), were swelled in N-methylpyrrolidone (NMP) in a reaction vessel equipped with a sintered glass bottom and placed on a shaker. The Fmoc protecting group was removed from the resin by reaction with 20% piperidine in NMP (2 times 10 minutes, 25 ml each). Fmoc removal was monitored by ultraviolet absorption measurement at 290 nm. A coupling cycle was carried out with Fmoc-Thr(OtBu)-OH (3 equivalents) PyBrop (3 equivalents) DIEA (6 equivalents) in NMP (20 ml) for 2 hours at room temperature. Reaction completion was monitored by the qualitative ninhydrin test (Kaiser test). Following coupling, the peptide-resin was washed with NMP (7 times with 25 ml NMP, 2 minutes each). Capping was carried out by reaction of the peptide-resin with acetic anhydride (capping mixture: HOBt 400 mg, NMP 20 ml, acetic anhydride 10 ml, DIEA 4.4 ml) for 0.5 hours at room temperature. After capping, NMP washes were carried out as above (7 times, 2 minutes each). Fmoc removal was carried out as above. Fmoc-Phe-OH was coupled in the same manner, and the Fmoc group removed, as above. The peptide resin was reacted with Fmoc-Gly-C2 (Allyl) building unit: coupling conditions were as above. Fmoc removal was carried out as above. Fmoc-Lys(Boc)-OH was coupled to the peptide resin by reaction with HATU (3 equivalents) and DIEA (6 equivalents) at room temperature overnight and then at 50° C. for one hour. Additional DIEA was added during reaction to maintain a basic medium (as determined by pH paper to be about 9). This coupling was repeated. Coupling completion was monitored by the Fmoc test (a sample of the peptide resin was taken and weighed, the Fmoc was removed as above, and the ultra-violet absorption was measured). Fmoc-D-Trp-OH was coupled to the peptide resin with PyBrop, as described above. Following Fmoc removal, Fmoc-Phe-OH was coupled in the same way. Synthesis was continued with one-fifth of the peptide resin.

Following Fmoc removal, the second building unit was introduced: Fmoc-Gly-N3(Alloc)-OH by reaction with PYBrop, as described above. Capping was carried out as described above. Following Fmoc removal, the peptide-resin was divided into two equal portions. Synthesis was continued with one of these portions. Boc-D-Phe-OH was coupled by reaction with HATU, as described above for Fmoc-Lys(Boc)-OH. Capping was carried out as above.

The Allyl and Alloc protecting groups were removed by reaction with $Pd(PPh_3)_4$ and acetic acid 5%, morpholine 2.5% in chloroform, under argon, for 2 hours at room temperature. The peptide resin was washed with NMP as above. Two-thirds of the resin were taken for cyclization. Cyclization was carried out with PyBOP 3 equivalents, DIEA 6 equivalents, in NMP, at room temperature overnight. The peptide resin was washed and dried. The peptide was cleaved from the resin by reaction with TFA 81.5%, phenol 5%, water 5%, EDT 2.5%, TIS (tri-isopropyl-silane) it, and 5% methylene chloride, at 0° C. for 15 minutes and 2 hours at room temperature under argon. The mixture was filtered into cold ether (30 ml, 0° C.) and the resin was washed with a small volume of TFA. The filtrate was placed in a rotary evaporator and all the volatile components were removed. An oily product was obtained. It was triturated with ether and the ether decanted, three times. A white powder was obtained. This crude product was dried. The weight of the crude product was 93 mg.

PHYSIOLOGICAL EXAMPLES

Example 54

Bradykinin Antagonist Assay (Displacement of ($^3$H) dopamine Release From PC 12 Cells)

Novel backbone cyclized peptide analogs of the present invention were assayed in vitro for bradykinin antagonist activity by protection of ($^3$H)dopamine release from PC 12 cells that express bradykinin receptors. PC12 cells were grown in Dulbecco Modified Eagle's medium with high glucose, supplemented with 10% horse serum, 5% fetal calf serum, 130 units/ml penicillin and 0.1 mg/ml streptomycin. For experiments, cells were removed from the medium using 1 mmole EDTA and replated on collagen coated-12-well plates and assayed 24 hr later. Release of ($^3$H)dopamine was determined as follows: cells were incubated for 1.5 hr at 37° C. with 0.5 ml of growth medium and 0.85 ml ($^3$H)DA (41 Ci/mmole) and 10 mg/ml pargyline followed by extensive washing with medium (3×1 ml) and release buffer consisting of (mM): 130 NaCl; 5 KCl; 25 $NaHCO_3$; 1 $NaH_2PO_4$; 10 glucose and 1.8 $CaCl_2$. In a typical experiment, cells were incubated with 0.5 ml buffer for 5 consecutive incubation periods of 3 min each at 37° C. Spontaneous ($^3$H)DA release was measured by collecting the medium released by the cells successively for the first 3 min period. Antagonists were added to the cells 3 min prior to stimulation (at the second period), and stimulation of ($^3$H) DA release by 100 nmole of bradykinin are monitored during the 3 period by 60 mmole KCl. The remaining of the ($^3$H)DA was extracted from the cells by over night incubation with 0.5 ml 0.1 N HCl. ($^3$H)DA release during each 3 min period was expressed as a % of the total ($^3$H)DA content of the cells. Net evoked release was calculated from ($^3$H)DA release during stimulation period after subtracting basal ($^3$H)DA release in the preceding baseline period if not indicated otherwise.

At $10^{-6}$ M, Example 1 showed 30% inhibition of BK activity, Example 4 showed 17% inhibition of BK activity.

Note, the noncyclized (control) peptide of example 2 showed 0% inhibition of BK activity.

Example 55

Bradykinin Antagonist Assay (Guinea-Pig Assay)

The ileum of the guinea-pig was selected as the preparation for the bioassay. This tissue contains predominantly $BK_2$ receptors. The preparation consists of the longitudinal muscle layer with the adhering mesenteric plexus. The isolated preparation was kept in Krebs solution and contractions were measured with an isometric force transducer. The guinea-pig ileum is highly sensitive to BK, with $EC_{50}$ at $2 \times 10^{-8}$ M. At least two control responses to BK ($2 \times 10^{-8}$ M) were measured previous to measuring the responses of backbone cyclized peptides of the present invention. Atropine (1 $\mu$M) was always present.

At $10^{-6}$ M, Example 1 showed 24% inhibition of BK activity, Example 3 showed 10% and Example 4 showed 17% inhibition of BK activity. Note, the noncyclized (control) peptide of example 2 showed 0% inhibition of BK activity.

Example 56

Somatostatin Assay (Receptor Based Screening)

Initial screening is conducted using $^{125}$I-labeled SST analogs and pituitary membrane preparations or cell lines. The binding assay is described in Tran, V. T., Beal, M. F. and Martin, J. B. *Science,* 228:294–495, 1985, which is incorporated herein by reference in its entirety and is optimized with regards to membrane concentration, temperature and time. The assay is sensitive (nM range) and robust. Selectivity will be based on the recent cloning of the five human SST receptors. The ability to screen the compounds with regard to binding and biological activity in mammalian cells should facilitate the development of subtype-selective analogs. These compounds are useful in the treatment of specific endocrine disorders and therefore should be devoid of unwanted side effects.

Example 57

Somatostatin (SST) Assay (In vivo Assays)

The biological effects of SST on growth hormone, insulin and glucagon release is conducted by measuring the levels of these hormones using commercially available RIA test kits. Pharmacological effects of SST in patients with neuroendocrine tumors of the gut will require determination of 5-hydroxyindole acetic acid (for carcinoid) and VIP (for VIPoma). In vivo visualization of SST receptor-positive tumors is performed as described by Lambert et al., *New England J. Med.,* 323:1246–1249 1990, following i.v. administration of radio-iodinated SST analogs.

Example 58

Receptor Binding Specificity of Cyclic Peptide Analogs

Binding of representative peptides of Examples 39–54 to different somatostatin receptors was measured in vitro, in Chinese Hamster Ovary (CHO) cells expressing the various receptors. An example of the selectivity obtained with the cyclic peptides is presented in Table 9. The values presented are percent inhibition of radioactive iodinated somatostatin SRIF-14) binding.

TABLE 9

Binding of peptide analogs to somatostatin receptor subtypes

| Conc. (M) | | Somatostatin Receptor (SSTR) Subtype | | | | | |
|---|---|---|---|---|---|---|---|
| Compound Description | | SSTR 2B $10^{-6}$ | $10^{-7}$ | $10^{-8}$ | SSTR 5 $10^{-6}$ | $10^{-7}$ | $10^{-8}$ |
| Compound Number | | | | | | | |
| PTR 3003 | Linear | 16 | 3 | 0 | 55 | 20 | 0 |
| PTR 3004 | Cyclic C1, N3 | 0 | 0 | 0 | 14 | 0 | 0 |
| PTR 3005 | Linear C1, N3 | 0 | 0 | 0 | 9 | 0 | 0 |
| PTR 3007 | Cyclic C2, N3 | 0 | 0 | 0 | 19 | 9 | 0 |
| PTR 3008 | Linear C2, N3 | 0 | 0 | 0 | 15 | 6 | 0 |
| PTR 3010 | Cyclic N3, C2 | 0 | 0 | 0 | 63 | 26 | 9 |
| PTR 3011 | Cyclic N3, C2 | 0 | 0 | 0 | 27 | 66 | 27 |
| Control Peptides | | | | | | | |
| BIM 3503 | Pos. Control | 81 | 33 | 16 | 92 | 66 | 27 |
| PTR 4003 | Neg. Control | 0 | 0 | 0 | 0 | 0 | 0 |

Example 59

Resistance to Biodegradation of SST Analogs

The in vitro biostability of a SST cyclic peptide analog, PTR 3002, was measured in human serum, and was compared to-the same sequence in a non-cyclic peptide analog (PTR 3001), to octreotide (Sandostatin), and to native somatostatin (SRIF). The results are shown in FIG. 1. In this assay, the cyclic peptide in accordance with the present invention is as stable as octreotide, is more stable than the corresponding non-cyclic structure, and is much more stable than SRIF. The assay was based on HPLC determination of peptide degradation as a function of time at 37° C.

Example 60

Inhibition of Growth Hormone Release by SST Analogs

In vivo determination of the pharmacodynamic properties of cyclic peptide analogs was carried out. Inhibition of Growth Hormone (GH) release as a result of peptide administration was measured. Measurements were carried out in Sprague-Dawley male rats: peptide analog activity was compared in this study to SRIF or to octreotide (Sandostatin). Each group consisted of 4 rats. Time course profiles for GH release under constant experimental conditions were measured.

Methods

Adult male Sprague-Dawley rats, specific pathogen free (SPF), weighing 200–350 g, were maintained on a constant light-dark cycle (light from 8:00 to 20:00 h), temperature (21±3° C.), and relative humidity (55±10%). Laboratory chow and tap water were available ad libitum. On the day of the experiment, rats were anesthetized with pentobarbitone (50 mg/kg). Rats anesthetized with pentobarbitone exhibit low somatostatin levels in portal blood vessels. (Plotsky, P. M., *Science,* 230, 461–463, 1985). A single blood sample (0.6 ml) was taken from the exposed cannulated jugular vein for the determination of the basal GH levels (−15 min). Immediately thereafter the appropriate peptide pretreatment was administered. The animals received 10 $\mu$g/kg of either native somatostatin (SRIF) or the synthetic analog octreotide (Sandostatin), or the cyclic peptide analog. A saline solution (0.9% NaCl) was administered as a control. All peptides were administered subcutaneously in a final volume of 0.2 ml. Further sampling was carried out at 15, 30, 60, and 90 minutes after peptide administration. Immediately after the collection of each blood sample, an appropriate volume (0.6 ml) of saline was administered intravenously. Blood samples were collected into tubes containing heparin (15 unites per ml of blood) and centrifuged immediately. Plasma was separated and kept frozen at −20° C. until assayed.

Rat growth hormone (rGH) [$^{125}$I] levels were determined by appropriate radioimmunoassay kit (Amersham). The standard in this kit has been calibrated against a reference standard preparation (NIH-RP2) obtained from the National Institute of Diabetes and Digestive and Kidney Diseases. All samples were measured in duplicate.

Example 61

Lack of Toxicity of Cyclized Peptide Analogs

PTR 3007 at a dose of 1.5 mg/kg was well tolerated after single intraperitoneal application. PTR 3013 was not toxic to the rats even with doses of 4 mg/kg. These two doses are several orders of magnitude higher than those needed to elicit the desired endocrine effect. The peptides dissolved in saline produced no untoward side effects on the central nervous system, cardiovascular system, body temperature, nor on the periphery of the animals. Rats were observed for 4 hours post administration of the peptides. PTR 3007 and 3013 produced no respiratory disturbances, did not result in the appearance of stereotyped behavior, or produce any changes in muscle tone. After 3 hours, postmortem examination did not detect any abnormality in the liver, kidneys, arteries and veins, gastrointestinal tract, lungs, genital system, nor the spleen.

What is claimed is:

1. A backbone cyclized peptide analog, wherein the backbone is cyclized to a side-chain of an amino acid of the general formula (II):

Formula (II)

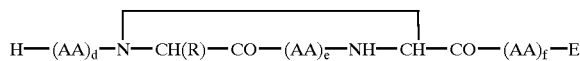

wherein d, e and f each independently designates an integer from 1 to 10; (AA) designates an amino acid residue wherein the amino acid residues in each chain may be the same or different; E represents a hydroxyl group, a carboxyl protecting or an amino group, or the E group and CO terminus of the adjacent $(AA)_f$ amino acid residue are $CH_2OH$; R is an amino acid side chain optionally bound with a specific protecting group; and the line designates a bridging group of the Formula:

(i) —X—M—Y—W—Z—; or (ii) —X—M—Z wherein M and W are independently selected from the group consisting of disulfide, amide, thioether, imine, ether, and alkene; X, Y and Z are each independently selected from the group consisting of alkylene, substituted alkylene, arylene, cycloalkylene and substituted cycloalkylene.

2. The backbone cyclized peptide analog of claim 1 wherein R is $CH_3$—, $(CH_3)_2CH$—, $(CH_3)_2CHCH_2$—, $CH_3CH_2CH(CH_3)$—, $CH_3S(CH_2)_2$—, $HOCH_2$—, $CH_3CH(OH)$—, $HSCH_2$—, $NH_2C(=O)CH_2$—, $NH_2C(=O)(CH_2)_2$—, $NH_2(CH_2)_3$—, $HOC(=O)CH_2$—, $HOC(=O)(CH_2)_2$—, $NH_2(CH_2)_4$—, $C(NH_2)_2 NH(CH_2)_3$—, HO-phenyl-$CH_2$—, benzyl, methylindole, or methylimidazole.

3. The backbone cyclized peptide analog of claim 1 wherein —X—M—Y—W—Z— is:

—(CH$_2$)$_x$—M—(CH$_2$)$_y$—W—(CH$_2$)$_z$— wherein M and W are independently selected from the group consisting of disulfide, amide, thioether, imine, ether, and alkene; x and z each independently designates an integer of from 1 to 10, and y is zero or an integer of from 1 to 8, with the proviso that if y is zero, W is absent.

4. A pharmaceutical composition comprising a therapeutically sufficient amount of a pharmacologically active backbone cyclized peptide, wherein the backbone is cyclized to a side-chain of an amino acid of the general formula (II):

Formula (II)

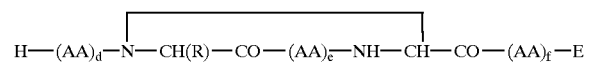

wherein d, e and f each independently designates an integer from 1 to 10; (AA) designates an amino acid residue wherein the amino acid residues in each chain may be the same or different; E represents a hydroxyl group, a carboxyl protecting or an amino group, or the E group and CO terminus of the adjacent $(AA)_f$ amino acid residue are $CH_2OH$; R is an amino acid side chain optionally bound with a specific protecting group; and the line designates a bridging group of the Formula:

(i) —X—M—Y—W—Z; or (ii) —X—M—Z— wherein M and W are independently selected from the group consisting of disulfide, amide, thioether, imine, ether, and alkene; X, Y and Z are each independently selected from the group consisting of alkylene, substituted alkylene, arylene, cycloalkylene and substituted cycloalkylene, and a pharmaceutically acceptable carrier.

5. The pharmaceutical composition of claim 4, wherein R is $CH_3$—, $(CH_3)_2CH$—, $(CH_3)_2CHCH_2$—, $CH_3CH_2CH(CH_3)$—, $CH_3S(CH_2)_2$—, $HOCH_2$—, $CH_3CH(OH)$—, $HSCH_2$—, $NH_2C(=O)CH_2$—, $NH_2C(=O)(CH_2)_2$—, $NH_2(CH_2)_3$—, $HOC(=O)CH_2$—, $HOC(=O)(CH_2)_2$—, $NH_2(CH_2)_4$—, $C(NH_2)_2 NH(CH_2)_3$—, HO-phenyl-$CH_2$—, benzyl, methylindole, or methylimidazole.

6. The pharmaceutical composition of claim 4, wherein —X—M—Y—W—Z— is:

—(CH$_2$)$_x$—M—(CH$_2$)$_y$—W—(CH$_2$)$_z$— wherein M and W are independently selected from the group consisting of disulfide, amide, thioether, imine, ether, and alkene; x and z each independently designates an integer of from 1 to 10, and y is zero or an integer of from 1 to 8, with the proviso that if y is zero, W is absent.

* * * * *

UNITED STATES PATENT AND TRADEMARK OFFICE
CERTIFICATE OF CORRECTION

PATENT NO. : 6,407,059 B1
DATED : June 18, 2002
INVENTOR(S) : Gilon et al.

It is certified that error appears in the above-identified patent and that said Letters Patent is hereby corrected as shown below:

<u>Title page,</u>
Item [73], Assignee: change "Peptor Limited, Rehovot (IL)" to -- Yissum Research Development Co. of the Hebrew University, Jerusalem; Peptor Limited, Rehovot, both of (IL) --.

Signed and Sealed this

Tenth Day of December, 2002

JAMES E. ROGAN
*Director of the United States Patent and Trademark Office*

UNITED STATES PATENT AND TRADEMARK OFFICE
CERTIFICATE OF CORRECTION

PATENT NO.        : 6,407,059 B1
APPLICATION NO. : 09/580905
DATED             : June 18, 2002
INVENTOR(S)       : Gilon et al.

It is certified that error appears in the above-identified patent and that said Letters Patent is hereby corrected as shown below:

Title Page:
(56) References Cited: add the following references under the heading
"U.S. PATENT DOCUMENTS"

| | | | |
|---|---|---|---|
| -- 3,988,304 | 10/1976 | Garsky | 260/78A |
| 4,011,182 | 3/1977 | Sarantakis | 260/8 |
| 4,054,558 | 10/1977 | Garsky | 260/112.5S |
| 4,187,217 | 2/1980 | Chipens et al. | 260/112.5R |
| 4,191,754 | 3/1980 | Veber et al. | 424/177 |
| 4,235,886 | 11/1980 | Freidinger et al. | 424/177 |
| 4,310,518 | 1/1982 | Freidinger et al. | 424/177 |
| 5,364,851 | 11/1994 | Joran | 530/345 |
| 5,371,070 | 12/1994 | Koerber et al. | 514/89 -- |

Add the following references under the heading
"FOREIGN PATENT DOCUMENTS"

| | | |
|---|---|---|
| -- DE | 4119544 | 10/1992 |
| EP | 334244A2 | 9/1989 |
| EP | 336779A2 | 10/1989 |
| EP | 370453B1 | 5/1990 |
| EP | 336779A3 | 8/1991 |
| EP | 564739A2 | 10/1993 |
| EP | 564739A3 | 4/1995 |
| FR | 2 304 352 | 10/1976 |
| FR | 2 411 828 | 7/1979 |
| WO | 89/01781 | 3/1989 |
| WO | 92/00091 | 1/1992 |
| WO | 92/22566 | 12/1992 |
| WO | 93/01206 | 1/1993 |
| WO | 94/11393 | 5/1994 -- |

At "OTHER PUBLICATIONS"
    Line 2: change "Amion" to -- Amino --.
    Line 3: change "Incorporation" to -- Incorporation --.
    Line 6: change "Contraints" to -- Constraints --.
    Line 7: change "Biopolyjmers" to -- Biopolymers --.

UNITED STATES PATENT AND TRADEMARK OFFICE
CERTIFICATE OF CORRECTION

PATENT NO. : 6,407,059 B1
APPLICATION NO. : 09/580905
DATED : June 18, 2002
INVENTOR(S) : Gilon et al.

It is certified that error appears in the above-identified patent and that said Letters Patent is hereby corrected as shown below:

Title Page (Continued):
Add the following references under the heading
"OTHER PUBLICATIONS"
-- Bell et al., 1993, "Molecular biology of somatostatin receptors", TINS, Vol. 16, No. 1, 34-38.
Brazeau et al., 1973, "Hypothalamic Polypeptide That Inhibits the Secretion of Immunoreative Pituitary Growth Hormone", SCIENCE, Vol. 179, pp. 77-79.
Buscail et al., 1995, "Inhibition of cell proliferation by the somatostatin analogue RC-160 is mediated by somatostatin receptor subtypes SSTR2 and SSTR5 through different mechanisms", *Proc. Natl. Acad. Sci. USA* 92:1580-1584.
Byk et al., 1992, "Building units for N-backbone cyclic peptides. 1. Synthesis of protected N-(ω-aminoalkylene)amino acids and their incorporation into dipeptide units", *J. Org. Chem.* 57:5687-5692.
Charpentier et al., 1989, "Synthesis and Binding Affinities of Cyclic and Related Linear Analogues of $CCK_8$ Selective for Central Receptors", *J. Med. Chem.,* pp. 1184-1190.
Giannis et al., 1993, "Peptidomimetics for Receptor Ligands--Discovery, Development, and Medical Perspectives", *Angew. Chem. Int. Ed. Engl.* 32:1244-1267.
Gilon et al., 1991, "Backbone Cyclization: A New Method for Conferring Conformational Constraint on Peptides", *Biopolymers* 31:745-750.
Gilon et al., 1992, "SAR studies of cycloseptide: Effects of cyclization and charge at position 6", *Chem. Biol.* Proc Am Pept Symp lth. pp. 476-477.
Greiner et al., 1994, "Synthesis of New Backbone-Cyclized Bradykinin Analogs", *Proc. Eur. Pept. Symp.,* 23rd Meeting Date 1994, 289-290.
Hruby et al., 1990, "Emerging approaches in the molecfular design of receptor-selective peptide ligands: conformational, topographical and dynamic considerations", *Biochem J.* 268:249-262.
Krstenansky et al., 1994, "Cyclic hexapeptide antagonists of the bradykinin $B_2$ receptor: Receptor binding and solution backbone conformation", *Letters in Peptide Science* 1:229-234.
Lamberts, 1988, "The Role of Somatostatin in the Regulation of Anterior Pituitary Hormone Secretion and the Use of Its Analogs in the Treatment of Human Pituitary Tumors", *Endocrine Reviews* Vol. 9, No. 4, pp. 417-436.
Lamberts et al., 1990, "Somatostatin-receptor imaging in the localization of endocrine tumors", *New England J. Med.* 323:1246-1249.
Lymangrover et al., 1993, "Varying the Duration of A23187 Administration Alters its Effect on Adrenal Steroidogenesis", *Life Sciences* 34:371-377.
Mosberg et al., 1983, "Bis-penicillamine enkephalins possess highly improved specificity toward δ opioid receptors", *Biochemistry* 80:5871-5874.
Plotsky et al., 1985, "Patterns of growth hormone-releasing factor and somatostatin secretion into the hypophysial-portal circulation of the rat", *Science* 230:461-463.

UNITED STATES PATENT AND TRADEMARK OFFICE
CERTIFICATE OF CORRECTION

PATENT NO. : 6,407,059 B1
APPLICATION NO. : 09/580905
DATED : June 18, 2002
INVENTOR(S) : Gilon et al.

It is certified that error appears in the above-identified patent and that said Letters Patent is hereby corrected as shown below:

Title Page (Continued):
Raynor et al., 1993, "Cloned somatostatin receptors: Identification of subtype-selective peptides and demonstration of high affinity binding of linear peptides", *Mol.Pharmacol.* 43:838-844.
Reisine et al., 1995, "Molecular biology of somatostatin receptors", *Endocrine Reviews* 16:427-442.
Reubi et al., 1995, "Multiple actions of somatostatin in neoplastic disease", *TIPS* 16:110-115.
Rizo et al., 1992, "Constrained Peptides: Models of Bioactive Peptides and Protein Sub structures", *Annu. Rev. Biochem.* 61:387-418.
Rodriguez et al., 1990, "Synthesis of cyclic analogues of cholecystokinin highly selective for central receptors", *Int. J. Peptide Protein Res.* 35:441-451.
Steranka et al., 1988, "Bradykinin as a pain mediator: Receptors are localized to sensory neurons, and antagonists have analgesic actions", *Proc. Natl. Acad. Sci. USA* 85:3245-3249.
Verber et al, 1984, "A super active cyclic hexapeptide analog of somatostatin", *Life Sciences* 34:1371-1378.
Verber et al., 1985, "The design of metabolically-stable peptide analogs", *TINS,* pp. 392-396.
Zuckerman, 1993, "The chemical synthesis of peptidomimetic libraries", *Current Opinion in Structural Biol.,* 3:580-584. --

Signed and Sealed this

Thirty-first Day of October, 2006

JON W. DUDAS
*Director of the United States Patent and Trademark Office*